United States Patent
Sakurai et al.

(10) Patent No.: US 10,351,584 B2
(45) Date of Patent: *Jul. 16, 2019

(54) ALKOXIDE COMPOUND, RAW MATERIAL FOR FORMING THIN FILM, METHOD FOR MANUFACTURING THIN FILM, AND ALCOHOL COMPOUND

(71) Applicant: ADEKA CORPORATION, Tokyo (JP)

(72) Inventors: Atsushi Sakurai, Tokyo (JP); Masako Hatase, Tokyo (JP); Tomoharu Yoshino, Tokyo (JP); Masaki Enzu, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 62 days.

This patent is subject to a terminal disclaimer.

(21) Appl. No.: 15/303,845

(22) PCT Filed: Mar. 30, 2015

(86) PCT No.: PCT/JP2015/059903
§ 371 (c)(1),
(2) Date: Oct. 13, 2016

(87) PCT Pub. No.: WO2015/163090
PCT Pub. Date: Oct. 29, 2015

(65) Prior Publication Data
US 2017/0121358 A1    May 4, 2017

(30) Foreign Application Priority Data

Apr. 21, 2014  (JP) .................. 2014-087310

(51) Int. Cl.
*C07F 15/06* (2006.01)
*C07C 251/08* (2006.01)
(Continued)

(52) U.S. Cl.
CPC ............ *C07F 15/06* (2013.01); *C07C 251/08* (2013.01); *C23C 16/18* (2013.01);
(Continued)

(58) Field of Classification Search
None
See application file for complete search history.

(56) References Cited

U.S. PATENT DOCUMENTS 9,896,468 B2 * 2/2018 Sakurai .............. C07C 251/08
2014/0227444 A1  8/2014 Winter et al.

FOREIGN PATENT DOCUMENTS

CN        103664803        3/2014
JP        2006-328019      12/2006
(Continued)

OTHER PUBLICATIONS

Marks, M.J. et al., "Metalloaldimines. 4. Reaction of Lithium Aldimines with Carbonyl Compounds and with Activated Alkyl Halides", Journal of Organic Chemistry, 1981, vol. 46, No. 26, pp. 5405-5407.
(Continued)

*Primary Examiner* — Clinton A Brooks
(74) *Attorney, Agent, or Firm* — Wenderoth, Lind & Ponack, L.L.P.

(57) ABSTRACT

An alkoxide compound is represented by General Formula (I) below:

(Continued)

wherein $R^1$ to $R^3$ each independently represent hydrogen, a $C_{1-12}$ hydrocarbon group, etc.; $R^4$ represents a $C_{1-12}$ hydrocarbon group, etc.; L represents hydrogen, halogen, a hydroxyl group, an amino group, an azi group, a phosphido group, a nitrile group, a carbonyl group, a $C_{1-12}$ hydrocarbon group, etc.; and M represents a metal atom or a silicon atom, n represents an integer of 1 or more, m represents an integer of 0 or more, and n+m represents the valence of the metal atom or silicon atom.

3 Claims, 4 Drawing Sheets

(51) Int. Cl.
  C23C 16/18    (2006.01)
  H01L 21/28    (2006.01)
  H01L 21/285   (2006.01)
  C23C 16/455   (2006.01)

(52) U.S. Cl.
  CPC ........ C23C 16/45553 (2013.01); H01L 21/28 (2013.01); H01L 21/285 (2013.01); H01L 21/28556 (2013.01); H01L 21/28568 (2013.01)

(56) References Cited

FOREIGN PATENT DOCUMENTS

| | | |
|---|---|---|
| JP | 2008-537947 | 10/2008 |
| KR | 10-0675983 | 1/2007 |
| WO | 2006/057503 | 6/2006 |
| WO | 2013/188377 | 12/2013 |

OTHER PUBLICATIONS

Ito, Y. et al., "N-Substituted Organo(silyliminomethyl)stannanes: Synthetic Equivalent to Organosilylcarbonyl Anion and Carbonyl Dianion", Journal of the American Chemical Society, 1987, vol. 109, No. 25, p. 7888-7890.

De Vries, E.F.J. et al., "Stereoselective Reduction of Prochiral Ketones, Using Aluminum Hydride Reagents Prepared from LiAlH₄ and Chiral Diethanolamines", Tetrahedron: Asymmetry, 1994, vol. 5, No. 3, p. 377-386.

Annunziata, R. et al., "Stereoselective Synthesis of β-lactams by Condensation of Titanium Enolates of 2-pyridyl Thioesters with Imines Bearing a Chiral Auxiliary", Tetrahedron, 1994, vol. 50, No. 31, p. 9471-9486.

Palomo, C. et al., "A Facile Access to Peptides Containing D-α-methyl β-alkylserines by Coupling of α-Branched Leuchs Anhydrides with α-Amino Esters", Journal of the Chemical Society, Chemical Communications, 1995, No. 22, p. 2327-2328.

Takaki, K. et al., "Ti(NMe₂)₄-catalyzed markovnikov hydroamination of alkynes in the presence of N-heterocyclic carbenes and LiN(SiMe₃)₂", Tetrahedron Letters, 2006, vol. 47, No. 41, p. 7335-7337.

Packter, A. et al., "The Precipitation of Sparingly Soluble Metal Salts Factors Affecting Crystal Form and Anisometry (II)", Kristall Und Technik, 1969, vol. 4, No. 1, p. 45-55.

Iball, J. et al., "The Crystal and Molecular Structure of Bis-α-Hydroxy-α-Phenylbutyramidinecopper(II)", Journal of the Chemical Society [Section] A: Inorganic, Physical, Theoretical, 1967, No. 1, p. 52-56.

Attia, A.S. et al., "Synthesis and characterization of a monomeric and a dihydroxo-bridged dimeric complexes of iron(III) with α-benzoinoxime", Polyhedron, 2007, vol. 26, No. 4, p. 791-796.

Keeney, M.E. et al., "Synthesis and characterization of copper and nickel complexes of LIX63 oxime", Polyhedron, 1984, vol. 3, No. 6, p. 641-649.

Skorokhod, L.S. et al., "Nickel(II) and Cobalt(II) Complexes with Products of Condensation of 1-Aminonaphthalene, 2-Aminonaphthalenesulfonic-5 Acid, and Aromatic Carbinols", Russian Journal of Coordination Chemistry (Translation of Koordinatsionnaya Khimiya), 2002, vol. 28, No. 9, p. 643-646.

Shimizu, M. et al., "Reductive Coupling of Aldehydes With Nitriles Promoted by Titanium Tetraiodide", Letters in Organic Chemistry, 2004, vol. 1, No. 4, p. 346-348.

Alonso, E. et al., "Imidoyllithiums: Masked Acyllithium Reagents", Tetrahedron Letters, 1997, vol. 38, No. 51, p. 8903-8906.

Friary, R. et al., "Alleged Alkylations of α-Hydroxyimines to Betaines: Revisions of the Structures of Educts and Products", Journal of the Chemical Society, Chemical Communications, 1984, No. 20, p. 1383.

Kalutarage, L.C. et al., Volatile and Thermally Stable Mid to Late Transition Metal Complexes Containing α-Imino Alkoxide Ligands, a New Strongly Reducing Coreagent, and Thermal Atomic Layer Deposition of Ni, Co, Fe, and Cr Metal Films, Journal of the American Chemical Society, 2013, vol. 135, No. 34, p. 12588-12591.

International Search Report dated Jun. 30, 2015 in International Application No. PCT/JP2015/059903.

Extended European Search Report dated Sep. 28, 2017 in counterpart European Application No. 15782391.5.

Kalutarage et al., "Volatile and Thermally Stable Mid to Late Transition Metal Complexes Containing α-Imino Alkoxide Ligands, a New Strongly Reducing Coreagent, and Thermal Atomic Layer Deposition of Ni, Co, Fe, and Cr Metal Films", Journal of the American Chemical Society, vol. 135, No. 34, 2013, pp. 12588-12591.

Shukla et al., "Biotransformation of benzaldehyde to L-phenylacetylcarbinol (L-PAC) by Torulaspora delbrueckii and conversion to ephedrine by microwave radiation", Journal of Chemical Technology and Biotechnology, vol. 77, No. 2, 2002, pp. 137-140.

Kreutz et al., "Baker's yeast reduction of (E)-1-phenyl-1,2-propanedione 2-(O-methyloxime). A key step for a (−)-norephedrine synthesis", Tetrahedron: Asymmetry, vol. 8, No. 15, 1997, pp. 2649-2653.

Gilly et al., "Synthesis and evaluation of pharmacological CNS activity of α-hydroxy O-alkyl etheroximes", European Journal of Medicinal Chemistry, vol. 28, No. 11, 1993, pp. 905-909.

Paterson et al., "A fully stereocontrolled total synthesis of (+)-leucascandrolide A", Tetrahedron, vol. 59, No. 35, 2003, pp. 6833-6849.

Palomo et al., "A Facile Access to Peptides Containing D-α-methyl β-Alkylserines by Coupling of α-Branched Leuchs Anhydrides with α-Amino Esters", Journal of the Chemical Society, Chemical Communications, vol. 22, 1995, pp. 2327-2328.

Bolm et al., "Catalyzed Enantioselective Borane Reduction of Ketimine Derivatives", SYNLETT, vol. 8, 1994, pp. 655-656.

De Vries et al., "Stereoselective Reduction of Prochiral Ketones, Using Aluminum Hydride Reagents Prepared from LiAlH₄, and Chiral Diethanolamines", Tetrahedron: Asymmetry, vol. 5, No. 3, 1994, pp. 377-386.

* cited by examiner

ALKOXIDE COMPOUND, RAW MATERIAL FOR FORMING THIN FILM, METHOD FOR MANUFACTURING THIN FILM, AND ALCOHOL COMPOUND

TECHNICAL FIELD

The present invention relates to a novel alkoxide compound, a raw material for forming a thin film that includes the compound, a method for manufacturing a thin film by using the raw material for forming a thin film, and a novel alcohol compound.

BACKGROUND ART

Thin-film materials including a metal element have been used for a variety of applications because such materials exhibit electric properties, optical properties and the like. For example, copper and copper-containing thin films have been used as wiring materials for LSI because of a high electric conductivity, high resistance to electromigration, and a high melting point. Further, nickel and nickel-containing thin films are mainly used for parts of electronic components such as resistive films and barrier films, parts for recording media such as magnetic films, and parts for thin-film solar cells, such as electrodes. Cobalt and cobalt-containing thin films have been used for electrode films, resistive films, adhesive films, magnetic tapes, ultra-hard tool members and the like.

Examples of methods for manufacturing such thin films include a sputtering method, an ion plating method, a MOD method such as a coating pyrolysis method and a sol-gel method, and a chemical vapor deposition method. The chemical vapor deposition (referred to hereinbelow simply as CVD) method, inclusive of an ALD (Atomic Layer Deposition) method, is an optimum manufacturing process because it has advantages such as being suitable for mass production, exceling in composition controllability and stepwise coating ability, and enabling hybrid accumulation.

A large number of various materials have been reported as metal-supplying sources for use in the chemical vapor deposition method. For example, Patent Document 1 discloses a tert-aminoalkoxide compound of nickel that can be used as a raw material for forming a nickel-containing thin film by a MOCVD method. Further, Patent Document 2 discloses a tert-aminoalkoxide compound of cobalt that can be used as a raw material for forming a cobalt-containing thin film by the MOCVD method. Patent Document 3 discloses a tert-aminoalkoxide compound of copper that can be used as a raw material for forming a copper-containing thin film by the chemical vapor deposition method. Further, Non-Patent Document 1 discloses tert-imidoalkoxide compounds of copper, nickel, cobalt, iron, manganese, and chromium.

Patent Document 1: Japanese Translation of PCT Application No. 2008-537947
Patent Document 2: Korean Patent Registration No. 10-0675983
Patent Document 3: Japanese Patent Application Publication No. 2006-328019
Non-Patent Document 1: J. Am. Chem. Soc., 2013, 135, 12588-12591

SUMMARY OF INVENTION

Technical Problem

When a thin film is formed by vaporizing a raw material for chemical vapor deposition, properties required from compounds (precursors) suitable for the raw materials include absence of spontaneous combustibility and high thermal stability. In particular, high thermal stability is extremely important for the precursor in the ALD method. None of the conventional alkoxide compounds are sufficiently satisfactory in terms of thermal stability.

Solution to the Problem

The present inventors have carried out investigations and discovered that the abovementioned problems can be solved by a specific alkoxide compound, to achieve the present invention.

The present invention provides an alkoxide compound represented by General Formula (I) below, a raw material for forming a thin film that includes the compound, and a method for manufacturing a thin film by using the raw material.

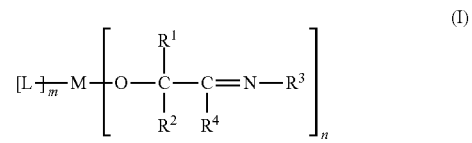

In the formula, $R^1$ to $R^3$ each independently represent hydrogen, a $C_{1-12}$ hydrocarbon group, or a group represented by General Formulas (X-1) to (X-8) below; $R^4$ represents a $C_{1-12}$ hydrocarbon group or a group represented by General Formulas (X-1) to (X-8) below; provided that when $R^1$ is a methyl group, $R^2$ is a methyl group or an ethyl group and $R^4$ is a methyl group, $R^3$ represents hydrogen, a $C_{4-12}$ hydrocarbon group or a group represented by General Formulas (X-1) to (X-8) below; L represents hydrogen, halogen, a hydroxyl group, an amino group, an azi group, a phosphido group, a nitrile group, a carbonyl group, a $C_{1-12}$ hydrocarbon group or a group represented by General Formulas (L-1) to (L-13) below; and M represents a metal atom or a silicon atom, n represents an integer of 1 or more, m represents an integer of 0 or more, and n+m represents the valence of the metal atom or silicon atom.

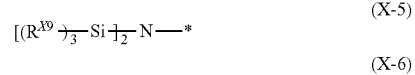

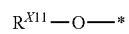 (X-7)

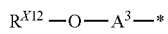 (X-8)

In the formulas, $R^{X1}$ to $R^{X12}$ each independently represent hydrogen or a $C_{1-12}$ hydrocarbon group; $A^1$ to $A^3$ each represent a $C_{1-6}$ alkanediyl group.

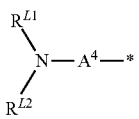 (L-1)

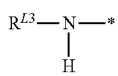 (L-2)

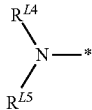 (L-3)

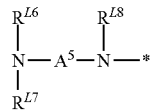 (L-4)

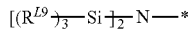 (L-5)

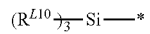 (L-6)

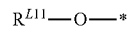 (L-7)

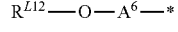 (L-8)

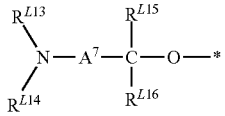 (L-9)

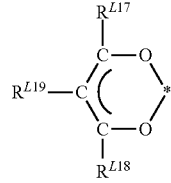 (L-10)

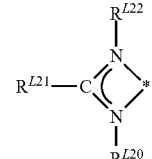 (L-11)

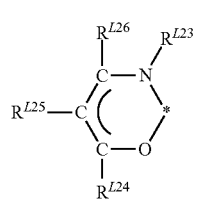 (L-12)

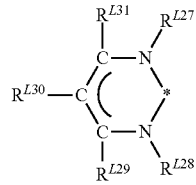 (L-13)

In the formulas, $R^{L1}$ to $R^{L31}$ each independently represent hydrogen or a $C_{1-12}$ hydrocarbon group; $A^4$ to $A^7$ each represent a $C_{1-6}$ alkanediyl group; provided that when $R^{L1}$ to $R^{L31}$ are each a $C_{1-12}$ hydrocarbon group, a hydrogen atom in the hydrocarbon group may be substituted with a halogen atom or an amino group.

The present invention also provides an alcohol compound represented by General Formula (II) below.

$$H-O-\underset{\underset{R^6}{|}}{\overset{\overset{R^5}{|}}{C}}-\underset{\underset{R^8}{|}}{C}=N-R^7 \qquad (II)$$

In the formula, $R^5$ to $R^7$ each independently represent hydrogen, a $C_{1-12}$ hydrocarbon group, or a group represented by General Formulas (Y-1) to (Y-8) below; $R^8$ represents a $C_{1-12}$ hydrocarbon group or a group represented by General Formulas (Y-1) to (Y-8) below; provided that when $R^5$ is a methyl group, $R^6$ is a methyl group or an ethyl group and $R^8$ is a methyl group, $R^7$ represents hydrogen, a $C_{4-12}$ hydrocarbon group or a group represented by General Formulas (Y-1) to (Y-8) below.

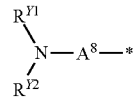 (Y-1)

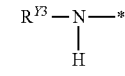 (Y-2)

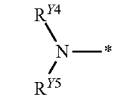 (Y-3)

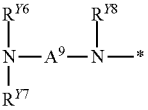 (Y-4)

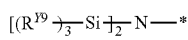 (Y-5)

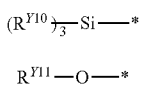 (Y-6)

 (Y-7)

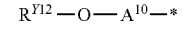 (Y-8)

In the formulas, $R^{Y1}$ to $R^{Y12}$ each independently represent hydrogen or a $C_{1-12}$ hydrocarbon group, and $A^8$ to $A^{10}$ each represent a $C_{1-6}$ alkanediyl group.

Advantageous Effects of the Invention

In accordance with the present invention, it is possible to obtain an alkoxide compound with high thermal stability and no spontaneous combustibility. The present invention also can provide a novel alcohol compound.

DESCRIPTION OF EMBODIMENTS

Figure 1:
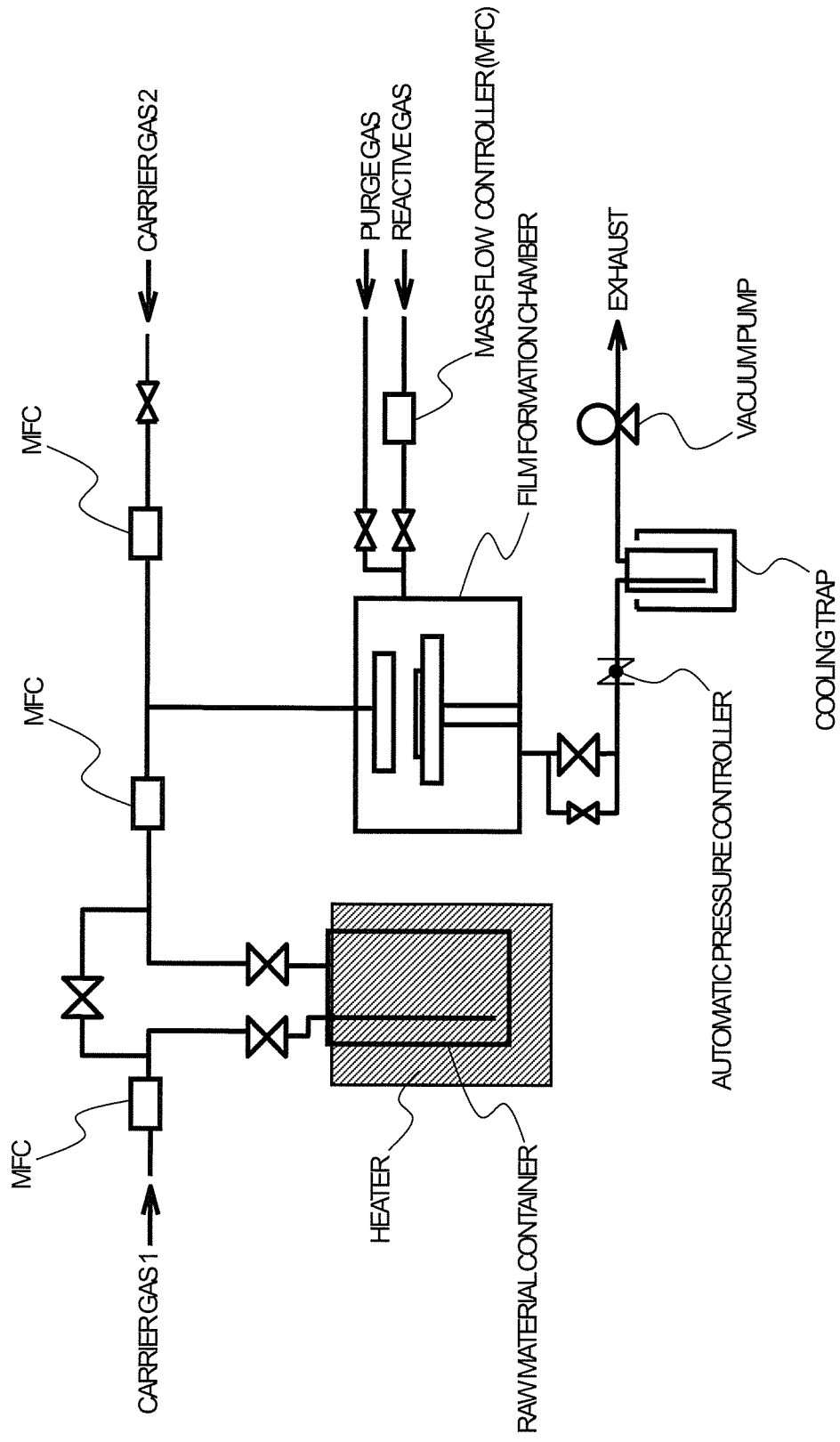
FIG. 1 is a conceptual diagram illustrating an example of a chemical vapor deposition apparatus for use in the method for manufacturing a metal-containing thin film in the present invention.

The alkoxide compound in accordance with the present invention is represent by General Formula (I) above. This compound is advantageous as a precursor for a thin film manufacturing method having a vaporization step, such as the CVD method, and because of high thermal stability, this compound is particularly advantageous as a precursor to be used in the ALD method.

In General Formula (I) of the present invention, $R^1$ to $R^3$ each independently represent hydrogen, a $C_{1-12}$ hydrocarbon group, or a group represented by General Formulas (X-1) to (X-8) above.

For example, an alkyl, an alkenyl, a cycloalkyl, an aryl, or a cyclopentadienyl can be used as the $C_{1-12}$ hydrocarbon group which is represented by $R^1$ to $R^3$.

Examples of the alkyl include methyl, ethyl, propyl, isopropyl, butyl, isobutyl, sec-butyl, tert-butyl, pentyl, isopentyl, hexyl, heptyl, isoheptyl, octyl, isooctyl, 2-ethylhexyl, nonyl, isononyl, decyl, and dodecyl.

Examples of the alkenyl include vinyl, 1-methylethenyl, 2-methylethenyl, propenyl, butenyl, isobutenyl, pentenyl, hexenyl, heptenyl, octenyl, and decenyl.

Examples of the cycloalkyl include cyclohexyl, cyclopentyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl.

Examples of the aryl include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, and 4-cyclohexylphenyl.

Examples of the cyclopentadienyl include cyclopentadienyl, methylcyclopentadienyl, ethylcyclopentadienyl, propylcyclopentadienyl, isopropylcyclopentadienyl, butylcyclopentadienyl, sec-butylcyclopentadienyl, isobutylcyclopentadienyl, tert-butylcyclopentadienyl, dimethylcyclopentadienyl, and tetramethylcyclopentadienyl.

In General Formula (I) of the invention, $R^4$ represents a $C_{1-12}$ hydrocarbon group or a group represented by General Formulas (X-1) to (X-8) above.

Specific examples of the $C_{1-12}$ hydrocarbon group which is represented by $R^4$ can be the same as those listed hereinabove as the examples of the $C_{1-12}$ hydrocarbon group which is represented by $R^1$ to $R^3$.

In General Formulas (X-1) to (X-8), $R^{X1}$ to $R^{X12}$ each independently represent hydrogen or a $C_{1-12}$ hydrocarbon group, and $A^1$ to $A^3$ each represent a $C_{1-6}$ alkanediyl group.

Specific examples of the $C_{1-12}$ hydrocarbon group which is represented by $R^{X1}$ to $R^{X12}$ can be the same as those listed hereinabove as the examples of the $C_{1-12}$ hydrocarbon group which is represented by $R^1$ to $R^3$.

Examples of the $C_{1-6}$ alkanediyl group which is represented by $A^1$ to $A^3$ include methylene, ethylene, propylene, and butylene.

Examples of the group represented by General Formula (X-1) include dimethylaminomethyl, ethylmethylaminomethyl, diethylaminomethyl, dimethylaminoethyl, ethylmethylaminoethyl, and diethylaminoethyl.

Examples of the group represented by General Formula (X-2) include methylamino, ethylamino, propylamino, isopropylamino, butylamino, sec-butylamino, tert-butylamino, and isobutylamino.

Examples of the group represented by General Formula (X-3) include dimethylamino, diethylamino, dipropylamino, diisopropylamino, dibutylamino, di-sec-butylamino, di-tert-butylamino, ethylmethylamino, propylmethylamino, and isopropylmethylamino.

Examples of compounds providing the group represented by General Formula (X-4) include ethylenediamino, hexamethylenediamino, and N,N-dimethylethylenediamino.

Examples of the group represented by General Formula (X-5) include di(trimethylsilyl)amino and di(triethylsilyl)amino.

Examples of the group represented by General Formula (X-6) include trimethylsilyl and triethylsilyl.

Examples of the group represented by General Formula (X-7) include methoxy, ethoxy, propoxy, isopropoxy, butoxy, sec-butoxy, isobutoxy, tert-butoxy, pentoxy, isopentoxy, and tert-pentoxy.

Examples of the group represented by General Formula (X-8) include hydroxymethyl, hydroxyethyl, hydroxypropyl, hydroxyisopropyl, and hydroxybutyl.

In General Formula (I), where $R^1$ is a methyl group, $R^2$ is a methyl group or an ethyl group, and $R^4$ is a methyl group, $R^3$ represents hydrogen, a $C_{4-12}$ hydrocarbon group or a group represented by General Formulas (X-1) to (X-8) below.

Examples of the $C_{4-12}$ hydrocarbon group include $C_{4-12}$ alkyls, $C_{4-12}$ alkenyls, $C_{6-12}$ cycloalkyls, and $C_{6-12}$ aryls.

Examples of the $C_{4-12}$ alkyls include butyl, isobutyl, sec-butyl, tert-butyl, pentyl, isopentyl, hexyl, heptyl, isoheptyl, octyl, isooctyl, 2-ethylhexyl, nonyl, isononyl, decyl, and dodecyl.

Examples of the $C_{4-12}$ alkenyls include butenyl, isobutenyl, pentenyl, hexenyl, heptenyl, octenyl, and decenyl.

Examples of the $C_{6-12}$ cycloalkyls include cyclohexyl, cyclopentyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl.

Examples of the $C_{6-12}$ aryls include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, and 4-cyclohexylphenyl.

Where $R^1$, $R^2$, $R^3$, and $R^4$ in General Formula (I) are used in a thin film manufacturing method including a step of vaporizing the compound, it is preferred that the vapor pressure and thermal decomposition temperature thereof be high. More specifically, it is preferred that $R^1$ and $R^2$ each independently represent hydrogen, a $C_{1-12}$ hydrocarbon group, or a group represented by General Formula (X-5) because a high vapor pressure is realized. Among them, it is more preferred that at least one of $R^1$ and $R^2$ be a $C_{1-5}$ alkyl, di(trimethylsilyl)amino, or di(triethylsilyl)amino because an especially high vapor pressure is realized, and it is most preferred that at least one of $R^1$ and $R^2$ be a $C_{1-5}$ alkyl, di(trimethylsilyl)amino, or di(triethylsilyl)amino and at least one of $R^3$ and $R^4$ be a $C_{1-5}$ alkyl, di(trimethylsilyl)amino, or di(triethylsilyl)amino because a particularly high vapor pressure is realized. Further, it is preferred that $R^4$ be a $C_{1-12}$ hydrocarbon group, a group represented by General Formula (X-3), or a group represented by General Formula (X-5) because high thermal stability is realized. Among them, it is more preferred that $R^4$ be an alkenyl group, an alkyl, di(trimethylsilyl)amino, or di(triethylsilyl)amino because a particularly high thermal stability is realized. Further, in the case of a thin film manufacturing method based on the MOD method which does not involve a vaporization step, $R^1$, $R^2$, $R^3$, and $R^4$ can be selected, as appropriate, according to the solubility in the solvent used, the thin film formation reaction and the like.

In General Formula (I) of the present invention, L represents hydrogen, halogen, a hydroxyl group, an amino group, an azi group, a phosphido group, a nitrile group, a carbonyl group, a $C_{1-12}$ hydrocarbon group or a group represented by General Formulas (L-1) to (L-13). $R^{L1}$ to $R^{L31}$ in General Formulas (L-1) to (L-13) each independently represent hydrogen or a $C_{1-12}$ hydrocarbon group, and $A^4$ to $A^7$ each represent a $C_{1-6}$ alkanediyl group. Where $R^{L1}$ to $R^{L31}$ in General Formulas (L-1) to (L-13) each are a $C_{1-12}$ hydrocarbon group, a hydrogen atom in the hydrocarbon group may be substituted with a halogen atom or an amino group.

Specific examples of the $C_{1-12}$ hydrocarbon group which is represented by $R^{L1}$ to $R^{L31}$ can be the same as those listed hereinabove as the examples of the $C_{1-12}$ hydrocarbon group which is represented by $R^1$ to $R^3$.

Specific examples of the $C_{1-6}$ alkanediyl group which is represented by $A^4$ to $A^7$ can be the same as those listed hereinabove as the examples of the $C_{1-6}$ alkanediyl group which is represented by $A^1$ to $A^3$.

Examples of the group represented by General Formula (L-1) include dimethylaminomethyl, ethylmethylaminomethyl, diethylaminomethyl, dimethylaminoethyl, ethylmethylaminoethyl, and diethylaminoethyl.

Examples of the group represented by General Formula (L-2) include methylamino, ethylamino, propylamino, isopropylamino, butylamino, sec-butylamino, tert-butylamino, and isobutylamino.

Examples of the group represented by General Formula (L-3) include dimethylamino, diethylamino, dipropylamino, diisopropylamino, dibutylamino, di-sec-butylamino, di-tert-butylamino, ethylmethylamino, propylmethylamino, and isopropylmethylamino.

Examples of compounds providing the group represented by General Formula (L-4) include ethylenediamino, hexamethylenediamino, and N,N-dimethylethylenediamino.

Examples of the group represented by General Formula (L-5) include di(trimethylsilyl)amino and di(triethylsilyl) amino.

Examples of the group represented by General Formula (L-6) include trimethylsilyl and triethylsilyl.

Examples of the group represented by General Formula (L-7) include methoxy, ethoxy, propoxy, isopropoxy, butoxy, sec-butoxy, isobutoxy, tert-butoxy, pentoxy, isopentoxy, and tert-pentoxy.

Examples of the group represented by General Formula (L-8) include hydroxymethyl, hydroxyethyl, hydroxypropyl, hydroxyisopropyl, and hydroxybutyl.

Examples of the group represented by General Formula (L-9) include dimethylaminoethoxy, diethylaminoethoxy, dimethylaminopropoxy, ethylmethylaminopropoxy, and diethylaminopropoxy.

Examples of the group represented by General Formula (L-10) include groups represented by Chemical Formulas No. (L-10-1) to (L-10-5) below. In Chemical Formulas No. (L-10-1) to (L-10-5), "Me" represents methyl, "Et" represents ethyl, "iPr" represents isopropyl, and "tBu" represents tert-butyl.

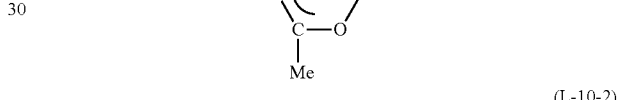

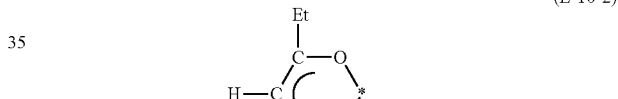

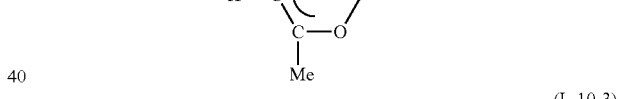

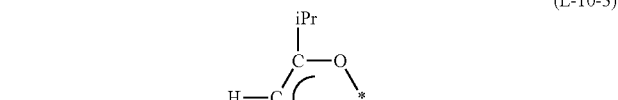

Examples of organic compounds providing the group represented by General Formula (L-10) include acetylacetone, hexane-2,4-dione, 5-methylhexane-2,4-dione, heptane-2,4-dione, 2-methylheptane-3,5-dione, 2,6-dimethylheptane-3,5-dione, 1,1,1-trifluoropentane-2,4-dione, 1,1,1-trifluoro-5,5-dimethylhexane-2,4-dione, 1,1,1,5,5,5-hexafluoropentane-2,4-dione, 1,3-diperfluorohexylpropane-1,3-dione, 1,1,5,5-tetramethyl-1-methoxyhexane-2,4-dione, 2,2,6,6-tetramethyl-1-methoxyheptane-3,5-dione, 2,2,6,6-tetramethyl-1-(2-methoxyethoxy)heptane-3,5-dione, 1,1,1-trifluoropentane-2,4-dione, 1,1,1-trifluoro-5,5-dimethylhexane-2,4-dione, 1,1,1,5,5,5-hexafluoropentane-2,4-dione, 1,3-diperfluorohexylpropane-1,3-dione, 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione.

Examples of the group represented by General Formula (L-11) include groups represented by Chemical Formulas No. (L-11-1) to (L-11-3) below. In Chemical Formulas No. (L-11-1) to (L-11-3), "Me" represents methyl, "iPr" represents isopropyl, and "tBu" represents tert-butyl.

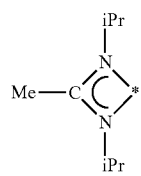
(L-11-1)

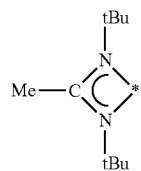
(L-11-2)

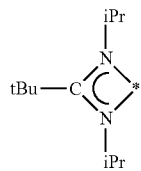
(L-11-3)

Examples of organic compounds providing the group represented by General Formula (L-11) include N,N'-diisopropylacetamidinate, N,N'-di-t-butylacetamidinate, and N,N'-diisopropyl-2-t-butylamidinate.

Examples of the group represented by General Formula (L-12) include groups represented by Chemical Formulas No. (L-12-1) to (L-12-8) below. In Chemical Formulas No. (L-12-1) to (L-12-8), "Me" represents methyl, "iPr" represents isopropyl, and "tBu" represents tert-butyl.

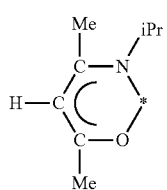
(L-12-1)

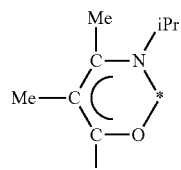
(L-12-2)

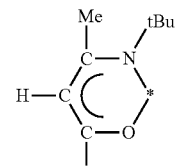
(L-12-3)

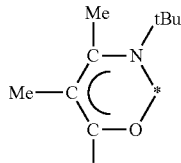
(L-12-4)

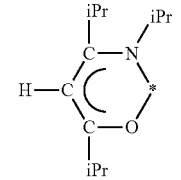
(L-12-5)

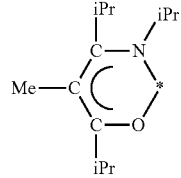
(L-12-6)

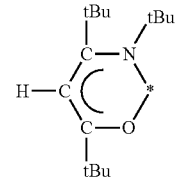
(L-12-7)

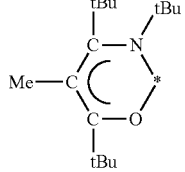
(L-12-8)

Examples of organic compounds providing the group represented by General Formula (L-12) include reaction products of diketone compounds represented by acetylacetone, hexane-2,4-dione, 5-methylhexane-2,4-dione, heptane-2,4-dione, 2-methylheptane-3,5-dione, 2,6-dimethylheptane-3,5-dione, 1,1,1-trifluoropentane-2,4-dione, 1,1,1-trifluoro-5,5-dimethylhexane-2,4-dione, 1,1,1,5,5,5-hexafluoropentane-2,4-dione, 1,3-diperfluorohexylpropane-1,3-dione, 1,1,5,5-tetramethyl-1-methoxyhexane-2,4-dione, 2,2,6,6-tetramethyl-1-methoxyheptane-3,5-dione, and 2,2,6,6-tetramethyl-1-(2-methoxyethoxy)heptane-3,5-dione, and organic amine compounds represented by methylamine, ethylamine, propylamine, isopropylamine, butylamine, sec-butylamine, tert-butylamine, isobutylamine, dimethylamine, diethylamine, dipropylamine, di isopropyl amine, ethylmethylamine, propylmethylamine, isopropylmethylamine, ethylenediamine, and N,N-dimethylethylenediamine.

Examples of the group represented by General Formula (L-13) include groups represented by Chemical Formulas No. (L-13-1) to (L-13-8) below. In Chemical Formulas No. (L-13-1) to (L-13-8), "Me" represents methyl, "iPr" represents isopropyl, and "tBu" represents tert-butyl.

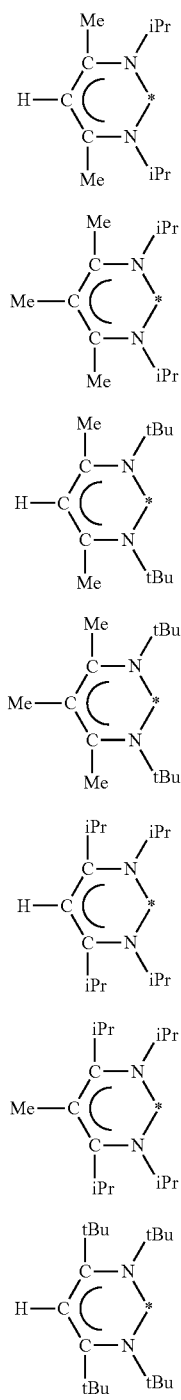

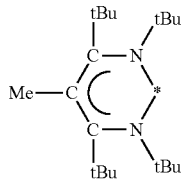

Examples of organic compounds providing the group represented by General Formula (L-13) include N-isopropyl-4-(isopropylimino)pent-2-ene-2-amine, N-isopropyl-4-(isopropylimino)-3-methylpent-2-ene-2-amine, N-(tert-butyl)-4-(tert-butylimino)pent-2-ene-2-amine, N-(tert-butyl)-4-(tert-butylimino)-3-methylpent-2-ene-2-amine, N-isopropyl-5-(isopropylimino)-2,6-dimethylhept-3-ene-3-amine, N-isopropyl-5-(isopropylimino)-2,4,6-trimethylhept-3-ene-3-amine, N-(tert-butyl)-5-(tert-butylimino)-2,2,6,6-tetramethylhept-3-ene-3-amine, and N-(tert-butyl)-5-(tert-butylimino)-2,2,4,6,6-pentamethylhept-3-ene-3-amine.

Where m is 1 or more in General Formula (I), it is particularly preferred that L be a cyclopentadienyl group represented by cyclopentadienyl, methylcyclopentadienyl, ethylcyclopentadienyl, and pentamethylcyclopentadienyl, or a group represented by (L-11) because in such cases the thermal stability is high and vapor pressure is high. Further, where m is 2 or more in General Formula (I), L may be the same or different.

M in General Formula (I) is a metal atom or a silicon atom. The metal atom is not particularly limited, and examples thereof include lithium, sodium, potassium, magnesium, calcium, strontium, barium, radium, scandium, yttrium, titanium, zirconium, hafnium, vanadium, niobium, tantalum, chromium, molybdenum, tungsten, manganese, iron, osmium, cobalt, rhodium, iridium, nickel, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium. Among them, it is preferred that M be copper, iron, nickel, cobalt, or manganese, because of a particularly high thermal stability.

In General Formula (I) of the present invention, n represents an integer of 1 or more, m represents an integer of 0 or more, and n+m represents the valence of the metal atom or silicon atom.

The alkoxide compound represented by General Formula (I) can be optically active, but the alkoxide compound in accordance with the present invention is not distinguished by (R) and (S) enantiomers and may be either of them or a mixture including the (R) and (S) enantiomers at a random ratio. The racemic mixture has a low production cost.

General Formula (I-A) below represents a case in which an end donor group in a ligand is coordinated with the metal atom or silicon atom, thereby forming a cyclic structure. The alkoxide compound of the present invention is typically represented by General Formula (I), but is not distinguished from the compound represented by General Formula (I-A) and is conceptually inclusive of both representations.

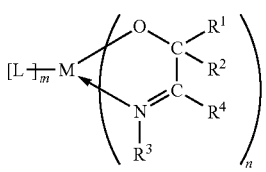
(I-A)

In the formula, $R^1$ to $R^3$ each independently represent hydrogen, a $C_{1-12}$ hydrocarbon group, or a group represented by General Formulas (X-1) to (X-8) below; $R^4$ represents a $C_{1-12}$ hydrocarbon group or a group represented by General Formulas (X-1) to (X-8) below; provided that when $R^1$ is a methyl group, $R^2$ is a methyl group or an ethyl group and $R^4$ is a methyl group, $R^3$ represents hydrogen, a $C_{4-12}$ hydrocarbon group or a group represented by General Formulas (X-1) to (X-8) below; L represents hydrogen, halogen, a hydroxyl group, an amino group, an azi group, a phosphido group, a nitrile group, a carbonyl group, a $C_{1-12}$ hydrocarbon group or a group represented by General Formulas (L-1) to (L-13) below; and M represents a metal atom or a silicon atom, n represents an integer of 1 or more, m represents an integer of 0 or more, and n+m represents the valence of the metal atom or silicon atom.

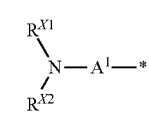 (X-1)

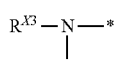 (X-2)

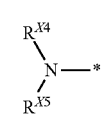 (X-3)

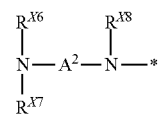 (X-4)

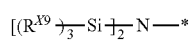 (X-5)

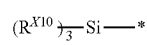 (X-6)

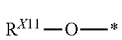 (X-7)

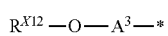 (X-8)

In the formulas, $R^{X1}$ to $R^{X12}$ each independently represent hydrogen or a $C_{1-12}$ hydrocarbon group, and $A^1$ to $A^3$ each represent a $C_{1-6}$ alkanediyl group.

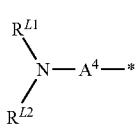 (L-1)

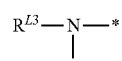 (L-2)

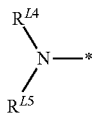 (L-3)

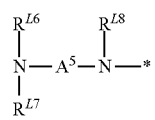 (L-4)

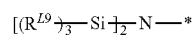 (L-5)

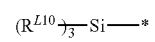 (L-6)

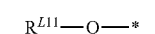 (L-7)

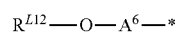 (L-8)

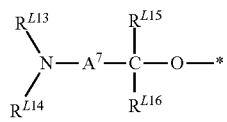 (L-9)

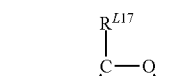 (L-10)

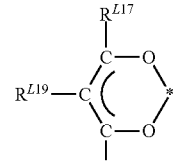 (L-11)

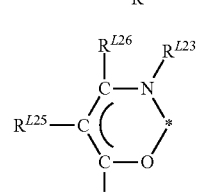 (L-12)

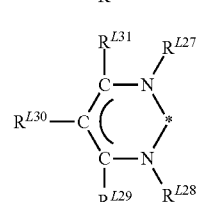 (L-13)

In the formulas, $R^{L1}$ to $R^{L31}$ each independently represent hydrogen or a $C_{1-12}$ hydrocarbon group, and $A^4$ to $A^7$ each represent a $C_{1-6}$ alkanediyl group; and where $R^{L1}$ to $R^{L31}$ are each a $C_{1-12}$ hydrocarbon group, a hydrogen atom in the hydrocarbon group may be substituted with a halogen atom or an amino group.

For example, where M is cobalt, the preferred examples of the alkoxide compound represented by General Formula (I) include compounds represented by Chemical Formulas No. 1 to No. 300 below. In Chemical Formulas No. 1 to No. 300, "Me" represents methyl, "Et" represents ethyl, "iPr" represents isopropyl, "Cp" represents cyclopentadienyl, "MeCp" represents methylcyclopentadienyl, "sCp" represents pentamethylcyclopentadienyl, and "AMD" represents N,N'-diisopropylacetamidinate.

No. 1
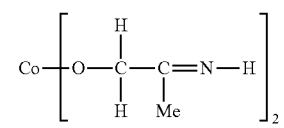

No. 2
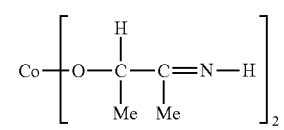

No. 3
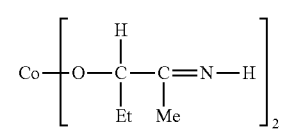

No. 4
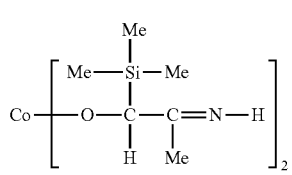

No. 5
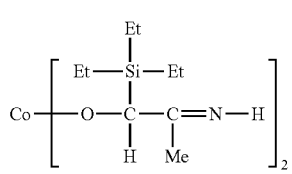

No. 6
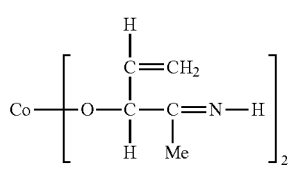

No. 7
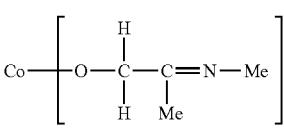

No. 8
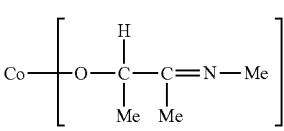

No. 9
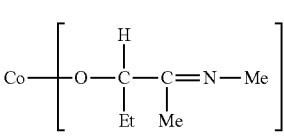

No. 10
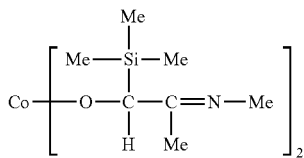

No. 11
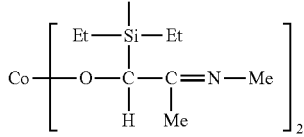

No. 12
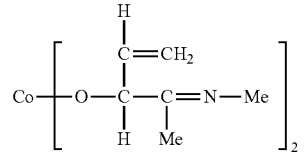

No. 13
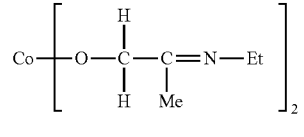

No. 14
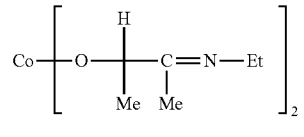

No. 15
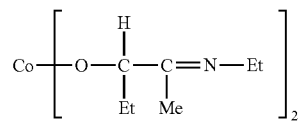

No. 16
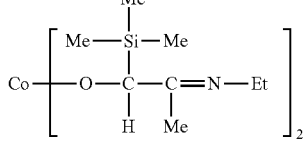

No. 17
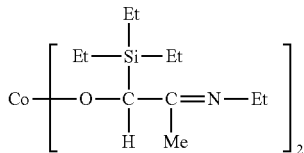

No. 18
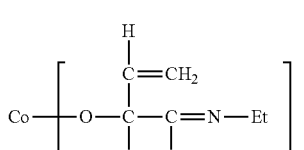

No. 19
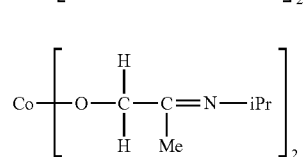

No. 20
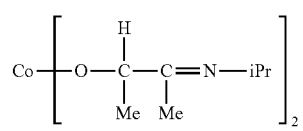
No. 21
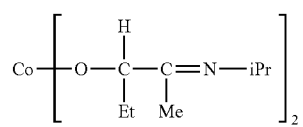
No. 22
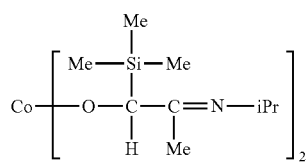
No. 23
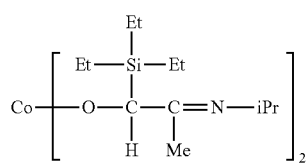
No. 24
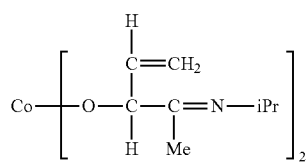
No. 25
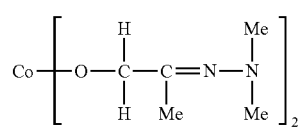
No. 26
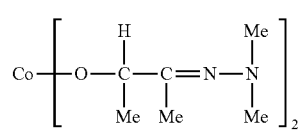
No. 27
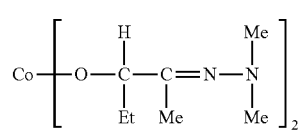
No. 28
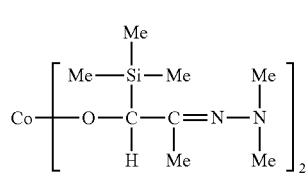
No. 29
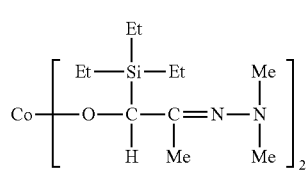
No. 30
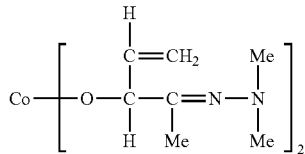
No. 31
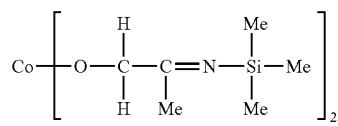
No. 32
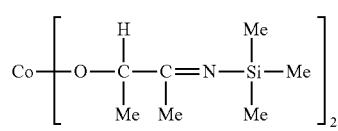
No. 33
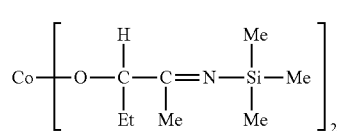
No. 34
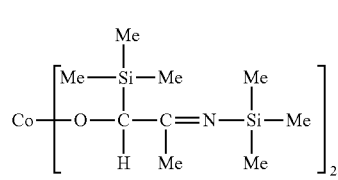
No. 35
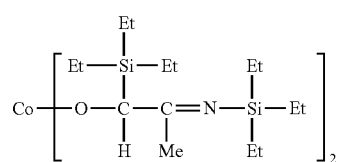
No. 36
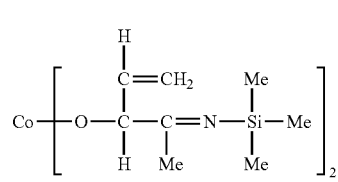
No. 37
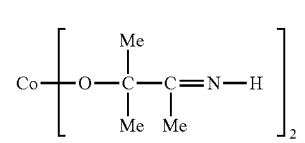
No. 38
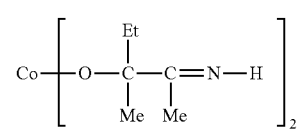
No. 39

-continued

No. 40

$$\text{Co} \left[ \text{O} - \underset{\underset{\text{Me}}{|}}{\overset{\overset{\text{Me}-\text{Si}-\text{Me}}{|}}{\text{C}}} - \underset{\underset{\text{Me}}{|}}{\text{C}} = \text{N} - \text{H} \right]_2$$

No. 41

$$\text{Co} \left[ \text{O} - \underset{\underset{\text{Me}}{|}}{\overset{\overset{\text{Et}-\text{Si}-\text{Et}}{|}}{\text{C}}} - \underset{\underset{\text{Me}}{|}}{\text{C}} = \text{N} - \text{H} \right]_2$$

No. 42

$$\text{Co} \left[ \text{O} - \underset{\underset{\text{Me}}{|}}{\overset{\overset{\text{C}=\text{CH}_2}{|}}{\text{C}}} - \underset{\underset{\text{Me}}{|}}{\text{C}} = \text{N} - \text{H} \right]_2$$

No. 43

$$\text{Co} \left[ \text{O} - \underset{\underset{\text{Et}}{|}}{\overset{\overset{\text{Et}}{|}}{\text{C}}} - \underset{\underset{\text{Me}}{|}}{\text{C}} = \text{N} - \text{Me} \right]_2$$

No. 44

$$\text{Co} \left[ \text{O} - \underset{\underset{\text{Et}}{|}}{\overset{\overset{\text{iPr}}{|}}{\text{C}}} - \underset{\underset{\text{Me}}{|}}{\text{C}} = \text{N} - \text{Me} \right]_2$$

No. 45

$$\text{Co} \left[ \text{O} - \underset{\underset{\text{iPr}}{|}}{\overset{\overset{\text{iPr}}{|}}{\text{C}}} - \underset{\underset{\text{Me}}{|}}{\text{C}} = \text{N} - \text{Me} \right]_2$$

No. 46

$$\text{Co} \left[ \text{O} - \underset{\underset{\text{Me}}{|}}{\overset{\overset{\text{Me}-\text{Si}-\text{Me}}{|}}{\text{C}}} - \underset{\underset{\text{Me}}{|}}{\text{C}} = \text{N} - \text{Me} \right]_2$$

No. 47

$$\text{Co} \left[ \text{O} - \underset{\underset{\text{Me}}{|}}{\overset{\overset{\text{Et}-\text{Si}-\text{Et}}{|}}{\text{C}}} - \underset{\underset{\text{Me}}{|}}{\text{C}} = \text{N} - \text{Me} \right]_2$$

No. 48

$$\text{Co} \left[ \text{O} - \underset{\underset{\text{Me}}{|}}{\overset{\overset{\text{C}=\text{CH}_2}{|}}{\text{C}}} - \underset{\underset{\text{Me}}{|}}{\text{C}} = \text{N} - \text{Me} \right]_2$$

No. 49

$$\text{Co} \left[ \text{O} - \underset{\underset{\text{Et}}{|}}{\overset{\overset{\text{Et}}{|}}{\text{C}}} - \underset{\underset{\text{Me}}{|}}{\text{C}} = \text{N} - \text{Et} \right]_2$$

-continued

No. 50

$$\text{Co} \left[ \text{O} - \underset{\underset{\text{Et}}{|}}{\overset{\overset{\text{iPr}}{|}}{\text{C}}} - \underset{\underset{\text{Me}}{|}}{\text{C}} = \text{N} - \text{Et} \right]_2$$

No. 51

$$\text{Co} \left[ \text{O} - \underset{\underset{\text{iPr}}{|}}{\overset{\overset{\text{iPr}}{|}}{\text{C}}} - \underset{\underset{\text{Me}}{|}}{\text{C}} = \text{N} - \text{Et} \right]_2$$

No. 52

$$\text{Co} \left[ \text{O} - \underset{\underset{\text{Me}}{|}}{\overset{\overset{\text{Me}-\text{Si}-\text{Me}}{|}}{\text{C}}} - \underset{\underset{\text{Me}}{|}}{\text{C}} = \text{N} - \text{Et} \right]_2$$

No. 53

$$\text{Co} \left[ \text{O} - \underset{\underset{\text{Me}}{|}}{\overset{\overset{\text{Et}-\text{Si}-\text{Et}}{|}}{\text{C}}} - \underset{\underset{\text{Me}}{|}}{\text{C}} = \text{N} - \text{Et} \right]_2$$

No. 54

$$\text{Co} \left[ \text{O} - \underset{\underset{\text{Me}}{|}}{\overset{\overset{\text{C}=\text{CH}_2}{|}}{\text{C}}} - \underset{\underset{\text{Me}}{|}}{\text{C}} = \text{N} - \text{Et} \right]_2$$

No. 55

$$\text{Co} \left[ \text{O} - \underset{\underset{\text{Et}}{|}}{\overset{\overset{\text{Et}}{|}}{\text{C}}} - \underset{\underset{\text{Me}}{|}}{\text{C}} = \text{N} - \text{iPr} \right]_2$$

No. 56

$$\text{Co} \left[ \text{O} - \underset{\underset{\text{Et}}{|}}{\overset{\overset{\text{iPr}}{|}}{\text{C}}} - \underset{\underset{\text{Me}}{|}}{\text{C}} = \text{N} - \text{iPr} \right]_2$$

No. 57

$$\text{Co} \left[ \text{O} - \underset{\underset{\text{iPr}}{|}}{\overset{\overset{\text{iPr}}{|}}{\text{C}}} - \underset{\underset{\text{Me}}{|}}{\text{C}} = \text{N} - \text{iPr} \right]_2$$

No. 58

$$\text{Co} \left[ \text{O} - \underset{\underset{\text{Me}}{|}}{\overset{\overset{\text{Me}-\text{Si}-\text{Me}}{|}}{\text{C}}} - \underset{\underset{\text{Me}}{|}}{\text{C}} = \text{N} - \text{iPr} \right]_2$$

No. 59

$$\text{Co} \left[ \text{O} - \underset{\underset{\text{Me}}{|}}{\overset{\overset{\text{Et}-\text{Si}-\text{Et}}{|}}{\text{C}}} - \underset{\underset{\text{Me}}{|}}{\text{C}} = \text{N} - \text{iPr} \right]_2$$

No. 60
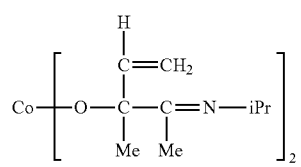
No. 61
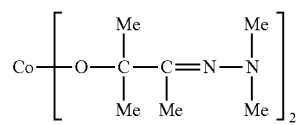
No. 62
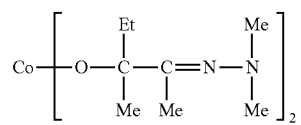
No. 63
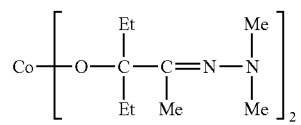
No. 64
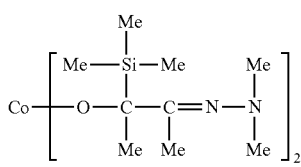
No. 65
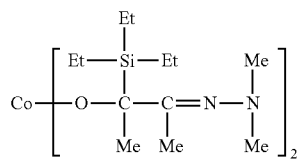
No. 66
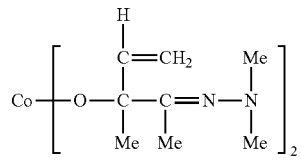
No. 67
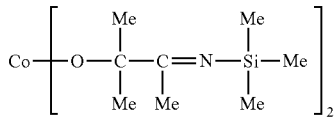
No. 68
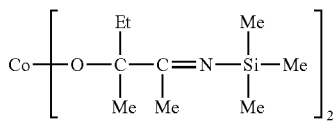
No. 69
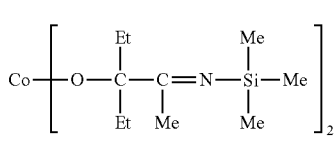
No. 70
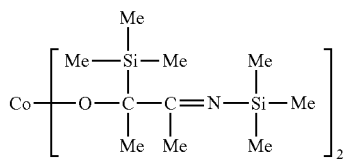
No. 71
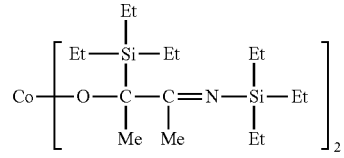
No. 72
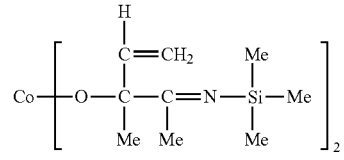
No. 73
No. 74
No. 75
No. 76
No. 77
No. 78
No. 79
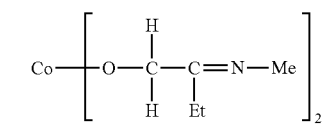

-continued

No. 80

Co—[—O—C(H)(Me)—C(Et)=N—Me]₂

No. 81

Co—[—O—C(H)(Et)—C(Et)=N—Me]₂

No. 82

Co—[—O—C(SiMe₃)(H)—C(Et)=N—Me]₂

No. 83

Co—[—O—C(SiEt₃)(H)—C(Et)=N—Me]₂

No. 84

Co—[—O—C(CH=CH₂)(H)—C(Et)=N—Me]₂

No. 85

Co—[—O—C(H)(H)—C(Et)=N—Et]₂

No. 86

Co—[—O—C(H)(Me)—C(Et)=N—Et]₂

No. 87

Co—[—O—C(H)(Et)—C(Et)=N—Et]₂

No. 88

Co—[—O—C(SiMe₃)(H)—C(Et)=N—Et]₂

No. 89

Co—[—O—C(SiEt₃)(H)—C(Et)=N—Et]₂

-continued

No. 90

Co—[—O—C(CH=CH₂)(H)—C(Et)=N—Et]₂

No. 91

Co—[—O—C(H)(H)—C(Et)=N—iPr]₂

No. 92

Co—[—O—C(H)(Me)—C(Et)=N—iPr]₂

No. 93

Co—[—O—C(H)(Et)—C(Et)=N—iPr]₂

No. 94

Co—[—O—C(SiMe₃)(H)—C(Et)=N—iPr]₂

No. 95

Co—[—O—C(SiEt₃)(H)—C(Et)=N—iPr]₂

No. 96

Co—[—O—C(CH=CH₂)(H)—C(Et)=N—iPr]₂

No. 97

Co—[—O—C(H)(H)—C(Et)=N—N(Me)(Me)]₂

No. 98

Co—[—O—C(H)(Me)—C(Et)=N—N(Me)(Me)]₂

No. 99

Co—[—O—C(H)(Et)—C(Et)=N—N(Me)(Me)]₂

-continued

No. 100

$$\text{Co}\left[\text{O}-\underset{\underset{\text{H}}{|}}{\overset{\overset{\text{Me}-\text{Si}-\text{Me}}{|}}{\text{C}}}-\underset{\underset{\text{Et}}{|}}{\text{C}}=\text{N}-\underset{\underset{\text{Me}}{|}}{\overset{\text{Me}}{\text{N}}}\right]_2$$

No. 101

$$\text{Co}\left[\text{O}-\underset{\underset{\text{H}}{|}}{\overset{\overset{\text{Et}-\text{Si}-\text{Et}}{|}}{\text{C}}}-\underset{\underset{\text{Et}}{|}}{\text{C}}=\text{N}-\underset{\underset{\text{Me}}{|}}{\overset{\text{Me}}{\text{N}}}\right]_2$$

No. 102

$$\text{Co}\left[\text{O}-\underset{\underset{\text{H}}{|}}{\overset{\overset{\text{H}}{\underset{|}{\text{C}=\text{CH}_2}}}{\text{C}}}-\underset{\underset{\text{Et}}{|}}{\text{C}}=\text{N}-\underset{\underset{\text{Me}}{|}}{\overset{\text{Me}}{\text{N}}}\right]_2$$

No. 103

$$\text{Co}\left[\text{O}-\underset{\underset{\text{H}}{|}}{\overset{\overset{\text{H}}{|}}{\text{C}}}-\underset{\underset{\text{Et}}{|}}{\text{C}}=\text{N}-\underset{\underset{\text{Me}}{|}}{\overset{\text{Me}}{\text{Si}}}-\text{Me}\right]_2$$

No. 104

$$\text{Co}\left[\text{O}-\underset{\underset{\text{Me}}{|}}{\overset{\overset{\text{H}}{|}}{\text{C}}}-\underset{\underset{\text{Et}}{|}}{\text{C}}=\text{N}-\underset{\underset{\text{Me}}{|}}{\overset{\text{Me}}{\text{Si}}}-\text{Me}\right]_2$$

No. 105

$$\text{Co}\left[\text{O}-\underset{\underset{\text{Et}}{|}}{\overset{\overset{\text{H}}{|}}{\text{C}}}-\underset{\underset{\text{Et}}{|}}{\text{C}}=\text{N}-\underset{\underset{\text{Me}}{|}}{\overset{\text{Me}}{\text{Si}}}-\text{Me}\right]_2$$

No. 106

$$\text{Co}\left[\text{O}-\underset{\underset{\text{H}}{|}}{\overset{\overset{\text{Me}-\text{Si}-\text{Me}}{|}}{\text{C}}}-\underset{\underset{\text{Et}}{|}}{\text{C}}=\text{N}-\underset{\underset{\text{Me}}{|}}{\overset{\text{Me}}{\text{Si}}}-\text{Me}\right]_2$$

No. 107

$$\text{Co}\left[\text{O}-\underset{\underset{\text{H}}{|}}{\overset{\overset{\text{Et}-\text{Si}-\text{Et}}{|}}{\text{C}}}-\underset{\underset{\text{Et}}{|}}{\text{C}}=\text{N}-\underset{\underset{\text{Et}}{|}}{\overset{\text{Et}}{\text{Si}}}-\text{Et}\right]_2$$

No. 108

$$\text{Co}\left[\text{O}-\underset{\underset{\text{H}}{|}}{\overset{\overset{\text{H}}{\underset{|}{\text{C}=\text{CH}_2}}}{\text{C}}}-\underset{\underset{\text{Et}}{|}}{\text{C}}=\text{N}-\underset{\underset{\text{Me}}{|}}{\overset{\text{Me}}{\text{Si}}}-\text{Me}\right]_2$$

No. 109

$$\text{Co}\left[\text{O}-\underset{\underset{\text{Me}}{|}}{\overset{\overset{\text{Me}}{|}}{\text{C}}}-\underset{\underset{\text{Et}}{|}}{\text{C}}=\text{N}-\text{H}\right]_2$$

No. 110

$$\text{Co}\left[\text{O}-\underset{\underset{\text{Me}}{|}}{\overset{\overset{\text{Et}}{|}}{\text{C}}}-\underset{\underset{\text{Et}}{|}}{\text{C}}=\text{N}-\text{H}\right]_2$$

No. 111

$$\text{Co}\left[\text{O}-\underset{\underset{\text{Et}}{|}}{\overset{\overset{\text{Et}}{|}}{\text{C}}}-\underset{\underset{\text{Et}}{|}}{\text{C}}=\text{N}-\text{H}\right]_2$$

No. 112

$$\text{Co}\left[\text{O}-\underset{\underset{\text{Me}}{|}}{\overset{\overset{\text{Me}-\text{Si}-\text{Me}}{|}}{\text{C}}}-\underset{\underset{\text{Et}}{|}}{\text{C}}=\text{N}-\text{H}\right]_2$$

No. 113

$$\text{Co}\left[\text{O}-\underset{\underset{\text{Me}}{|}}{\overset{\overset{\text{Et}-\text{Si}-\text{Et}}{|}}{\text{C}}}-\underset{\underset{\text{Et}}{|}}{\text{C}}=\text{N}-\text{H}\right]_2$$

No. 114

$$\text{Co}\left[\text{O}-\underset{\underset{\text{Me}}{|}}{\overset{\overset{\text{H}}{\underset{|}{\text{C}=\text{CH}_2}}}{\text{C}}}-\underset{\underset{\text{Et}}{|}}{\text{C}}=\text{N}-\text{H}\right]_2$$

No. 115

$$\text{Co}\left[\text{O}-\underset{\underset{\text{Et}}{|}}{\overset{\overset{\text{Et}}{|}}{\text{C}}}-\underset{\underset{\text{Et}}{|}}{\text{C}}=\text{N}-\text{Me}\right]_2$$

No. 116

$$\text{Co}\left[\text{O}-\underset{\underset{\text{Et}}{|}}{\overset{\overset{\text{iPr}}{|}}{\text{C}}}-\underset{\underset{\text{Et}}{|}}{\text{C}}=\text{N}-\text{Me}\right]_2$$

No. 117

$$\text{Co}\left[\text{O}-\underset{\underset{\text{iPr}}{|}}{\overset{\overset{\text{iPr}}{|}}{\text{C}}}-\underset{\underset{\text{Et}}{|}}{\text{C}}=\text{N}-\text{Me}\right]_2$$

No. 118

$$\text{Co}\left[\text{O}-\underset{\underset{\text{Me}}{|}}{\overset{\overset{\text{Me}-\text{Si}-\text{Me}}{|}}{\text{C}}}-\underset{\underset{\text{Et}}{|}}{\text{C}}=\text{N}-\text{Me}\right]_2$$

No. 119

$$\text{Co}\left[\text{O}-\underset{\underset{\text{Me}}{|}}{\overset{\overset{\text{Et}-\text{Si}-\text{Et}}{|}}{\text{C}}}-\underset{\underset{\text{Et}}{|}}{\text{C}}=\text{N}-\text{Me}\right]_2$$

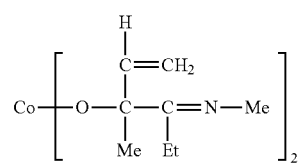
No. 120
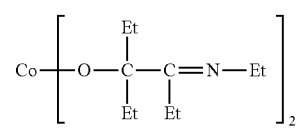
No. 121
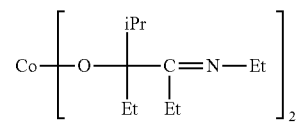
No. 122
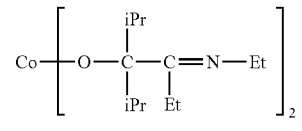
No. 123
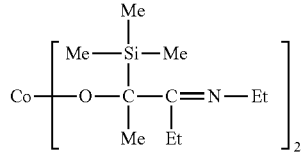
No. 124
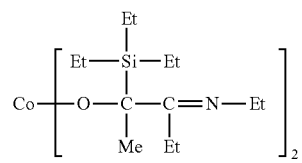
No. 125
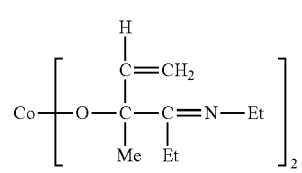
No. 126
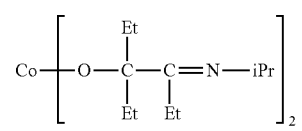
No. 127
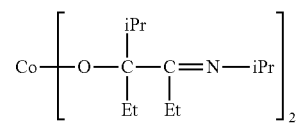
No. 128
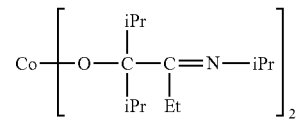
No. 129
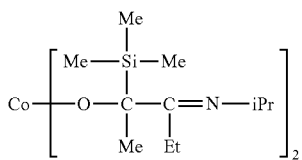
No. 130
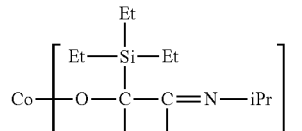
No. 131
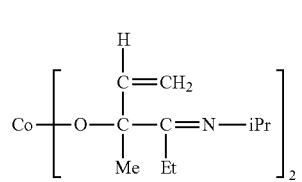
No. 132
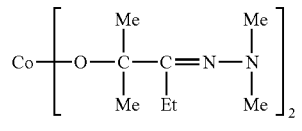
No. 133
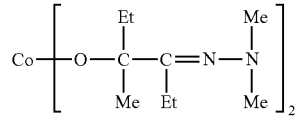
No. 134
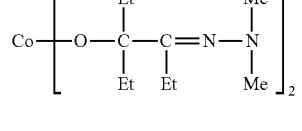
No. 135
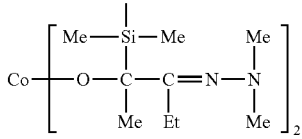
No. 136
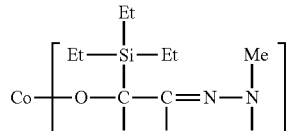
No. 137
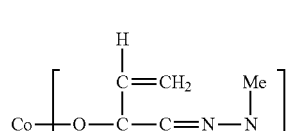
No. 138
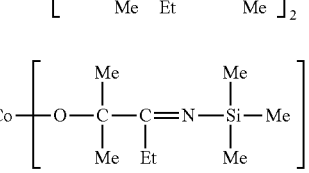
No. 139

No. 140
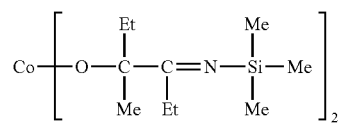
No. 141
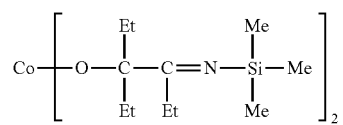
No. 142
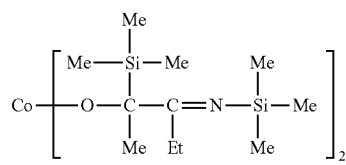
No. 143
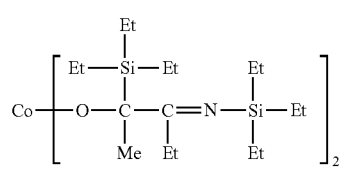
No. 144
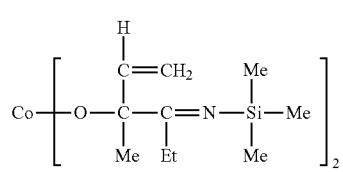
No. 145
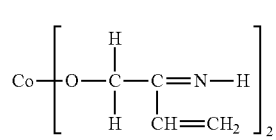
No. 146
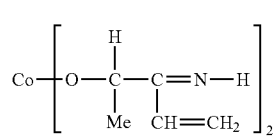
No. 147
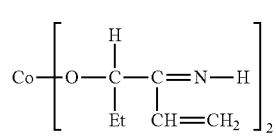
No. 148
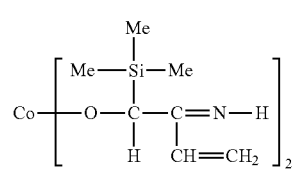
No. 149
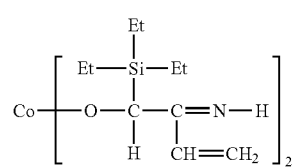
No. 150
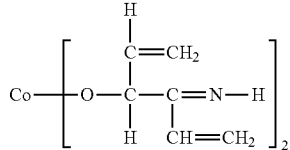
No. 151
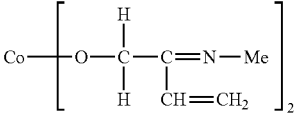
No. 152
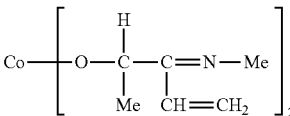
No. 153
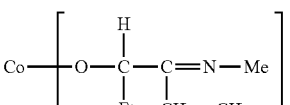
No. 154
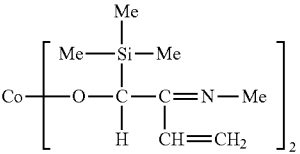
No. 155
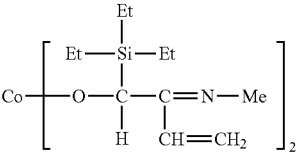
No. 156
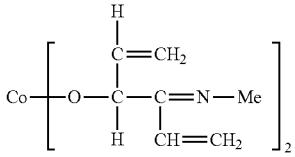
No. 157
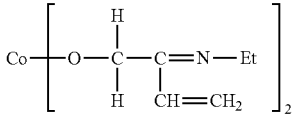
No. 158
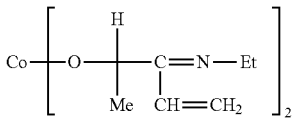
No. 159
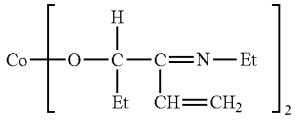

No. 160

$$\text{Co}\left[-\text{O}-\underset{\underset{H}{|}}{\overset{\overset{Me}{|}}{\underset{|}{\text{Si}}}-Me}{\overset{|}{\text{C}}}-\underset{\underset{CH=CH_2}{|}}{\text{C}}=N-Et\right]_2$$

No. 161

$$\text{Co}\left[-\text{O}-\underset{\underset{H}{|}}{\overset{\overset{Et}{|}}{\underset{|}{\text{Si}}}-Et}{\overset{|}{\text{C}}}-\underset{\underset{CH=CH_2}{|}}{\text{C}}=N-Et\right]_2$$

No. 162

$$\text{Co}\left[-\text{O}-\underset{\underset{H}{|}}{\overset{\overset{H}{|}}{\underset{|}{\text{C}}}=CH_2}{\overset{|}{\text{C}}}-\underset{\underset{CH=CH_2}{|}}{\text{C}}=N-Et\right]_2$$

No. 163

$$\text{Co}\left[-\text{O}-\underset{\underset{H}{|}}{\overset{\overset{H}{|}}{\text{C}}}-\underset{\underset{CH=CH_2}{|}}{\text{C}}=N-iPr\right]_2$$

No. 164

$$\text{Co}\left[-\text{O}-\underset{\underset{Me}{|}}{\overset{\overset{H}{|}}{\text{C}}}-\underset{\underset{CH=CH_2}{|}}{\text{C}}=N-iPr\right]_2$$

No. 165

$$\text{Co}\left[-\text{O}-\underset{\underset{Et}{|}}{\overset{\overset{H}{|}}{\text{C}}}-\underset{\underset{CH=CH_2}{|}}{\text{C}}=N-iPr\right]_2$$

No. 166

$$\text{Co}\left[-\text{O}-\underset{\underset{H}{|}}{\overset{\overset{Me}{|}}{\underset{|}{\text{Si}}}-Me}{\overset{|}{\text{C}}}-\underset{\underset{CH=CH_2}{|}}{\text{C}}=N-iPr\right]_2$$

No. 167

$$\text{Co}\left[-\text{O}-\underset{\underset{H}{|}}{\overset{\overset{Et}{|}}{\underset{|}{\text{Si}}}-Et}{\overset{|}{\text{C}}}-\underset{\underset{CH=CH_2}{|}}{\text{C}}=N-iPr\right]_2$$

No. 168

$$\text{Co}\left[-\text{O}-\underset{\underset{H}{|}}{\overset{\overset{H}{|}}{\underset{|}{\text{C}}}=CH_2}{\overset{|}{\text{C}}}-\underset{\underset{CH=CH_2}{|}}{\text{C}}=N-iPr\right]_2$$

No. 169

$$\text{Co}\left[-\text{O}-\underset{\underset{Me}{|}}{\overset{\overset{Me}{|}}{\text{C}}}-\underset{\underset{CH=CH_2}{|}}{\text{C}}=N-H\right]_2$$

No. 170

$$\text{Co}\left[-\text{O}-\underset{\underset{Me}{|}}{\overset{\overset{Et}{|}}{\text{C}}}-\underset{\underset{CH=CH_2}{|}}{\text{C}}=N-H\right]_2$$

No. 171

$$\text{Co}\left[-\text{O}-\underset{\underset{Et}{|}}{\overset{\overset{Et}{|}}{\text{C}}}-\underset{\underset{CH=CH_2}{|}}{\text{C}}=N-H\right]_2$$

No. 172

$$\text{Co}\left[-\text{O}-\underset{\underset{Me}{|}}{\overset{\overset{Me}{|}}{\underset{|}{\text{Si}}}-Me}{\overset{|}{\text{C}}}-\underset{\underset{CH=CH_2}{|}}{\text{C}}=N-H\right]_2$$

No. 173

$$\text{Co}\left[-\text{O}-\underset{\underset{Me}{|}}{\overset{\overset{Et}{|}}{\underset{|}{\text{Si}}}-Et}{\overset{|}{\text{C}}}-\underset{\underset{CH=CH_2}{|}}{\text{C}}=N-H\right]_2$$

No. 174

$$\text{Co}\left[-\text{O}-\underset{\underset{Me}{|}}{\overset{\overset{H}{|}}{\underset{|}{\text{C}}}=CH_2}{\overset{|}{\text{C}}}-\underset{\underset{CH=CH_2}{|}}{\text{C}}=N-H\right]_2$$

No. 175

$$\text{Co}\left[-\text{O}-\underset{\underset{Et}{|}}{\overset{\overset{Et}{|}}{\text{C}}}-\underset{\underset{CH=CH_2}{|}}{\text{C}}=N-Me\right]_2$$

No. 176

$$\text{Co}\left[-\text{O}-\underset{\underset{Et}{|}}{\overset{\overset{iPr}{|}}{\text{C}}}-\underset{\underset{CH=CH_2}{|}}{\text{C}}=N-Me\right]_2$$

No. 177

$$\text{Co}\left[-\text{O}-\underset{\underset{iPr}{|}}{\overset{\overset{iPr}{|}}{\text{C}}}-\underset{\underset{CH=CH_2}{|}}{\text{C}}=N-Me\right]_2$$

No. 178

$$\text{Co}\left[-\text{O}-\underset{\underset{Me}{|}}{\overset{\overset{Me}{|}}{\underset{|}{\text{Si}}}-Me}{\overset{|}{\text{C}}}-\underset{\underset{CH=CH_2}{|}}{\text{C}}=N-Me\right]_2$$

No. 179

$$\text{Co}\left[-\text{O}-\underset{\underset{Me}{|}}{\overset{\overset{Et}{|}}{\underset{|}{\text{Si}}}-Et}{\overset{|}{\text{C}}}-\underset{\underset{CH=CH_2}{|}}{\text{C}}=N-Me\right]_2$$

Structures No. 180–199

No. 180: Co—[O—C(Me)(CH=CH₂)—C(CH=CH₂)=N—Me]₂

No. 181: Co—[O—C(Et)(Et)—C(CH=CH₂)=N—Et]₂

No. 182: Co—[O—C(iPr)(Et)—C(CH=CH₂)=N—Et]₂

No. 183: Co—[O—C(iPr)(iPr)—C(CH=CH₂)=N—Et]₂

No. 184: Co—[O—C(SiMe₃)(Me)—C(CH=CH₂)=N—Et]₂

No. 185: Co—[O—C(SiEt₃)(Me)—C(CH=CH₂)=N—Et]₂

No. 186: Co—[O—C(Me)(CH=CH₂)—C(CH=CH₂)=N—Et]₂

No. 187: Co—[O—C(Et)(Et)—C(CH=CH₂)=N—iPr]₂

No. 188: Co—[O—C(iPr)(Et)—C(CH=CH₂)=N—iPr]₂

No. 189: Co—[O—C(iPr)(iPr)—C(CH=CH₂)=N—iPr]₂

No. 190: Co—[O—C(SiMe₃)(Me)—C(CH=CH₂)=N—iPr]₂

No. 191: Co—[O—C(SiEt₃)(Me)—C(CH=CH₂)=N—iPr]₂

No. 192: Co—[O—C(Me)(CH=CH₂)—C(CH=CH₂)=N—iPr]₂

No. 193: Co—[O—C(H)(H)—C(Si(Me)₃)=N—H]₂

No. 194: Co—[O—C(Me)(H)—C(Si(Me)₃)=N—H]₂

No. 195: Co—[O—C(Et)(H)—C(Si(Me)₃)=N—H]₂

No. 196: Co—[O—C(SiMe₃)(H)—C(Si(Me)₃)=N—H]₂

No. 197: Co—[O—C(SiEt₃)(H)—C(Si(Me)₃)=N—H]₂

No. 198: Co—[O—C(H)(H)—C(Si(Me)₃)=N—H, with C=CH₂ branch]₂

No. 199: Co—[O—C(H)(H)—C(Si(Me)₃)=N—Me]₂

-continued

No. 200

$$\text{Co}\left[-\text{O}-\underset{\underset{\text{Si(Me)}_3}{|}}{\overset{\overset{\text{H}}{|}}{\text{C}}}-\text{C}=\text{N}-\text{Me}\right]_2$$

No. 201

$$\text{Co}\left[-\text{O}-\underset{\underset{\text{Si(Me)}_3}{|}}{\overset{\overset{\text{H}}{|}}{\text{C}}}-\text{C}=\text{N}-\text{Me}\right]_2$$

No. 202

$$\text{Co}\left[-\text{O}-\underset{\underset{\text{Si(Me)}_3}{|}}{\overset{\overset{\text{Me}-\text{Si}-\text{Me}}{|}}{\text{C}}}-\text{C}=\text{N}-\text{Me}\right]_2$$

No. 203

$$\text{Co}\left[-\text{O}-\underset{\underset{\text{Si(Me)}_3}{|}}{\overset{\overset{\text{Et}-\text{Si}-\text{Et}}{|}}{\text{C}}}-\text{C}=\text{N}-\text{Me}\right]_2$$

No. 204

$$\text{Co}\left[-\text{O}-\underset{\underset{\text{Si(Me)}_3}{|}}{\overset{\overset{\text{C}=\text{CH}_2}{|}}{\text{C}}}-\text{C}=\text{N}-\text{Me}\right]_2$$

No. 205

$$\text{Co}\left[-\text{O}-\underset{\underset{\text{Si(Me)}_3}{|}}{\overset{\overset{\text{H}}{|}}{\text{C}}}-\text{C}=\text{N}-\text{Et}\right]_2$$

No. 206

$$\text{Co}\left[-\text{O}-\underset{\underset{\text{Si(Me)}_3}{|}}{\overset{\overset{\text{H}}{|}}{\text{C}}}-\text{C}=\text{N}-\text{Et}\right]_2$$

No. 207

$$\text{Co}\left[-\text{O}-\underset{\underset{\text{Si(Me)}_3}{|}}{\overset{\overset{\text{H}}{|}}{\text{C}}}-\text{C}=\text{N}-\text{Et}\right]_2$$

No. 208

$$\text{Co}\left[-\text{O}-\underset{\underset{\text{Si(Me)}_3}{|}}{\overset{\overset{\text{Me}-\text{Si}-\text{Me}}{|}}{\text{C}}}-\text{C}=\text{N}-\text{Et}\right]_2$$

No. 209

$$\text{Co}\left[-\text{O}-\underset{\underset{\text{Si(Me)}_3}{|}}{\overset{\overset{\text{Et}-\text{Si}-\text{Et}}{|}}{\text{C}}}-\text{C}=\text{N}-\text{Et}\right]_2$$

-continued

No. 210

$$\text{Co}\left[-\text{O}-\underset{\underset{\text{Si(Me)}_3}{|}}{\overset{\overset{\text{C}=\text{CH}_2}{|}}{\text{C}}}-\text{C}=\text{N}-\text{Et}\right]_2$$

No. 211

$$\text{Co}\left[-\text{O}-\underset{\underset{\text{Si(Me)}_3}{|}}{\overset{\overset{\text{H}}{|}}{\text{C}}}-\text{C}=\text{N}-\text{iPr}\right]_2$$

No. 212

$$\text{Co}\left[-\text{O}-\underset{\underset{\text{Si(Me)}_3}{|}}{\overset{\overset{\text{H}}{|}}{\text{C}}}-\text{C}=\text{N}-\text{iPr}\right]_2$$

No. 213

$$\text{Co}\left[-\text{O}-\underset{\underset{\text{Si(Me)}_3}{|}}{\overset{\overset{\text{H}}{|}}{\text{C}}}-\text{C}=\text{N}-\text{iPr}\right]_2$$

No. 214

$$\text{Co}\left[-\text{O}-\underset{\underset{\text{Si(Me)}_3}{|}}{\overset{\overset{\text{Me}-\text{Si}-\text{Me}}{|}}{\text{C}}}-\text{C}=\text{N}-\text{iPr}\right]_2$$

No. 215

$$\text{Co}\left[-\text{O}-\underset{\underset{\text{Si(Me)}_3}{|}}{\overset{\overset{\text{Et}-\text{Si}-\text{Et}}{|}}{\text{C}}}-\text{C}=\text{N}-\text{iPr}\right]_2$$

No. 216

$$\text{Co}\left[-\text{O}-\underset{\underset{\text{Si(Me)}_3}{|}}{\overset{\overset{\text{C}=\text{CH}_2}{|}}{\text{C}}}-\text{C}=\text{N}-\text{iPr}\right]_2$$

No. 217

$$\text{Co}\left[-\text{O}-\underset{\underset{\text{Si(Me)}_3}{|}}{\overset{\overset{\text{Me}}{|}}{\text{C}}}-\text{C}=\text{N}-\text{H}\right]_2$$

No. 218

$$\text{Co}\left[-\text{O}-\underset{\underset{\text{Si(Me)}_3}{|}}{\overset{\overset{\text{Et}}{|}}{\text{C}}}-\text{C}=\text{N}-\text{H}\right]_2$$

No. 219

$$\text{Co}\left[-\text{O}-\underset{\underset{\text{Si(Me)}_3}{|}}{\overset{\overset{\text{Et}}{|}}{\text{C}}}-\text{C}=\text{N}-\text{H}\right]_2$$

No. 220

$$Co \left[ O - \underset{Me}{\underset{|}{C}} - \underset{Si(Me)_3}{\underset{|}{C}} = N - H \right]_2$$

No. 221

$$Co \left[ O - \underset{Me}{\underset{|}{C}} \overset{Et-Si-Et}{\underset{|}{\underset{Me}{|}}} - \underset{Si(Me)_3}{\underset{|}{C}} = N - H \right]_2$$

No. 222

$$Co \left[ O - \underset{Me}{\underset{|}{C}} \overset{H}{\underset{C=CH_2}{|}} - \underset{Si(Me)_3}{\underset{|}{C}} = N - H \right]_2$$

No. 223

$$Co \left[ O - \underset{Et}{\underset{|}{C}} - \underset{Si(Me)_3}{\underset{|}{C}} = N - Me \right]_2$$

No. 224

$$Co \left[ O - \underset{Et}{\underset{|}{C}} - \underset{Si(Me)_3}{\underset{|}{C}} = N - Me \right]_2$$

No. 225

$$Co \left[ O - \underset{iPr}{\underset{|}{C}} - \underset{Si(Me)_3}{\underset{|}{C}} = N - Me \right]_2$$

No. 226

$$Co \left[ O - \underset{Me}{\underset{|}{C}} - \underset{Si(Me)_3}{\underset{|}{C}} = N - Me \right]_2$$

No. 227

$$Co \left[ O - \underset{Me}{\underset{|}{C}} \overset{Et-Si-Et}{\underset{|}{\underset{Me}{|}}} - \underset{Si(Et)_3}{\underset{|}{C}} = N - Me \right]_2$$

No. 228

$$Co \left[ O - \underset{Me}{\underset{|}{C}} \overset{H}{\underset{C=CH_2}{|}} - \underset{Si(Me)_3}{\underset{|}{C}} = N - Me \right]_2$$

No. 229

$$Co \left[ O - \underset{Et}{\underset{|}{C}} - \underset{Si(Me)_3}{\underset{|}{C}} = N - Et \right]_2$$

No. 230

$$Co \left[ O - \underset{Et}{\underset{|}{C}} - \underset{Si(Me)_3}{\underset{|}{C}} = N - Et \right]_2$$

No. 231

$$Co \left[ O - \underset{iPr}{\underset{|}{C}} - \underset{Si(Me)_3}{\underset{|}{C}} = N - Et \right]_2$$

No. 232

$$Co \left[ O - \underset{Me}{\underset{|}{C}} - \underset{Si(Me)_3}{\underset{|}{C}} = N - Et \right]_2$$

No. 233

$$Co \left[ O - \underset{Me}{\underset{|}{C}} \overset{Et-Si-Et}{\underset{|}{\underset{Me}{|}}} - \underset{Si(Me)_3}{\underset{|}{C}} = N - Et \right]_2$$

No. 234

$$Co \left[ O - \underset{Me}{\underset{|}{C}} \overset{H}{\underset{C=CH_2}{|}} - \underset{Si(Me)_3}{\underset{|}{C}} = N - Et \right]_2$$

No. 235

$$Co \left[ O - \underset{Et}{\underset{|}{C}} - \underset{Si(Me)_3}{\underset{|}{C}} = N - iPr \right]_2$$

No. 236

$$Co \left[ O - \underset{Et}{\underset{|}{C}} - \underset{Si(Me)_3}{\underset{|}{C}} = N - iPr \right]_2$$

No. 237

$$Co \left[ O - \underset{iPr}{\underset{|}{C}} - \underset{Si(Me)_3}{\underset{|}{C}} = N - iPr \right]_2$$

No. 238

$$Co \left[ O - \underset{Me}{\underset{|}{C}} - \underset{Si(Me)_3}{\underset{|}{C}} = N - iPr \right]_2$$

No. 239

$$Co \left[ O - \underset{Me}{\underset{|}{C}} \overset{Et-Si-Et}{\underset{|}{\underset{Me}{|}}} - \underset{Si(Me)_3}{\underset{|}{C}} = N - iPr \right]_2$$

No. 240
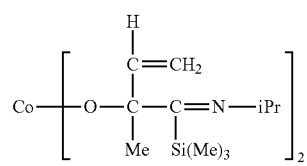
No. 241
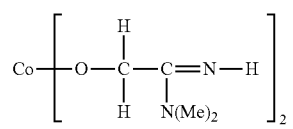
No. 242
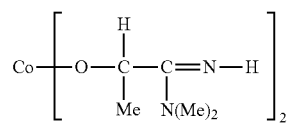
No. 243
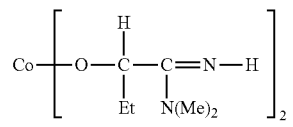
No. 244
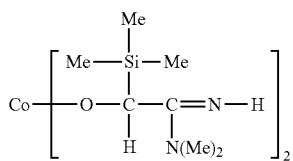
No. 245
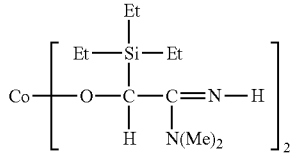
No. 246
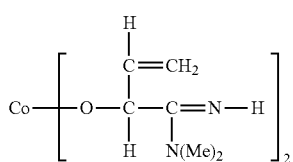
No. 247
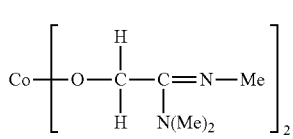
No. 248
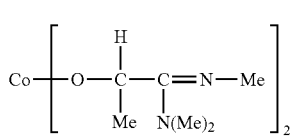
No. 249
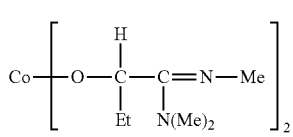
No. 250
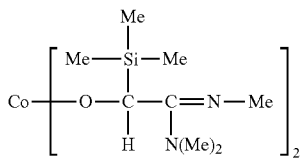
No. 251
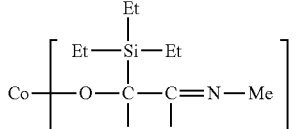
No. 252
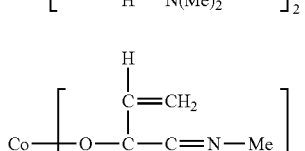
No. 253
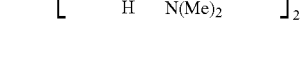
No. 254
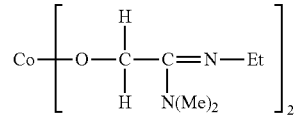
No. 255
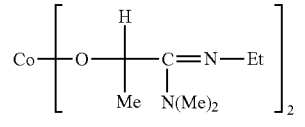
No. 256
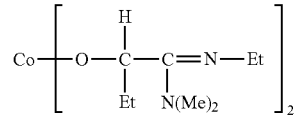
No. 257
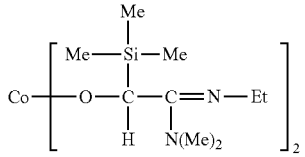
No. 258
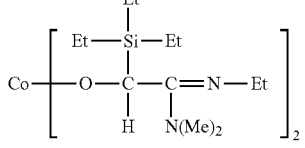
No. 259
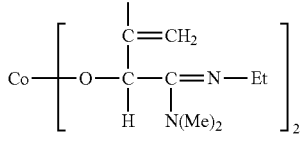

-continued

No. 260

$$\text{Co}\left[\text{O}-\underset{\underset{\text{Me}}{|}}{\overset{\overset{\text{H}}{|}}{\text{C}}}-\underset{\underset{\text{N(Me)}_2}{|}}{\text{C}}=\text{N}-\text{iPr}\right]_2$$

No. 261

$$\text{Co}\left[\text{O}-\underset{\underset{\text{Et}}{|}}{\overset{\overset{\text{H}}{|}}{\text{C}}}-\underset{\underset{\text{N(Me)}_2}{|}}{\text{C}}=\text{N}-\text{iPr}\right]_2$$

No. 262

$$\text{Co}\left[\text{O}-\underset{\underset{\text{H}}{|}}{\overset{\overset{\text{Me-Si-Me}}{\overset{|}{\text{Me}}}}{\text{C}}}-\underset{\underset{\text{N(Me)}_2}{|}}{\text{C}}=\text{N}-\text{iPr}\right]_2$$

No. 263

$$\text{Co}\left[\text{O}-\underset{\underset{\text{H}}{|}}{\overset{\overset{\text{Et-Si-Et}}{\overset{|}{\text{Et}}}}{\text{C}}}-\underset{\underset{\text{N(Me)}_2}{|}}{\text{C}}=\text{N}-\text{iPr}\right]_2$$

No. 264

$$\text{Co}\left[\text{O}-\underset{\underset{\text{H}}{|}}{\overset{\overset{\text{C}=\text{CH}_2}{\overset{|}{\text{H}}}}{\text{C}}}-\underset{\underset{\text{N(Me)}_2}{|}}{\text{C}}=\text{N}-\text{iPr}\right]_2$$

No. 265

$$\text{Co}\left[\text{O}-\underset{\underset{\text{Me}}{|}}{\overset{\overset{\text{Me}}{|}}{\text{C}}}-\underset{\underset{\text{N(Me)}_2}{|}}{\text{C}}=\text{N}-\text{H}\right]_2$$

No. 266

$$\text{Co}\left[\text{O}-\underset{\underset{\text{Me}}{|}}{\overset{\overset{\text{Et}}{|}}{\text{C}}}-\underset{\underset{\text{N(Me)}_2}{|}}{\text{C}}=\text{N}-\text{H}\right]_2$$

No. 267

$$\text{Co}\left[\text{O}-\underset{\underset{\text{Et}}{|}}{\overset{\overset{\text{Et}}{|}}{\text{C}}}-\underset{\underset{\text{N(Me)}_2}{|}}{\text{C}}=\text{N}-\text{H}\right]_2$$

No. 268

$$\text{Co}\left[\text{O}-\underset{\underset{\text{Me}}{|}}{\overset{\overset{\text{Me-Si-Me}}{\overset{|}{\text{Me}}}}{\text{C}}}-\underset{\underset{\text{N(Me)}_2}{|}}{\text{C}}=\text{N}-\text{H}\right]_2$$

No. 269

$$\text{Co}\left[\text{O}-\underset{\underset{\text{Me}}{|}}{\overset{\overset{\text{Et-Si-Et}}{\overset{|}{\text{Et}}}}{\text{C}}}-\underset{\underset{\text{N(Me)}_2}{|}}{\text{C}}=\text{N}-\text{H}\right]_2$$

-continued

No. 270

$$\text{Co}\left[\text{O}-\underset{\underset{\text{Me}}{|}}{\overset{\overset{\text{C}=\text{CH}_2}{\overset{|}{\text{H}}}}{\text{C}}}-\underset{\underset{\text{N(Me)}_2}{|}}{\text{C}}=\text{N}-\text{H}\right]_2$$

No. 271

$$\text{Co}\left[\text{O}-\underset{\underset{\text{Et}}{|}}{\overset{\overset{\text{Et}}{|}}{\text{C}}}-\underset{\underset{\text{N(Me)}_2}{|}}{\text{C}}=\text{N}-\text{Me}\right]_2$$

No. 272

$$\text{Co}\left[\text{O}-\underset{\underset{\text{Et}}{|}}{\overset{\overset{\text{iPr}}{|}}{\text{C}}}-\underset{\underset{\text{N(Me)}_2}{|}}{\text{C}}=\text{N}-\text{Me}\right]_2$$

No. 273

$$\text{Co}\left[\text{O}-\underset{\underset{\text{iPr}}{|}}{\overset{\overset{\text{iPr}}{|}}{\text{C}}}-\underset{\underset{\text{N(Me)}_2}{|}}{\text{C}}=\text{N}-\text{Me}\right]_2$$

No. 274

$$\text{Co}\left[\text{O}-\underset{\underset{\text{Me}}{|}}{\overset{\overset{\text{Me-Si-Me}}{\overset{|}{\text{Me}}}}{\text{C}}}-\underset{\underset{\text{N(Me)}_2}{|}}{\text{C}}=\text{N}-\text{Me}\right]_2$$

No. 275

$$\text{Co}\left[\text{O}-\underset{\underset{\text{Me}}{|}}{\overset{\overset{\text{Et-Si-Et}}{\overset{|}{\text{Et}}}}{\text{C}}}-\underset{\underset{\text{N(Me)}_2}{|}}{\text{C}}=\text{N}-\text{Me}\right]_2$$

No. 276

$$\text{Co}\left[\text{O}-\underset{\underset{\text{Me}}{|}}{\overset{\overset{\text{C}=\text{CH}_2}{\overset{|}{\text{H}}}}{\text{C}}}-\underset{\underset{\text{N(Me)}_2}{|}}{\text{C}}=\text{N}-\text{Me}\right]_2$$

No. 277

$$\text{Co}\left[\text{O}-\underset{\underset{\text{Et}}{|}}{\overset{\overset{\text{Et}}{|}}{\text{C}}}-\underset{\underset{\text{N(Me)}_2}{|}}{\text{C}}=\text{N}-\text{Et}\right]_2$$

No. 278

$$\text{Co}\left[\text{O}-\underset{\underset{\text{Et}}{|}}{\overset{\overset{\text{iPr}}{|}}{\text{C}}}-\underset{\underset{\text{N(Me)}_2}{|}}{\text{C}}=\text{N}-\text{Et}\right]_2$$

No. 279

$$\text{Co}\left[\text{O}-\underset{\underset{\text{iPr}}{|}}{\overset{\overset{\text{iPr}}{|}}{\text{C}}}-\underset{\underset{\text{N(Me)}_2}{|}}{\text{C}}=\text{N}-\text{Et}\right]_2$$

No. 280

[structure: Co—[O—C(Me)(SiMe3 with Me-Si-Me, Me on top)—C(N(Me)2)=N—Et]2]

No. 281

[structure: Co—[O—C(Me)(SiEt2Et)—C(N(Me)2)=N—Et]2]

No. 282

[structure: Co—[O—C(Me)(CH=CH2)—C(N(Me)2)=N—Et]2]

No. 283

[structure: Co—[O—C(Et)(Et)—C(N(Me)2)=N—iPr]2]

No. 284

[structure: Co—[O—C(iPr)(Et)—C(N(Me)2)=N—iPr]2]

No. 285

[structure: Co—[O—C(iPr)(iPr)—C(N(Me)2)=N—iPr]2]

No. 286

[structure: Co—[O—C(Me)(SiMe3)—C(N(Me)2)=N—iPr]2]

No. 287

[structure: Co—[O—C(Me)(SiEt3)—C(N(Me)2)=N—iPr]2]

No. 288

[structure: Co—[O—C(Me)(CH=CH2)—C(N(Me)2)=N—iPr]2]

No. 289

Cp—Co—O—C(Et)(Et)—C(Me)=N—Me

No. 290

Cp—Co—O—C(Et)(Et)—C(Me)=N—Et

No. 291

Cp—Co—O—C(Et)(Et)—C(Me)=N—iPr

No. 292

MeCp—Co—O—C(Et)(Et)—C(Me)=N—Me

No. 293

MeCp—Co—O—C(Et)(Et)—C(Me)=N—Et

No. 294

MeCp—Co—O—C(Et)(Et)—C(Me)=N—iPr

No. 295 sCp—Co—O—C(Et)(Et)—C(Me)=N—Me

No. 296 sCp—Co—O—C(Et)(Et)—C(Me)=N—Et

No. 297 sCp—Co—O—C(Et)(Et)—C(Me)=N—iPr

No. 298

AMD—Co—O—C(Et)(Et)—C(Me)=N—Me

No. 299

AMD—Co—O—C(Et)(Et)—C(Me)=N—Et

No. 300

AMD—Co—O—C(Et)(Et)—C(Me)=N—iPr

The alkoxide compound of the present invention is not particularly restricted by the manufacturing method thereof and can be manufactured by using a well-known reaction. A method for synthesizing a typical well-known alkoxide compound that uses the respective alcohol can be used for manufacturing the alkoxide compound for which m in General Formula (I) is 0. For example, a cobalt alkoxide compound can be manufactured, for example, by a method of conducting a reaction of an inorganic cobalt salt such as halide and nitrate, or a hydrate thereof with the corresponding alcohol compound in the presence of a base such as sodium, sodium hydride, sodium amide, sodium hydroxide, sodium methylate, ammonia, and amine, a method of conducting a reaction of an inorganic cobalt salt such as halide and nitrate, or a hydrate thereof with an alkali metal alkoxide, such as sodium alkoxide, lithium alkoxide, and potassium alkoxide, of the corresponding alcohol compound, a method of conducting an exchange reaction of a cobalt alkoxide compound of a low-molecular alcohol, such as methoxide, ethoxide, isopropoxide, and butoxide, with the corresponding alcohol compound, and a method of reacting an inorganic cobalt salt such as halide and nitrate with a derivative providing a reactive intermediate, thereby obtaining the reactive intermediate, and then reacting the intermediate with the corresponding alcohol compound. Examples of the reactive intermediate include bis(dialkylamino)cobalt, bis(bis(trimethylsilyl)amino)cobalt, and amido compounds of cobalt. Further, an alkoxide compound for which m in General Formula (I) is 1 or more can be manufactured by reacting an alkoxide compound for which m in General Formula (I) is 0 with an organic compound providing the desired ligand, or an alkali metal salt thereof.

The raw material for forming a thin film of the present invention includes the alkoxide compound of the present invention, which has been explained hereinabove, as a precursor for the thin film, and the form of the raw material differs depending on the manufacturing process in which the raw material for forming a thin film is to be used. For example, when a thin film including only a metal of one type or silicon is manufactured, the raw material for forming a thin film of the present invention does not include metal compounds or semimetal compounds other than the alkoxide compound. Meanwhile, where a thin film including metals and/or semimetals of two or more types is manufactured, the raw material for forming a thin film of the present invention includes, in addition to the abovementioned alkoxide compound, a compound including the desired metal and/or a compound including the desired semimetal (can be also referred to hereinbelow as "other precursor"). As will be described hereinbelow, the raw material for forming a thin film of the present invention may additionally include an organic solvent and/or a nucleophilic reagent. Since physical properties of the alkoxide compound serving as the precursor are advantageous for the CVD method and ALD method, the raw material for forming a thin film of the present invention is particularly useful as a raw material for chemical vapor deposition (referred to hereinbelow as "CVD").

Where the raw material for forming a thin film of the present invention is a raw material for chemical vapor deposition, the form thereof can be selected, as appropriate, according, e.g., to the delivery and feed method in the CVD method which is to be used.

The delivery and feed method can be a gas delivery method in which a CVD source is vaporized by heating and/or depressurizing the interior of a container in which the source is stored (can be referred to hereinbelow simply as "raw material container"), and the obtained vapor is introduced, optionally together with a carrier gas such as argon, nitrogen, and helium, into a film formation chamber in which a substrate is disposed (can be also referred to hereinbelow as "deposition reaction unit") or a liquid delivery method in which a CVD source is transported in a state of a liquid or solution into a vaporization chamber and vaporized by heating and/or depressurizing in the vaporization chamber, and the vapor is introduced into a film formation chamber. When the gas delivery method is used, the alkoxide compound itself, which is represented by General Formula (I), can be used as the CVD source. When the liquid delivery method is used, the alkoxide compound itself, which is represented by General Formula (I), or a solution obtained by dissolving the compound in an organic solvent can be used as the CVD source. Those CVD sources may additionally include the other precursor, a nucleophilic reagent or the like.

Further, CVD of a multicomponent system can be implemented by a method of vaporizing and feeding CVD sources for each component independently (can be also referred to hereinbelow as "single source method") and a method of vaporizing and feeding a mixed raw material obtained by mixing in advance multicomponent raw materials at the desired composition ratio (can be also referred to hereinbelow as "cocktail source method"). When the cocktail source method is used, a mixture of the alkoxide compound of the present invention and the other precursor, or a mixed solution obtained by dissolving the mixture in an organic solvent can be used as the CVD source. The mixture or mixed solvent may additionally include a nucleophilic reagent. Where only the alkoxide compound of the present invention is used as the precursor and the (R) and (S) enantiomers are used together, the CVD source which includes the (R) enantiomer and the CVD source which includes the (S) enantiomer may be vaporized separately, or the CVD source including a mixture of the (R) and (S) enantiomers may be vaporized.

The organic solvent is not particularly limited, and well-known typical organic solvents can be used. Examples of the organic solvents include acetates such as ethyl acetate, butyl acetate, and methoxyethyl acetate; ethers such as tetrahydrofuran, tetrahydropyran, ethylene glycol dimethyl ether, diethylene glycol dimethyl ether, triethylene glycol dimethyl ether, dibutyl ether, and dioxane; ketones such as methyl butyl ketone, methyl isobutyl ketone, ethyl butyl ketone, dipropyl ketone, diisobutyl ketone, methyl pentyl ketone, cyclohexanone, and methylcyclohexanone; hydrocarbons such as hexane, cyclohexane, methylcyclohexane, dimethylcyclohexane, ethylcyclohexane, heptane, octane, toluene, and xylene; hydrocarbons including a cyano group such as 1-cyanopropane, 1-cyanobutane, 1-cyanohexane, cyanocyclohexane, cycanobenzene, 1,3-dicyanopropane, 1,4-dicyanobutane, 1,6-dicyanohexane, 1,4-dicyanocyclohexane, and 1,4-dicyanobenzene; pyridine and lutidine. Such organic solvents are used individually or as mixed solvents of two or more thereof according to the relationship between the solute solubility, usage temperature, boiling point, and flash point. When such organic solvents are used, the amount of the entire precursor in the CVD source which is a solvent in which the precursor is dissolved in the organic solvent is preferably 0.01 mol/L to 2.0 mol/L, in particular, 0.05 mol/L to 1.0 mol/L. The amount of the entire precursor, as referred to herein, is the amount of the alkoxide compound of the present invention when the raw material for forming a thin film of the present invention does not include a metal compound or a semimetal compound other than the alkoxide compound of the present invention, and is the total amount of the alkoxide compound of the present invention and the other precursor when the raw material for forming a thin film of the present invention includes a compound including other metal and/or a compound including a semimetal in addition to the alkoxide compound.

When CVD of a multicomponent system is performed, the other precursor which is used together with the alkoxide compound of the present invention is not particularly limited, and any well-known typical precursor which has been used in CVD sources can be used.

Examples of the other precursor include one, or two or more compounds of silicon or a metal selected from a group including compounds having a hydride, a hydroxide, a halide, an azide, an alkyl, an alkenyl, a cycloalkyl, an aryl, an alkynyl, an amino, a dialkylaminoalkyl, a monoalkylamino, a dialkylamino, a diamine, a di(silyl-alkyl)amino, a di(alkyl-silyl)amino, a disilylamino, an alkoxy, an alkoxyalkyl, a hydrazido, a phosphido, a nitrile, a dialkylaminoalkoxy, an alkoxyalkyldialkylamino, a siloxy, a diketonate, a cyclopentadienyl, a silyl, a pyrazolate, a guanidinate, a phosphoguanidinate, an amidinate, a phosphoamidinate, a ketoiminate, a diketoiminate, a carbonyl, and a phosphoamidinate as a ligand.

Examples of metals for the precursor include magnesium, calcium, strontium, barium, radium, scandium, yttrium, titanium, zirconium, hafnium, vanadium, niobium, tantalum, chromium, molybdenum, tungsten, manganese, iron, osmium, cobalt, rhodium, iridium, nickel, palladium, platinum, copper, silver, gold, zinc, cadmium, aluminum, gallium, indium, germanium, tin, lead, antimony, bismuth, lanthanum, cerium, praseodymium, neodymium, promethium, samarium, europium, gadolinium, terbium, dysprosium, holmium, erbium, thulium, and ytterbium.

Such other precursors are well known in the pertinent technical field, and the manufacturing methods thereof are also well known. For example, where an alcohol compound is used as the organic ligand, the precursor can be manufactured by conducting a reaction of the abovementioned inorganic metal salt or a hydrate thereof and the alkali metal alkoxide of the alcohol compound. Examples of the inorganic metal salt and hydrate thereof include metal halides and nitrates, and examples of the alkali metal alkoxides include sodium alkoxide, lithium alkoxide, and potassium alkoxide.

In the case of a single source method, it is preferred that the other precursor be a compound demonstrating thermal and/or oxidative decomposition behavior similar to that of the alkoxide compound of the present invention. In the case of a cocktail source method, it is preferred that the precursor have similar thermal and/or oxidative decomposition behavior and also demonstrate no transformations induced by chemical reactions or the like at the time of mixing.

Compounds represented by Formulas (II-1) to (II-5) below are examples of precursors including titanium, zirconium, or hafnium among the other precursors.

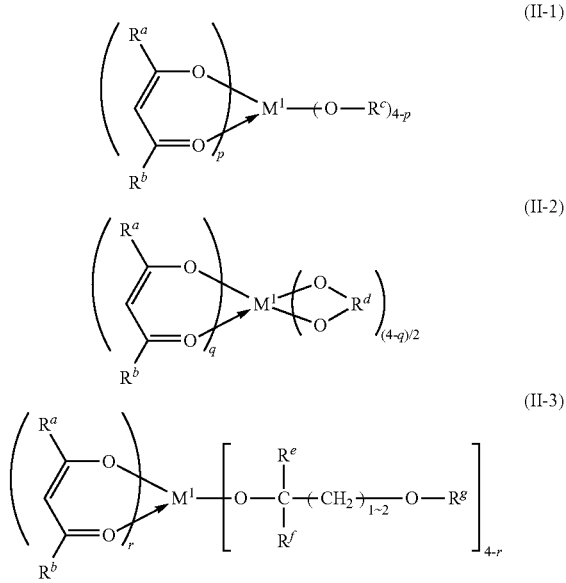

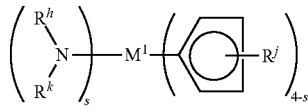

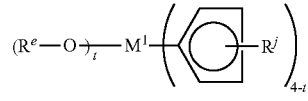

In the formulas, $M^1$ represents titanium, zirconium, or hafnium; $R^a$ and $R^b$ each independently represent a $C_{1-20}$ alkyl group which may be substituted with a halogen atom and may contain an oxygen atom in a chain; $R^c$ represents a $C_{1-8}$ alkyl group; $R^d$ represents an optionally branched $C_{2-18}$ alkylene group; $R^e$ and $R^f$ each independently represent a hydrogen atom or a $C_{1-3}$ alkyl group; $R^g$, $R^h$, $R^k$, and $R^j$ each independently represent a hydrogen atom or a $C_{1-4}$ alkyl group; p represents an integer of 0 to 4; q represents 0 or 2; r represents an integer of 0 to 3; s represents an integer of 0 to 4; and t represents an integer of 1 to 4.

Examples of the $C_{1-20}$ alkyl group which may be substituted with a halogen atom and may contain an oxygen atom in a chain, this group being represented by $R^a$ and $R^b$ in Formulas (II-1) to (II-5), include methyl, ethyl, propyl, isopropyl, butyl, sec-butyl, tert-butyl, isobutyl, pentyl, isopentyl, neopentyl, tert-pentyl, hexyl, cyclohexyl, 1-methylcyclohexyl, heptyl, 3-heptyl, isoheptyl, tert-heptyl, n-octyl, isooctyl, tert-octyl, 2-ethylhexyl, trifluoromethyl, perfluorohexyl, 2-methoxyethyl, 2-ethoxyethyl, 2-butoxyethyl, 2-(2-methoxyethoxy)ethyl, 1-methoxy-1,1-dimethylmethyl, 2-methoxy-1,1-dimethylethyl, 2-ethoxy-1,1-dimethylethyl, 2-isopropoxy-1,1-dimethylethyl, 2-butoxy-1,1-dimethylethyl, and 2-(2-methoxyethoxy)-1,1-dimethylethyl. The $C_{1-8}$ alkyl group as represented by $R^c$ includes methyl, ethyl, propyl, isopropyl, butyl, sec-butyl, tert-butyl, isobutyl, pentyl, isopentyl, neopentyl, tert-pentyl, hexyl, 1-ethylpentyl, cyclohexyl, 1-methylcyclohexyl, heptyl, isoheptyl, tert-heptyl, n-octyl, isooctyl, tert-octyl, and 2-ethylhexyl. The optionally branched $C_{2-18}$ alkylene group which is represented by $R^d$ is a group derived from a glycol. Examples of the glycol include 1,2-ethanediol, 1,2-propanediol, 1,3-propanediol, 1,3-butanediol, 2,4-hexanediol, 2,2-dimethyl-1,3-propanediol, 2,2-diethyl-1,3-propanediol, 2,2-diethyl-1,3-butanediol, 2-ethyl-2-butyl-1,3-propanediol, 2,4-pentanediol, 2-methyl-1,3-propanediol, and 1-methyl-2,4-pentanediol. Examples of the $C_{1-3}$ alkyl group which is represented by $R^e$ and $R^f$ include methyl, ethyl, propyl, and 2-propyl. Examples of the $C_{1-4}$ alkyl group which is represented by $R^g$, $R^h$, $R^j$, and $R^k$ include methyl, ethyl, propyl, isopropyl, butyl, sec-butyl, tert-butyl, and isobutyl.

Specific examples of precursors including titanium include tetrakis(alkoxy)titanium such as tetrakis(ethoxy)titanium, tetrakis(2-propoxy) titanium, tetrakis(butoxy) titanium, tetrakis(sec-butoxy) titanium, tetrakis(isobutoxy)titanium, tetrakis(tert-butoxy)titanium, tetrakis(tert-pentyl) titanium, and tetrakis(1-methoxy-2-methyl-2-propoxy) titanium; tetrakis-β-diketonatotitanium such as tetrakis (pentane-2,4-dionato)titanium, (2,6-dimethylheptane-3,5-dionato) titanium, and tetrakis(2,2,6,6-tetramethylheptane-3,5-dionato)titanium; bis(alkoxy)bis(β-diketonato)titanium such as bis(methoxy)bis(pentane-2,4-dionato)titanium, bis (ethoxy)bis(pentane-2,4-dionato)titanium, bis(tert-butoxy) bis(pentane-2,4-dionato)titanium, bis(methoxy)bis(2,6-dimethylheptane-3,5-dionato) titanium, bis(ethoxy)bis(2,6- dimethylheptane-3,5-dionato)titanium, bis(2-propoxy)bis(2,6-dimethylheptane-3,5-dionato)titanium, bis(tert-butoxy)bis(2,6-dimethylheptane-3,5-dionato)titanium, bis(tert-amyloxy)bis(2,6-dimethylheptane-3,5-dionato) titanium, bis(methoxy)bis(2,2,6,6-tetramethylheptane-3,5-dionato) titanium, bis(ethoxy)bis(2,2,6,6-tetramethylheptane-3,5-dionato)titanium, bis(2-propoxy)bis(2,6,6,6-tetramethylheptane-3,5-dionato) titanium, bis(tert-butoxy)bis(2,2,6,6-tetramethylheptane-3,5-dionato)titanium, and bis(tert-amyloxy)bis(2,2,6,6-tetramethylheptane-3,5-dionato) titanium; and glycoxybis(β-diketonato)titanium such as (2-methylpentanedioxy)bis(2,2,6,6-tetramethylheptane-3,5-dionato)titanium and (2-methylpentanedioxy)bis(2,6-dimethylheptane-3,5-dionato)titanium; (cyclopentadienyl)tris(dialkylamino)titanium such as (methylcyclopentadienyl)tris(dimethylamino)titanim, (ethylcyclopentadienyl)tris(dimethylamino)titanium, (cyclopentadienyl)tris(dimethylamino)titanium, (methylcyclopentadienyl)tris(ethylmethylamino)titanim, (ethylcyclopentadienyl)tris(ethylmethylamino)titanium, (cyclopentadienyl)tris(ethylmethylamino)titanium, (methylcyclopentadienyl)tris(diethylamino)titanium, (ethylcyclopentadienyl)tris(diethylamino)titanium, and (cyclopentadienyl)tris(diethylamino)titanium; (cyclopentadienyl)tris(alkoxy)titanium such as (cyclopentadienyl)tris(methoxy)titanium, (methylcyclopentadienyl)tris(methoxy) titanium, (ethylcyclopentadienyl)tris(methoxy)titanium, (propylcyclopentadienyl)tris(methoxy) titanium, (isopropylcyclopentadienyl)tris(methoxy)titanium, (butylcyclopentadienyl)tris(methoxy)titanium, (isobutylcyclopentadienyl)tris(methoxy)titanium, (tert-butylcyclopentadienyl)tris(methoxy)titanium, and (pentamethylcyclopentadienyl)tris(methoxy)titanium. Examples of precursors including zirconium or hafnium are compounds presented as examples of titanium-containing precursors in which titanium is substituted with zirconium or hafnium.

Examples of precursors including rare earth metals are compounds represented by Formulas (III-1) to (III-3).

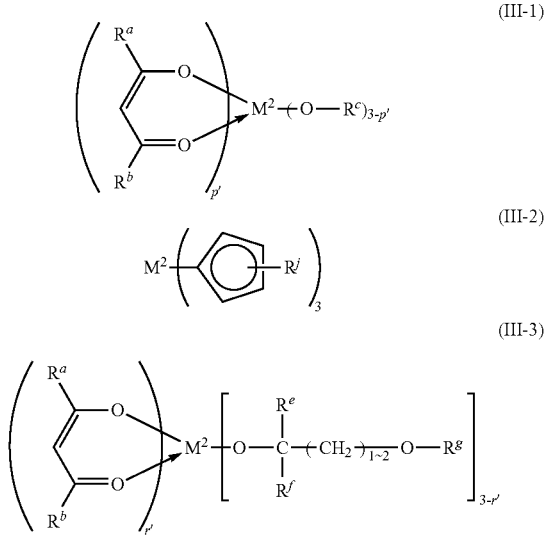

In the formulas, $M^2$ represents a rare earth atom; $R^a$ and $R^b$ each independently represent a $C_{1-20}$ alkyl group which may be substituted with a halogen atom and may contain an oxygen atom in a chain; $R^c$ represents a $C_{1-8}$ alkyl group; $R^e$ and $R^f$ each independently represent a hydrogen atom or a $C_{1-3}$ alkyl group; $R^g$ and $R^j$ each independently represent a $C_{1-4}$ alkyl group; p' represents an integer of 0 to 3; and r' represents an integer of 0 to 2.

Examples of rare earth atoms represented by $M^2$ in the precursor including a rare earth element include scandium, yttrium, lanthanum, cerium, praseodymium, neodymium, promethium, samarium, europium, gadolinium, terbium, dysprosium, holmium, erbium, thulium, ytterbium, and lutetium. Examples of groups represented by $R^a$, $R^b$, $R^c$, $R^e$, $R^f$, $R^g$, and $R^j$ include groups presented by way of examples with respect to the titanium-containing precursors.

If necessary, the raw material for forming a thin film of the present invention may include a nucleophilic reagent to stabilize the alkoxide compound of the present invention and the other precursor. Examples of the nucleophilic reagent include ethylene glycol ethers such as glyme, diglyme, triglyme, and tetraglyme; crown ethers such as 18-crown-6, dicyclohexyl-18-crown-6, 24-crown-8, dicyclohexyl-24-crown-8, and dibenzo-24-crown-8; polyamines such as ethylenediamine, N,N'-tetramethylethylenediamine, diethylenetriamine, triethylenetetramine, tetraethylenepentamine, pentaethylenehexamine, 1,1,4,7,7-pentamethyldiethylentriamine, 1,1,4,7,10,10-hexamethyltriethylenetetramine, and triethoxytriethyleneamine; cyclic polyamines such as cyclam and cyclen; heterocyclic compounds such as pyridine, pyrrolidine, piperidine, morpholine, N-methylpyrrolidine, N-methylpiperidine, N-methylmorpholine, tetrahydrofuran, tetrahydropyran, 1,4-dioxane, oxazole, thiazole, and oxathiolane; β-keto esters such as methyl acetoacetate, ethyl acetoacetate, and 2-methoxyethyl acetoacetate; and β-diketones such as acetylacetone, 2,4-hexanedione, 2,4-heptanedione, 3,5-heptanedione, and dipivaroylmethane. These nucleophilic reagents are used in an amount preferably within a range of 0.1 mol to 10 mol, more preferably 1 mol to 4 mol per mole of the amount of the entire precursor.

In the raw material for forming a thin film of the present invention, the amount of metal element impurities, halogen impurities such as chlorine-containing impurities, and organic impurities, which are different from the components constituting the raw materials, needs to be minimized. The content of the metal element impurities is preferably 100 ppb or less, and more preferably 10 ppb or less for each element, and the total amount of the impurities is preferably 1 ppm or less, and more preferably 100 ppb or less. In particular, when the raw material is used to form a gate insulating layer, a gate film, or a barrier layer of an LSI, it is necessary to reduce the amount of alkali metal elements and alkaline earth metal elements which affect the electric properties of a thin film to be obtained. The amount of the halogen impurities is preferably 100 ppm or less, more preferably 10 ppm or less, and most preferably 1 ppm or less. The total amount of organic impurities is preferably 500 ppm or less, more preferably 50 ppm or less, and most preferably 10 ppm or less. Since moisture causes particle generation in the raw material for chemical vapor deposition or particle generation during thin film formation, it is better to remove moisture as much as possible prior to use from the metal compound, the organic solvent, and the nucleophilic reagent in order to reduce the amount of moisture therein. The amount of moisture in each of the metal compound, the organic solvent, and the nucleophilic reagent is 10 ppm or less, and more preferably 1 ppm or less.

Further, in order to reduce or prevent the particle contamination of the thin film to be formed, it is preferred that the raw material for forming a thin film of the present invention include as few particles as possible. More specifically, in particle measurements with a particle detector of a light scattering type in a liquid phase, the number of particles larger than 0.3 µm is preferably 100 or less in 1 ml of the liquid phase, more preferably the number of particles larger than 0.2 µm is 1000 or less in 1 ml of the liquid phase, and most preferably the number of particles larger than 0.2 µm is 100 or less in 1 ml of the liquid phase.

A method for manufacturing a thin film of the present invention by which a thin film is manufactured by using the raw material for forming a thin film of the present invention is based on the CVD method in which a vapor produced by vaporizing the raw material for forming a thin film of the present invention, and an optionally used reactive gas are introduced into a film formation chamber in which a substrate is disposed, and the precursor is then decomposed and/or chemically reacted on the substrate to grow and deposit a thin film including a metal on the substrate surface. The method for delivering and feeding the raw materials, the deposition method, manufacturing conditions, and manufacturing apparatus are not particularly restricted, and well-known typical conditions and methods can be used.

Examples of the optionally used reactive gas include oxidative gases such as oxygen, ozone, nitrogen dioxide, nitrogen monoxide, water vapor, hydrogen peroxide, formic acid, acetic acid, and acetic anhydride; reductive gases such as hydrogen; and gases producing nitrides, for example, organic amine compounds such as monoalkylamines, dialkylamines, trialkylamines, and alkylenediamines, hydrazine, and ammonia. These gases can be used individually or in combinations of two or more thereof.

Examples of the delivery and feeding methods include the above-described gas delivery method, liquid delivery method, single source method, and cocktail source method.

Examples of the deposition method include thermal CVD in which a source gas or a source gas and a reactive gas are reacted only by heat in order to deposit a thin film; plasma CVD in which heat and plasma are used; photo-excited CVD in which heat and light are used; photo- and plasma-excited CVD in which heat, light and plasma are used; and ALD in which the CVD deposition reaction is separated into elementary steps and deposition is performed step by step at a molecular level.

Examples of the substrate material include silicon, ceramics such as silicon nitride, titanium nitride, tantalum nitride, titanium oxide, titanium nitride ruthenium oxide, zirconium oxide, hafnium oxide, and lanthanum oxide; glass; and metals such as metallic ruthenium. The substrate may be in the form of a sheet, sphere, fibers, and flakes. The substrate surface may be flat or may have a three-dimensional structure such as a trench structure.

The manufacturing conditions include the reaction temperature (substrate temperature), reaction pressure, deposition rate, and the like. The reaction temperature is preferably 100° C. or higher, at which the alkoxide compound of the present invention is sufficiently reactive, and more preferably 150° C. to 400° C. The reaction pressure is preferably from atmospheric pressure to 10 Pa for thermal CVD and photo-excited CVD, and preferably from 2000 Pa to 10 Pa when plasma is used.

The deposition rate can be controlled by the raw material feed conditions (vaporization temperature and vaporization pressure), reaction temperature, and reaction pressure. Since a high deposition rate can degrade the properties of the resulting thin film and a low deposition rate can cause problems with productivity, the deposition rate is preferably 0.01 nm/min to 100 nm/min and more preferably 1 nm/min to 50 nm/min. In the ALD method, the control is performed by the number of cycles so as to obtain the desired film thickness.

The temperature or pressure during vaporization of the raw material for forming a thin film can be also considered as the manufacturing condition. The step of obtaining the vapor by vaporizing the raw material for forming a thin film may be performed inside the raw material container or inside the vaporization chamber. In either case, it is preferred that the raw material for forming a thin film of the present invention be evaporated at 0° C. to 150° C. Further, where the raw material for forming a thin film is vaporized to obtain the vapor inside the raw material container or vaporization chamber, it is preferred that the pressure inside the raw material container and the pressure inside the vaporization chamber be 1 Pa to 10,000 Pa.

The method for manufacturing a thin film of the present invention, when it is realized by the ALD method, may include a raw material introduction step in which the raw material for forming a thin film is vaporized to obtain a vapor and the vapor is introduced into the film formation chamber by the abovementioned delivery and feeding method, and also a precursor thin film formation step of forming a precursor thin film on the surface of the substrate with the alkoxide compound in the vapor, an evacuation step of evacuating the unreacted alkoxide compound gas, and a metal-containing thin film formation step of chemically reacting the precursor thin film with a reactive gas and forming a thin film including the metal on the surface of the substrate.

Each of the abovementioned steps will be described hereinbelow in greater detail with reference to the case of forming a metal oxide thin film. When a metal oxide thin film is formed by the ALD method, initially, the raw material introduction step, which has been explained hereinabove, is performed. The temperature and pressure preferred when vaporizing the raw material for forming a thin film are the same as explained hereinabove. Then, a precursor thin film is formed on the substrate surface with the alkoxide compound introduced in the deposition reaction unit (precursor thin film formation step). At this time, heat may be applied by heating the substrate or heating the deposition reaction unit. The precursor thin film which is formed in this step is a metal oxide thin film or a thin film generated by decomposition and/or reaction of part of the alkoxide compound and has a composition different from the target metal oxide thin film. The substrate temperature employed in this step is preferably from room temperature to 500° C., more preferably from 150° C. to 350° C. The pressure in the system (in the film formation chamber) when this step is performed is preferably 1 Pa to 10,000 Pa, more preferably 10 Pa to 1000 Pa.

The unreacted alkoxide gas and byproduct gas are then evacuated from the deposition reaction unit (evacuation step). The unreacted alkoxide gas and byproduct gas are ideally completely evacuated from the deposition reaction unit, but such complete evacuation is not always necessary. Examples of the evacuation method include a method of purging the interior of the system with an inactive gas such as nitrogen, helium, and argon, a method of evacuating by depressurizing the interior of the system, and a method in which the aforementioned methods are combined. The degree of depressurization when the depressurization method is used is preferably 0.01 Pa to 300 Pa, more preferably 0.01 Pa to 100 Pa.

The reactive gas is then introduced into the deposition reaction unit and a metal oxide thin film is formed from the precursor thin film, which has been formed in the preceding precursor thin film formation step, under the action of the oxidizing gas or the action of the oxidizing gas and heat (metal oxide-containing thin film formation step). The temperature when heat is used in this step is preferably from room temperature to 500° C., more preferably from 150° C. to 350° C. The pressure in the system (in the film formation chamber) in which this step is performed is preferably 1 Pa to 10,000 Pa, more preferably 10 Pa to 1000 Pa. The alkoxide compound of the present invention has good reactivity with oxidizing gases and can yield a metal oxide thin film.

When the ALD method is used in the above-described manner in the method for manufacturing a thin film of the present invention, thin film deposition performed by a series of operations including the raw material introduction step, precursor thin film formation step, evacuation step, and metal oxide-containing thin film formation step may be taken as one cycle, and such cycles may be repeated a plurality of times till a thin film of a necessary thickness is obtained. In this case, after one cycle is completed, it is preferred that the unreacted alkoxide compound, reactive gas (oxidizing gas when a metal oxide thin film is formed), and byproduct gas be evacuated from the deposition reaction unit in the same manner as in the evacuation step, and the next cycle be thereafter performed.

When a metal oxide thin film is formed by the ALD method, energy such as plasma, light, and voltage may be applied, and a catalyst may be used. The time period for applying the energy and the time period for using the catalyst are not particularly limited. For example, the energy may be applied and the catalyst may be used when the alkoxide compound gas is introduced in the raw material introduction step, during heating in the precursor thin film formation step or metal oxide-containing thin film formation step, during evacuation of the interior of the system in the evacuation step, when the oxidizing gas is introduced in the metal oxide-containing thin film formation step, and also between the aforementioned steps.

Further, in the method for manufacturing a thin film of the present invention, annealing may be performed under an inactive gas atmosphere, an oxidizing atmosphere, or a reducing atmosphere after the thin film deposition to obtain better electric properties, and a reflow step may be employed when bump embedding is needed. In this case, the temperature is 200° C. to 1000° C., preferably 250° C. to 500° C.

Figure 2:
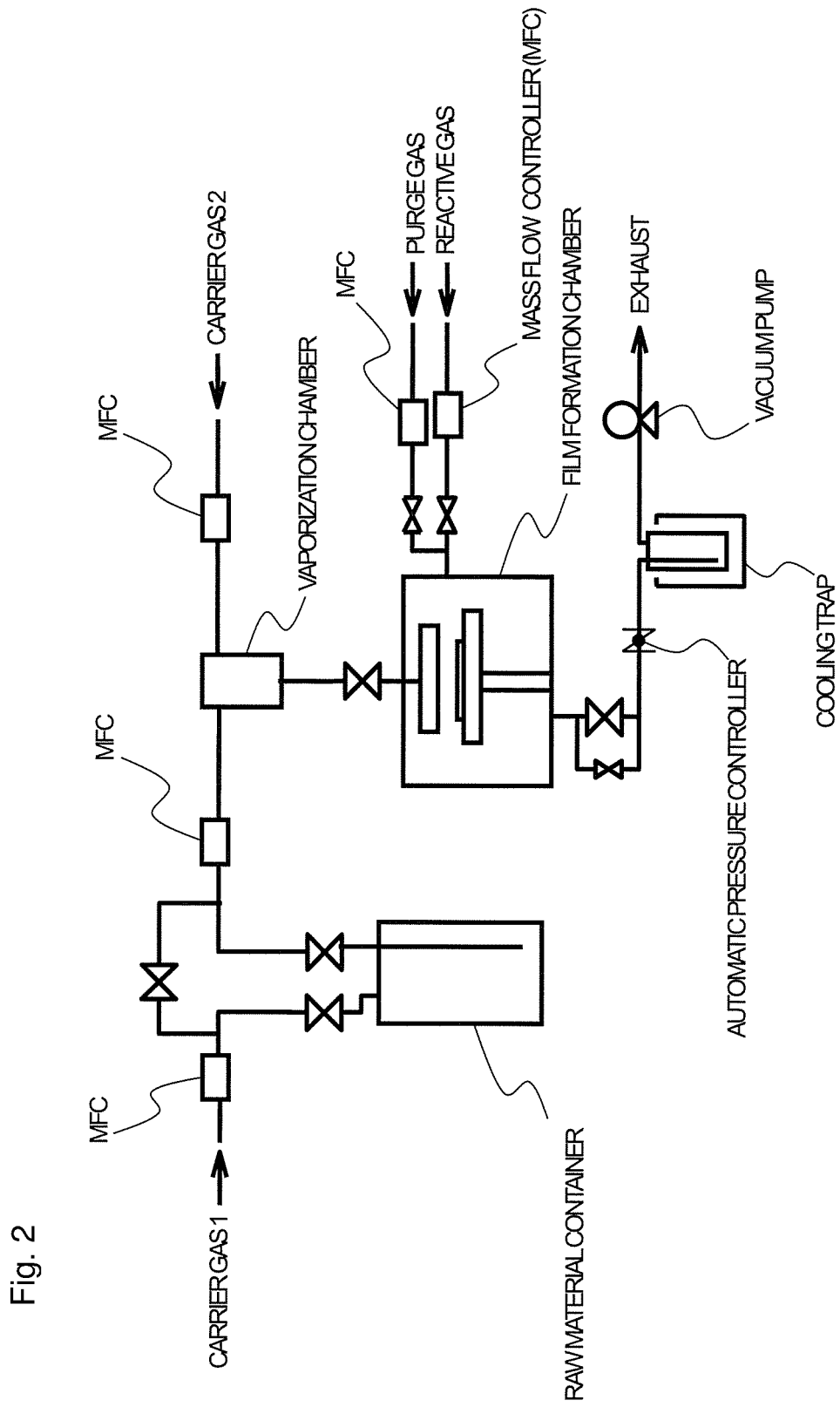
FIG. 2 is a conceptual diagram illustrating another example of a chemical vapor deposition apparatus for use in the method for manufacturing a metal-containing thin film in the present invention.
Figure 3:
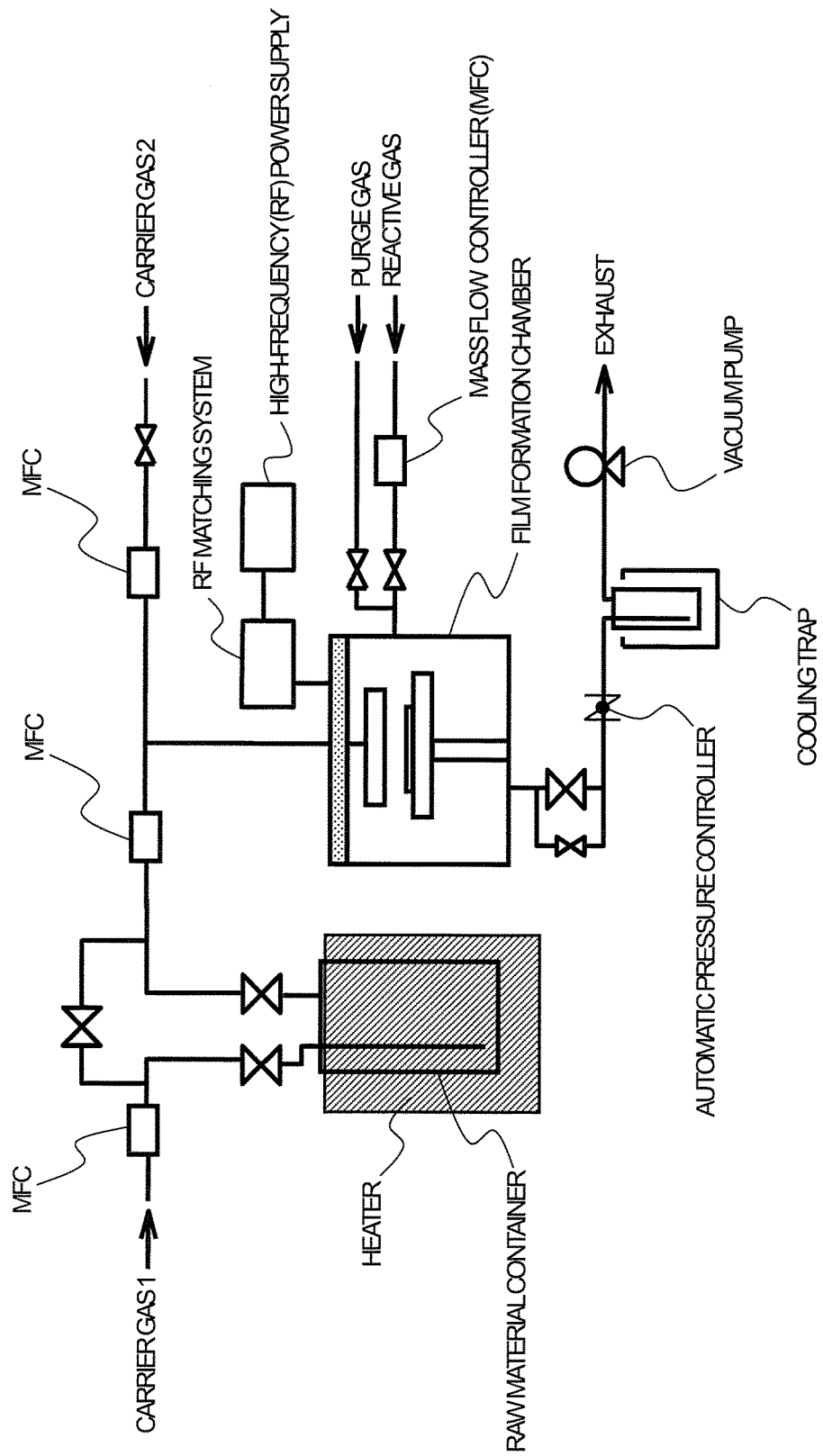
FIG. 3 is a conceptual diagram illustrating another example of a chemical vapor deposition apparatus for use in the method for manufacturing a metal-containing thin film in the present invention.
Figure 4:
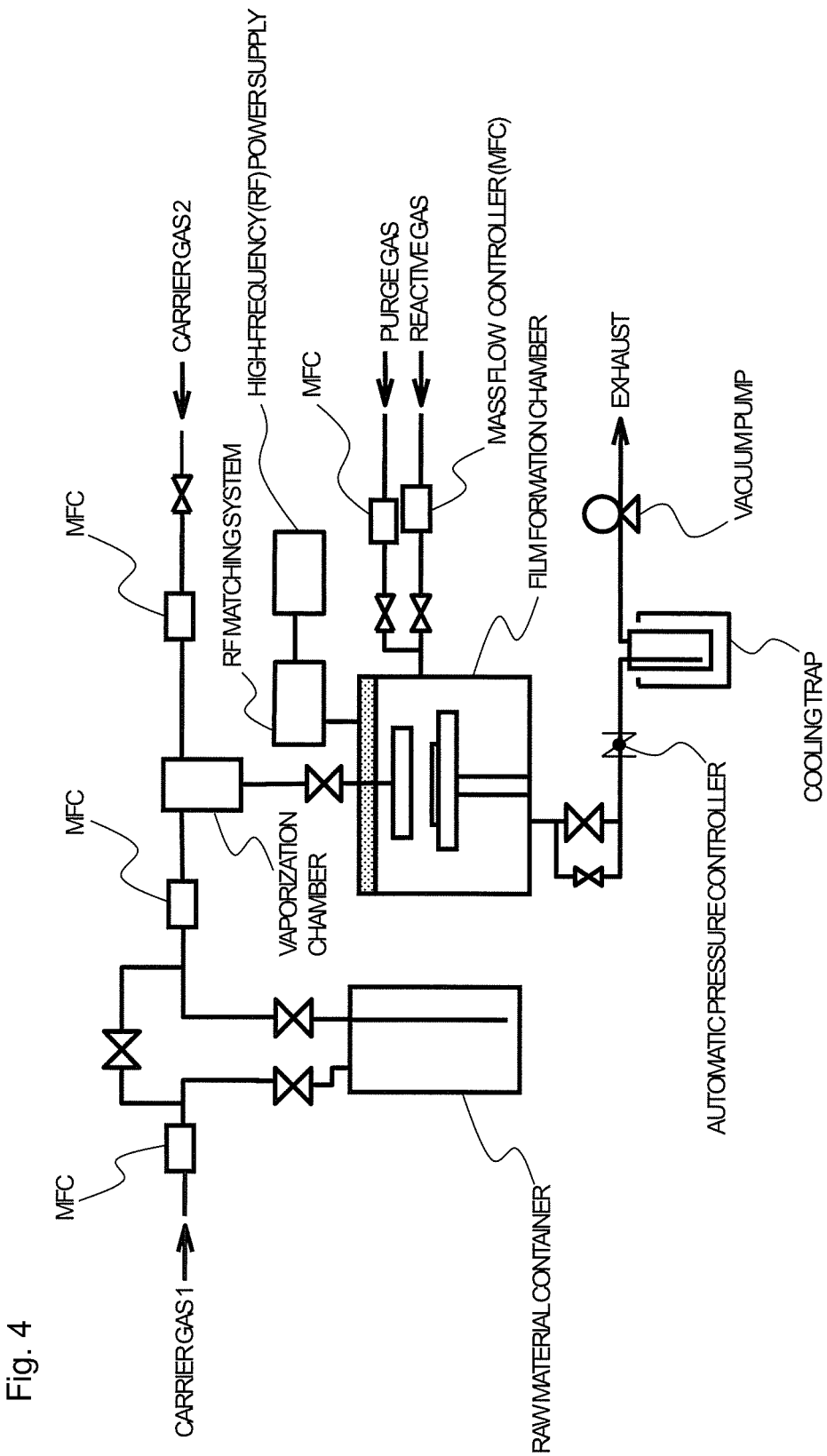
FIG. 4 is a conceptual diagram illustrating another example of a chemical vapor deposition apparatus for use in the method for manufacturing a metal-containing thin film in the present invention.

A well-known chemical vapor deposition apparatus can be used for manufacturing a thin film by using the raw material for forming a thin film of the present invention. Specific examples of suitable apparatuses include an apparatus, such as depicted in FIG. 1, in which a precursor can be fed by bubbling, and an apparatus, such as depicted in FIG. 2, which has a vaporization chamber. An apparatus can be also used in which, as depicted in FIG. 3 and FIG. 4, plasma treatment can be performed with respect to a reactive gas. The single-substrate apparatuses, such as depicted in FIG. 1 to FIG. 4, are not limiting, and an apparatus which uses a batch furnace and is capable of simultaneous processing of a large number of substrates can be also used.

Where a thin film is manufactured using the raw material for forming a thin film of the present invention, the desired type of thin film such as metal, oxide ceramic, nitride ceramic, and glass can be formed by appropriately selecting the other precursor, reactive gas, and manufacturing conditions. Such thin films are known to exhibit various electric properties, optical properties and the like, and are used for a variety of applications. For example, copper and copper-containing thin films have been used as wiring materials for LSI because of a high electric conductivity, high resistance to electromigration, and a high melting point. Further, nickel and nickel-containing thin films are mainly used for parts of electronic components such as resistive films and barrier films, parts for recording media such as magnetic films, and parts for thin-film solar cells, such as electrodes. Cobalt and cobalt-containing thin films have been used for electrode films, resistive films, adhesive films, magnetic tapes, ultra-hard tool members and the like.

The alcohol compound of the present invention is represented by General Formula (II) below. This compound is particularly advantageous as a ligand to be used in a compound advantageous as a precursor in a method for forming a thin film that has a vaporization step, such as the CVD method.

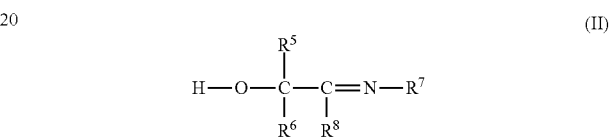

(II)

In the formula, $R^5$ to $R^7$ each independently represent hydrogen, a $C_{1-12}$ hydrocarbon group, or a group represented by General Formulas (Y-1) to (Y-8) below; $R^8$ represents a $C_{1-12}$ hydrocarbon group or a group represented by General Formulas (Y-1) to (Y-8) below; provided that when $R^5$ is a methyl group, $R^6$ is a methyl group or an ethyl group and $R^8$ is a methyl group, $R^7$ represents hydrogen, a $C_{4-12}$ hydrocarbon group or a group represented by General Formulas (Y-1) to (Y-8) below.

(Y-1)

(Y-2)

(Y-3)

(Y-4)

(Y-5)

(Y-6)

(Y-7)

(Y-8)

In the formulas, $R^{Y1}$ to $R^{Y12}$ each independently represent hydrogen or a $C_{1-12}$ hydrocarbon group, and g to $A^{10}$ each represent a $C_{1-6}$ alkanediyl group.

In General Formula (II) of the present invention, $R^5$ to $R^7$ each independently represent hydrogen, a $C_{1-12}$ hydrocarbon group, or a group represented by General Formulas (Y-1) to (Y-8).

For example, an alkyl, an alkenyl, a cycloalkyl, an aryl, or a cyclopentadienyl can be used as the $C_{1-12}$ hydrocarbon group which is represented by $R^5$ to $R^7$.

Examples of the alkyl include methyl, ethyl, propyl, isopropyl, butyl, isobutyl, sec-butyl, tert-butyl, pentyl, isopentyl, hexyl, heptyl, isoheptyl, octyl, isooctyl, 2-ethylhexyl, nonyl, isononyl, decyl, and dodecyl.

Examples of the alkenyl include vinyl, 1-methylethenyl, 2-methylethenyl, propenyl, butenyl, isobutenyl, pentenyl, hexenyl, heptenyl, octenyl, and decenyl.

Examples of the cycloalkyl include cyclohexyl, cyclopentyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl.

Examples of the aryl include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, and 4-cyclohexylphenyl.

Examples of the cyclopentadienyl include cyclopentadienyl, methylcyclopentadienyl, ethylcyclopentadienyl, propylcyclopentadienyl, isopropylcyclopentadienyl, butylcyclopentadienyl, sec-butylcyclopentadienyl, isobutylcyclopentadienyl, tert-butylcyclopentadienyl, dimethylcyclopentadienyl, and tetramethylcyclopentadienyl.

In General Formula (II) of the present invention, $R^8$ represents a $C_{1-12}$ hydrocarbon group or a group represented by General Formulas (Y-1) to (Y-8) above.

Specific examples of the $C_{1-12}$ hydrocarbon group which is represented by $R^8$ can be the same as those listed hereinabove as the examples of the $C_{1-12}$ hydrocarbon group which is represented by $R^5$ to $R^7$.

In General Formula (II) of the present invention, where $R^5$ is a methyl group, $R^6$ is a methyl group or an ethyl group, and $R^8$ is a methyl group, $R^7$ represents hydrogen, a $C_{4-12}$ hydrocarbon group or a group represented by General Formulas (Y-1) to (Y-8) below.

Examples of the $C_{4-12}$ hydrocarbon group include $C_{4-12}$ alkyls, $C_{4-12}$ alkenyls, $C_{6-12}$ cycloalkyls, and $C_{6-12}$ aryls.

Examples of the $C_{4-12}$ alkyls include butyl, isobutyl, sec-butyl, tert-butyl, pentyl, isopentyl, hexyl, heptyl, isoheptyl, octyl, isooctyl, 2-ethylhexyl, nonyl, isononyl, decyl, and dodecyl.

Examples of the $C_{4-12}$ alkenyls include butenyl, isobutenyl, pentenyl, hexenyl, heptenyl, octenyl, and decenyl.

Examples of the $C_{6-12}$ cycloalkyls include cyclohexyl, cyclopentyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl.

Examples of the $C_{6-12}$ aryls include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, and 4-cyclohexylphenyl.

Specific examples of the $C_{1-12}$ hydrocarbon group which is represented by $R^{Y1}$ to $R^{Y12}$ can be the same as those listed hereinabove as the examples of the $C_{1-12}$ hydrocarbon group which is represented by $R^5$ to $R^7$.

Examples of the $C_{1-6}$ alkanediyl group which is represented by $A^8$ to $A^{10}$ include methylene, ethylene, propylene, and butylene.

Examples of the group represented by General Formula (Y-1) include dimethylaminomethyl, ethylmethylaminomethyl, diethylaminomethyl, dimethylaminoethyl, ethylmethylaminoethyl, and diethylaminoethyl.

Examples of the group represented by General Formula (Y-2) include methylamino, ethylamino, propylamino, isopropylamino, butylamino, sec-butylamino, tert-butylamino, and isobutylamino.

Examples of the group represented by General Formula (Y-3) include dimethylamino, diethylamino, dipropylamino, diisopropylamino, dibutylamino, di-sec-butylamino, di-tert-butylamino, ethylmethylamino, propylmethylamino, and isopropylmethylamino.

Examples of the compound represented by General Formula (Y-4) include ethylenediamino, hexamethylenediamino, and N,N-dimethylethylenediamino.

Examples of the group represented by General Formula (Y-5) include di(trimethylsilyl)amino and di(triethylsilyl)amino.

Examples of the group represented by General Formula (Y-6) include trimethylsilyl and triethylsilyl.

Examples of the group represented by General Formula (Y-7) include methoxy, ethoxy, propoxy, isopropoxy, butoxy, sec-butoxy, isobutoxy, tert-butoxy, pentoxy, isopentoxy, and tert-pentoxy.

Examples of the group represented by General Formula (Y-8) include hydroxymethyl, hydroxyethyl, hydroxypropyl, hydroxyisopropyl, and hydroxybutyl.

The alcohol compound of the present invention can have optical isomers, but is not distinguished by the optical isometry.

Specific examples of the alcohol compound represented by General Formula (II) include compounds represented by Chemical Formulas No. 301 to 588 below. In the chemical formulas, "Me" represents methyl, "Et" represents ethyl, and "iPr" represents isopropyl.

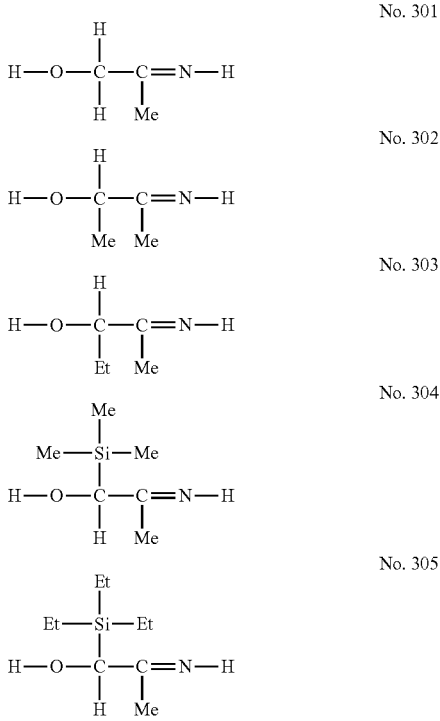

-continued
No. 306
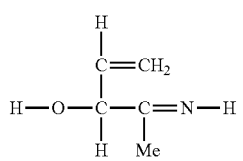
No. 307
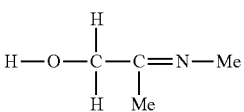
No. 308
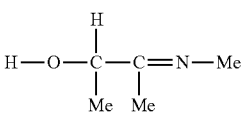
No. 309
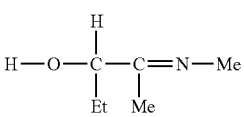
No. 310
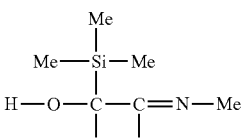
No. 311
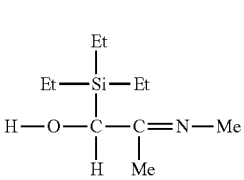
No. 312
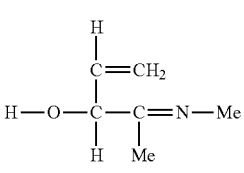
No. 313
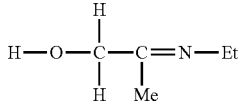
No. 314
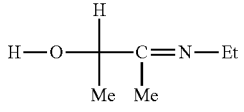
No. 315
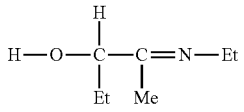
No. 316
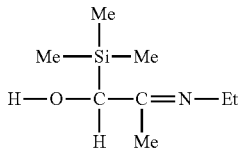
-continued
No. 317
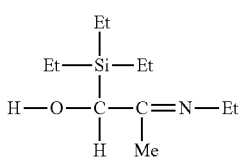
No. 318
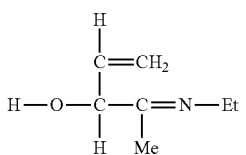
No. 319
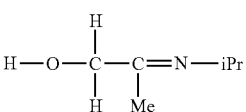
No. 320
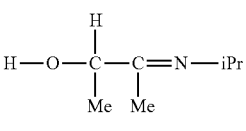
No. 321
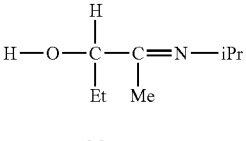
No. 322
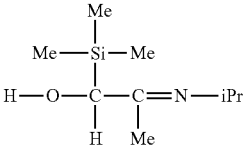
No. 323
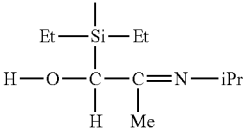
No. 324
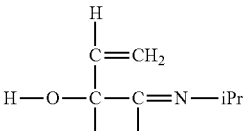
No. 325
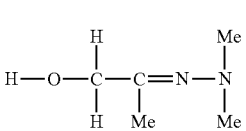
No. 326
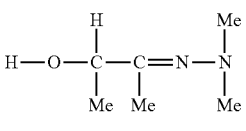
No. 327
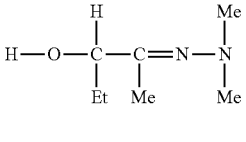

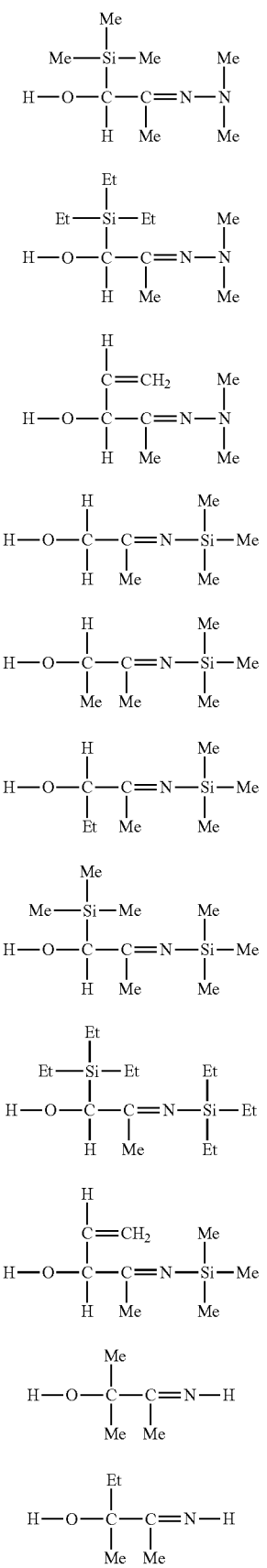
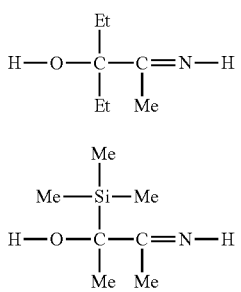
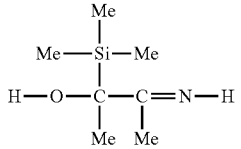
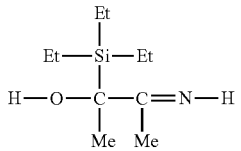
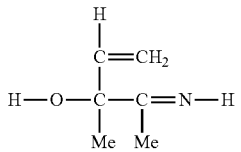
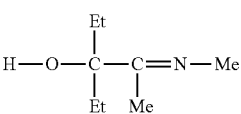
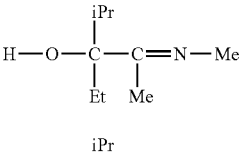
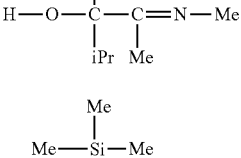
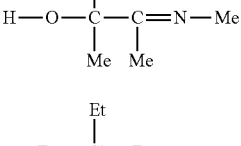
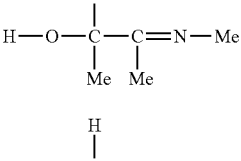
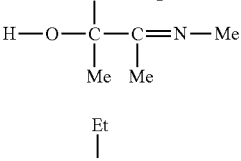
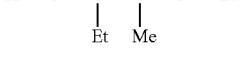

-continued
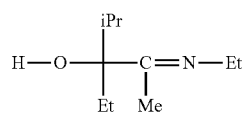
No. 350
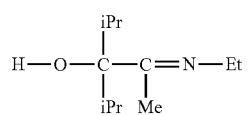
No. 351
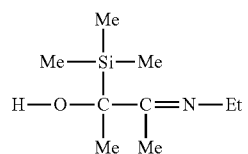
No. 352
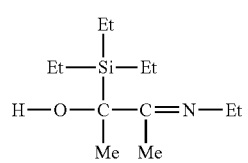
No. 353
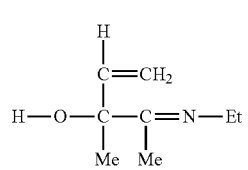
No. 354
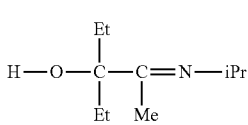
No. 355
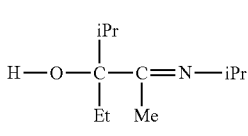
No. 356
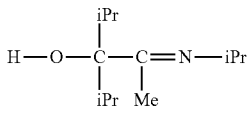
No. 357
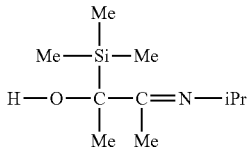
No. 358
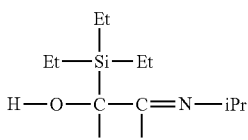
No. 359
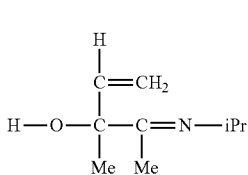
No. 360
-continued
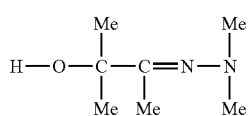
No. 361
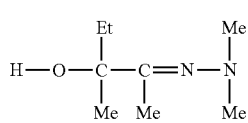
No. 362
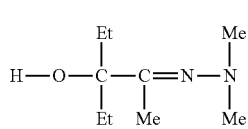
No. 363
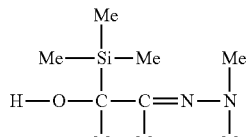
No. 364
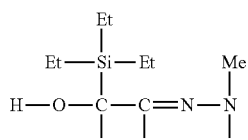
No. 365
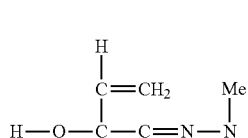
No. 366
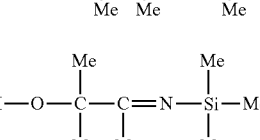
No. 367
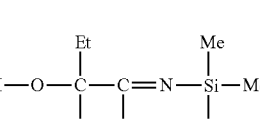
No. 368
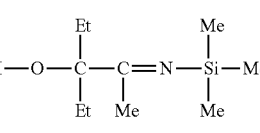
No. 369
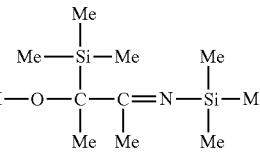
No. 370
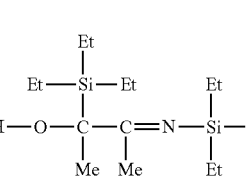
No. 371

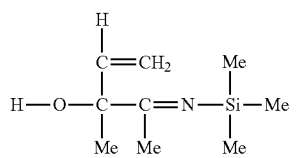 No. 372
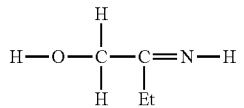 No. 373
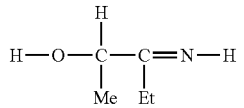 No. 374
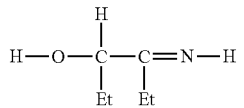 No. 375
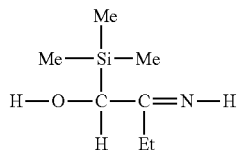 No. 376
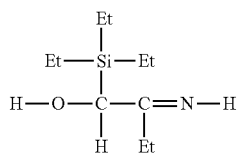 No. 377
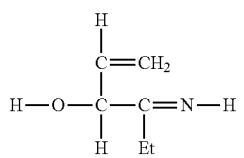 No. 378
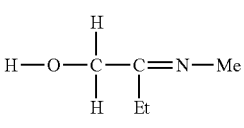 No. 379
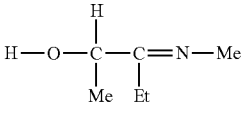 No. 380
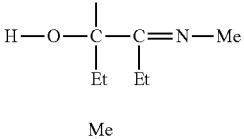 No. 381
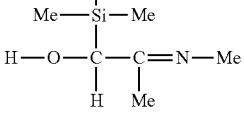 No. 382
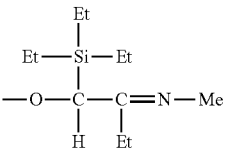 No. 383
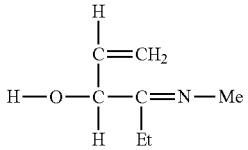 No. 384
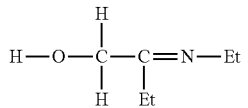 No. 385
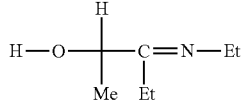 No. 386
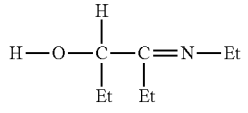 No. 387
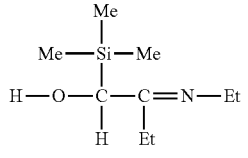 No. 388
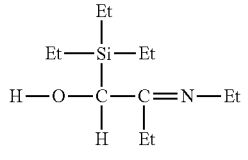 No. 389
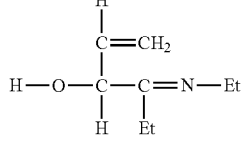 No. 390
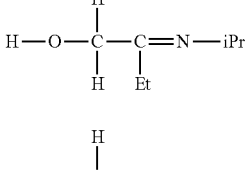 No. 391
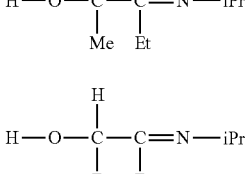 No. 392
 No. 393

-continued

No. 394

Me-Si(Me)(Me)
H-O-C(H)-C(Et)=N-iPr

No. 395

Et-Si(Et)(Et)
H-O-C(H)-C(Et)=N-iPr

No. 396

C(H)=CH₂
H-O-C-C(Et)=N-iPr

No. 397

H-O-C(H)-C(Et)=N-N(Me)(Me)

No. 398

H-O-C(Me)-C(Et)=N-N(Me)(Me)

No. 399

H-O-C(Et)-C(Et)=N-N(Me)(Me)

No. 400

Me-Si(Me)(Me)
H-O-C(H)-C(Et)=N-N(Me)(Me)

No. 401

Et-Si(Et)(Et)
H-O-C(H)-C(Et)=N-N(Me)(Me)

No. 402

C(H)=CH₂
H-O-C-C(Et)=N-N(Me)(Me)

No. 403

H-O-C(H)(H)-C(Et)=N-Si(Me)(Me)(Me)

No. 404

H-O-C(Me)(Et)-C=N-Si(Me)(Me)(Me)

-continued

No. 405

H-O-C(H)-C(Et)=N-Si(Me)(Me)(Me)

No. 406

Me-Si(Me)(Me)
H-O-C(H)-C(Et)=N-Si(Me)(Me)(Me)

No. 407

Et-Si(Et)(Et)
H-O-C(H)-C(Et)=N-N(Et)(Et)

No. 408

C(H)=CH₂
H-O-C-C(Et)=N-Si(Me)(Me)(Me)

No. 409

H-O-C(Me)(Et)-C=N-H

No. 410

H-O-C(Me)(Et)-C(Et)=N-H

No. 411

H-O-C(Et)(Et)-C(Et)=N-H

No. 412

Me-Si(Me)-Me
H-O-C(Me)(Et)-C=N-H

No. 413

Et-Si(Et)
H-O-C(Me)(Et)-C=N-H

No. 414

C(H)=CH₂
H-O-C(Me)(Et)-C=N-H

No. 415

H-O-C(Et)(Et)-C(Et)=N-Me

-continued
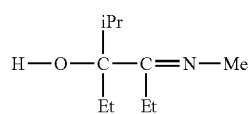 No. 416
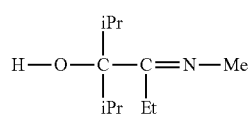 No. 417
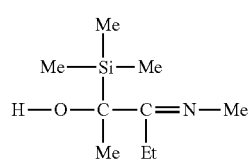 No. 418
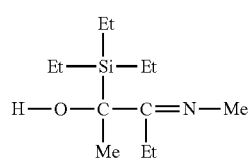 No. 419
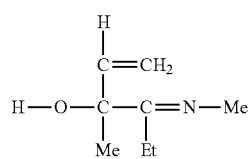 No. 420
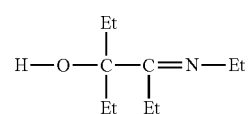 No. 421
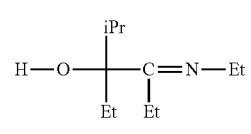 No. 422
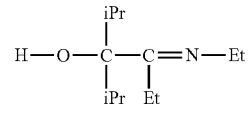 No. 423
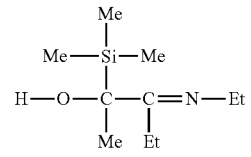 No. 424
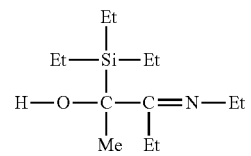 No. 425
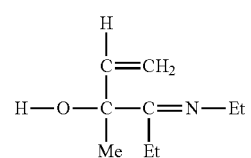 No. 426
-continued
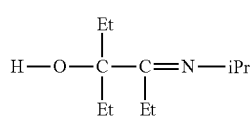 No. 427
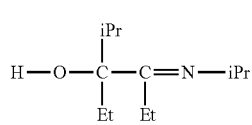 No. 428
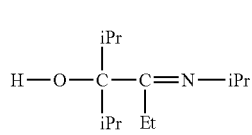 No. 429
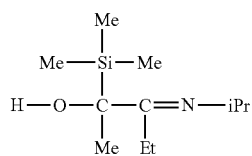 No. 430
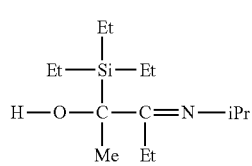 No. 431
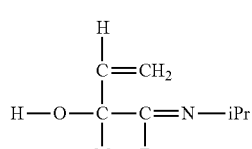 No. 432
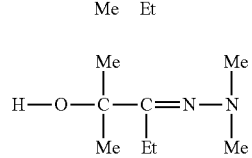 No. 433
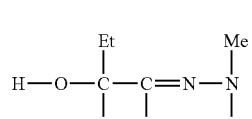 No. 434
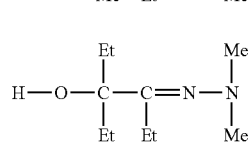 No. 435
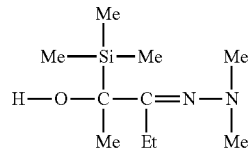 No. 436
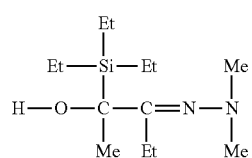 No. 437

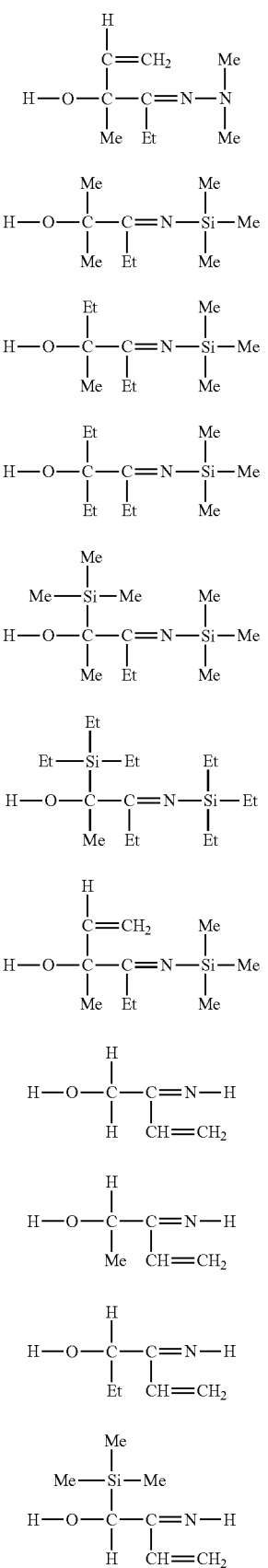
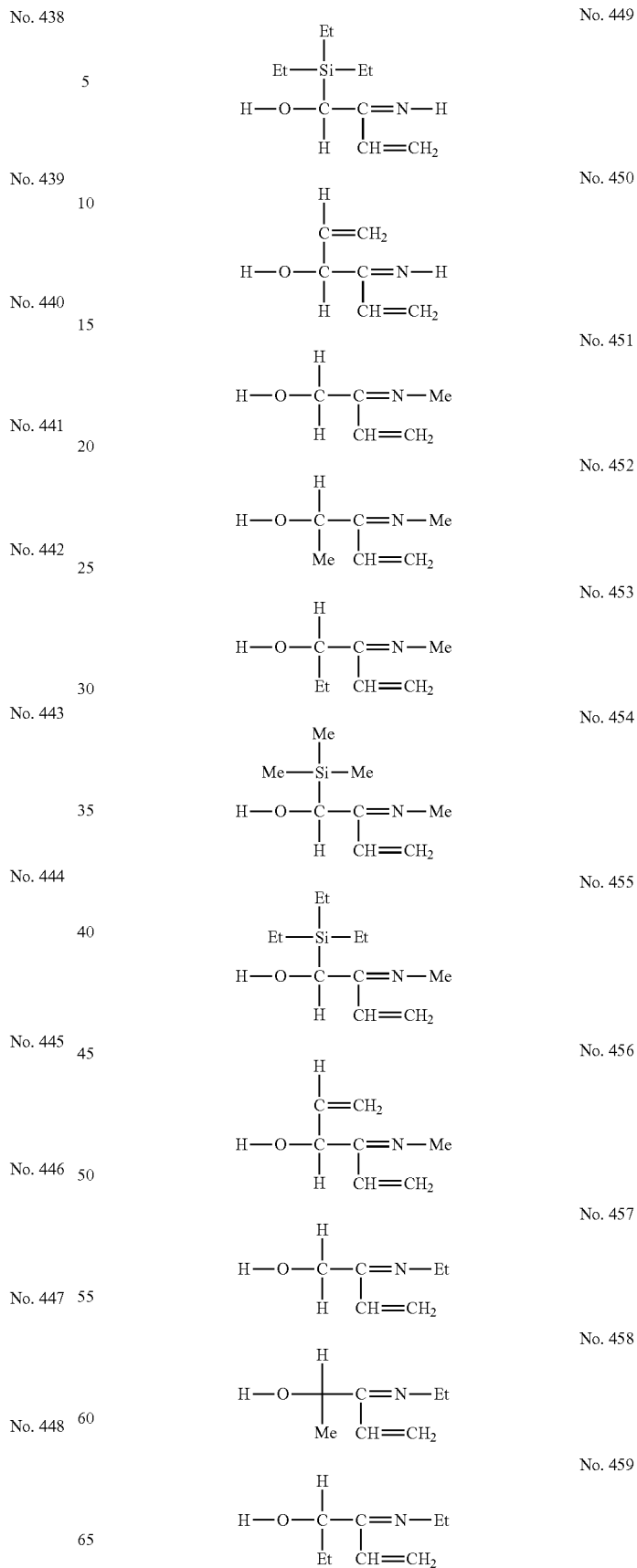

No. 460 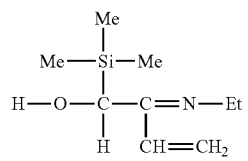
No. 461 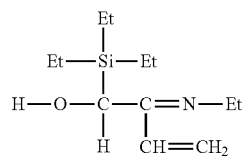
No. 462 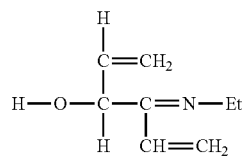
No. 463 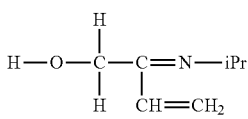
No. 464 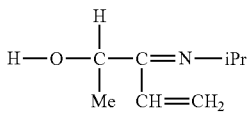
No. 465 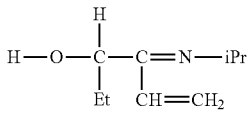
No. 466 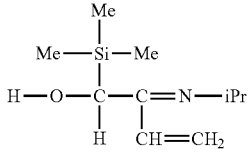
No. 467 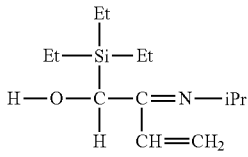
No. 468 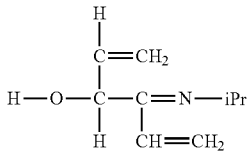
No. 469 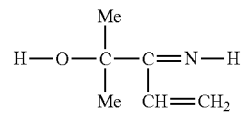
No. 470 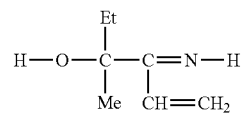
No. 471 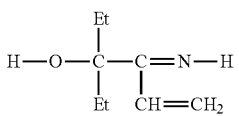
No. 472 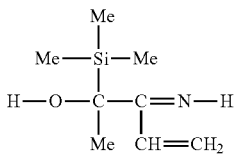
No. 473 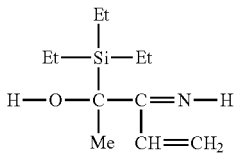
No. 474 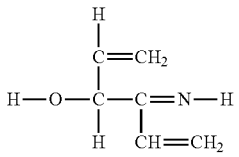
No. 475 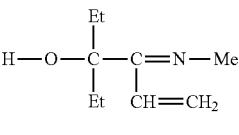
No. 476 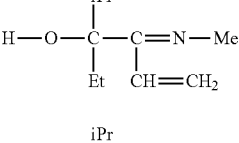
No. 477 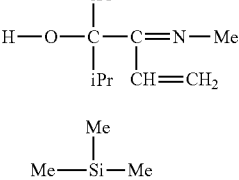
No. 478 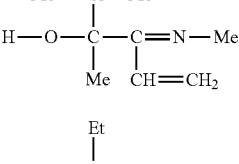
No. 479 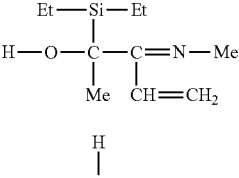
No. 480 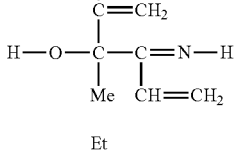
No. 481 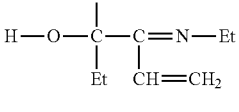

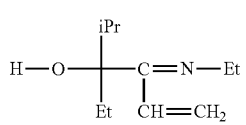
No. 482
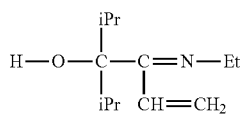
No. 483
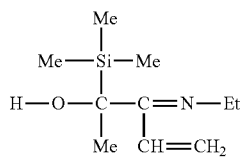
No. 484
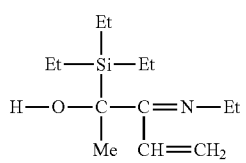
No. 485
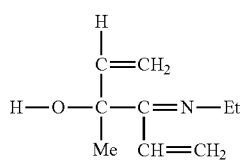
No. 486
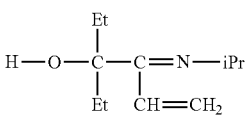
No. 487
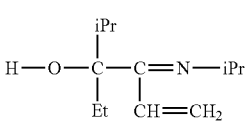
No. 488
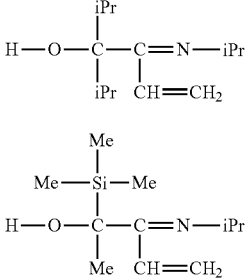
No. 489
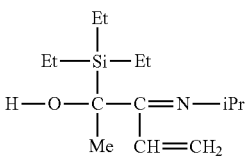
No. 490
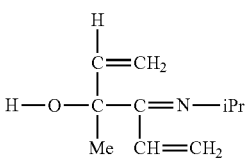
No. 491
No. 492
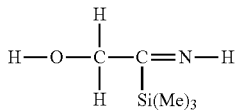
No. 493
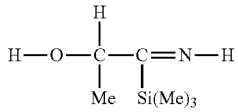
No. 494
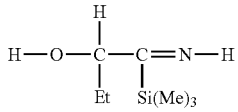
No. 495
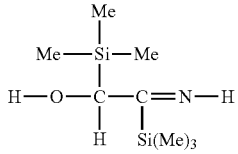
No. 496
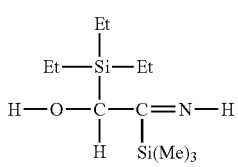
No. 497
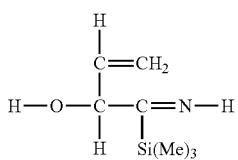
No. 498
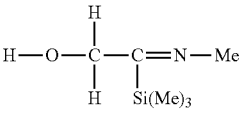
No. 499
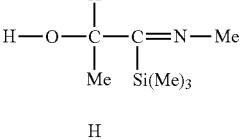
No. 500
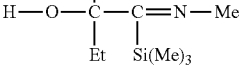
No. 501
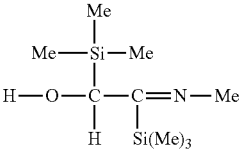
No. 502
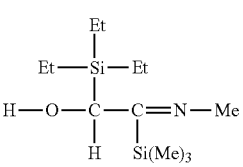
No. 503

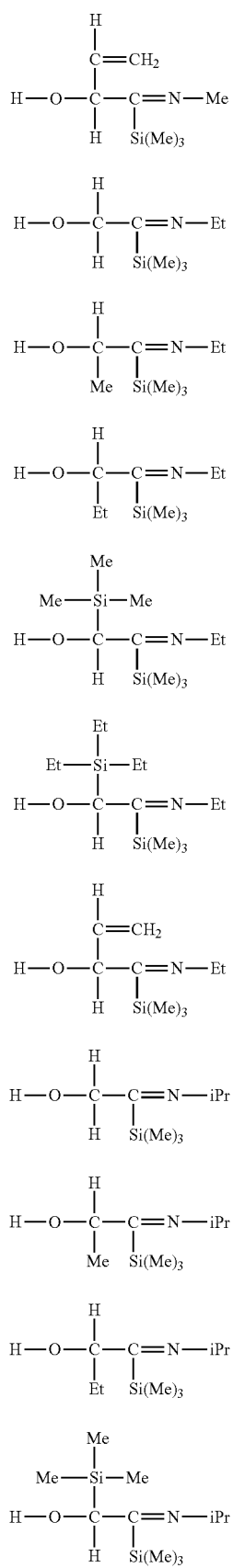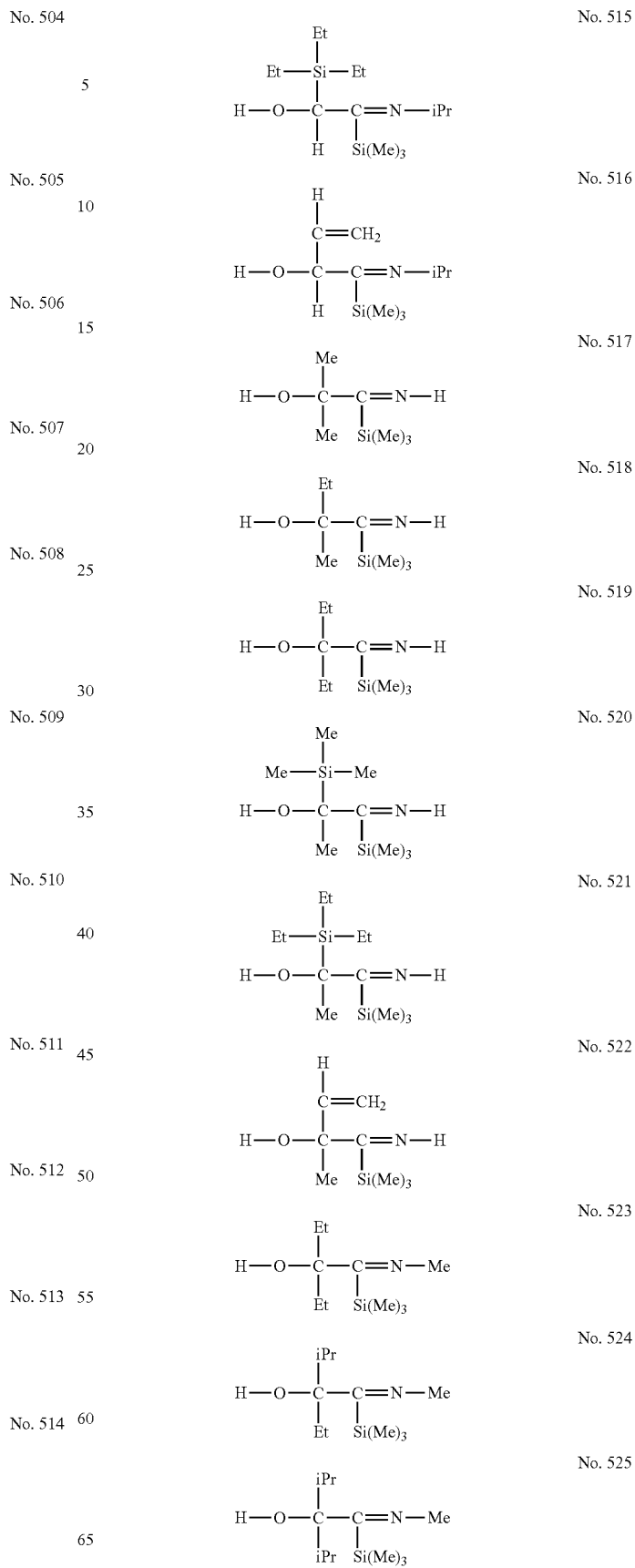

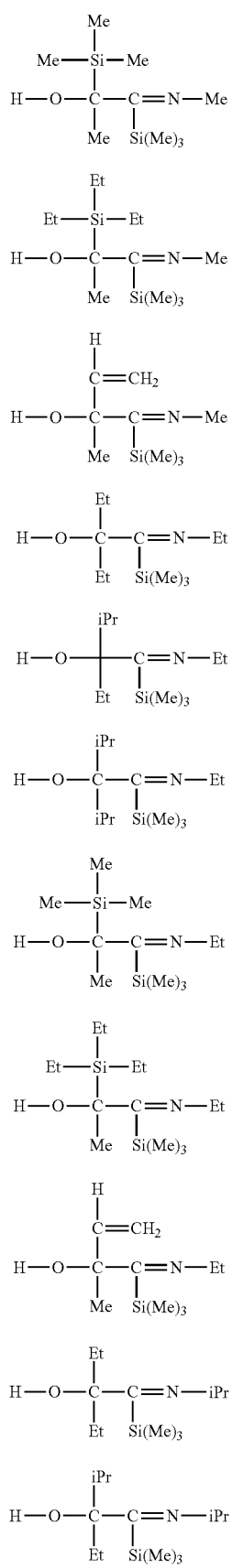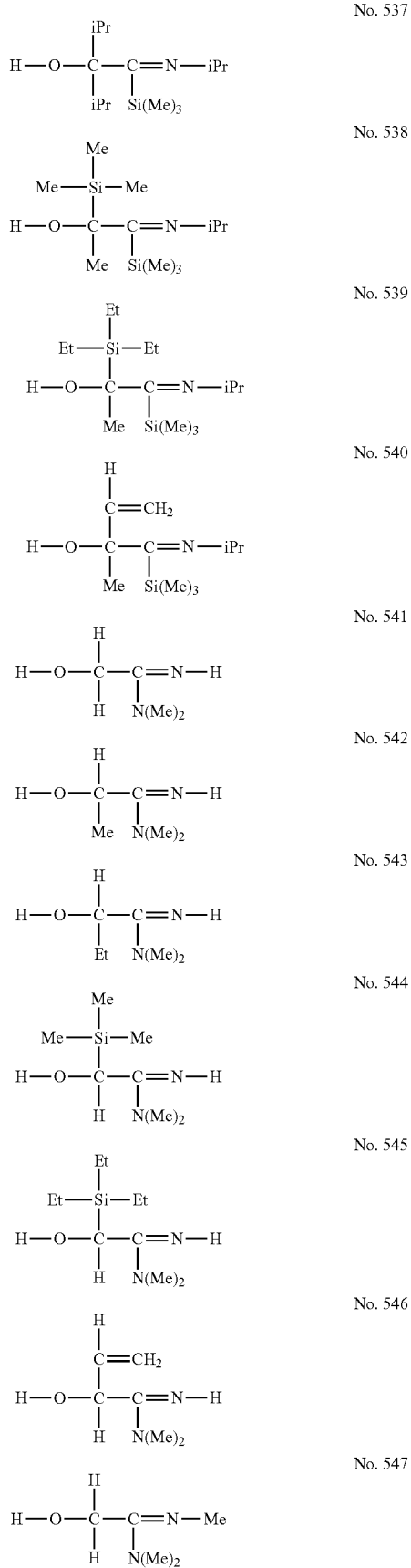

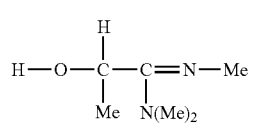
No. 548
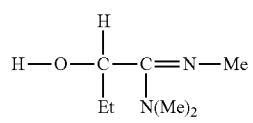
No. 549
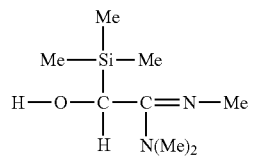
No. 550
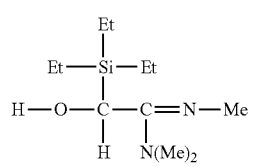
No. 551
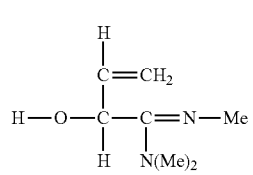
No. 552
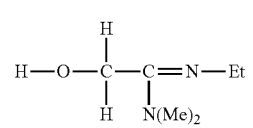
No. 553
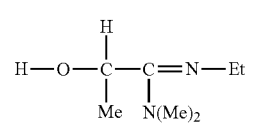
No. 554
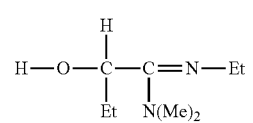
No. 555
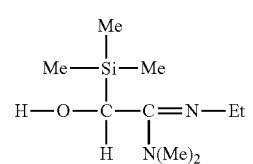
No. 556
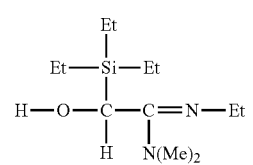
No. 557
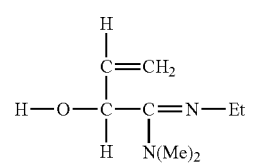
No. 558
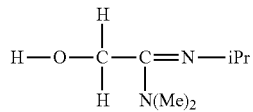
No. 559
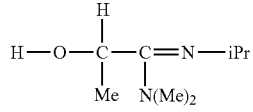
No. 560
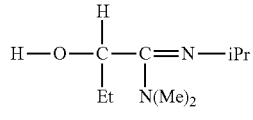
No. 561
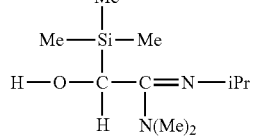
No. 562
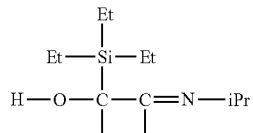
No. 563
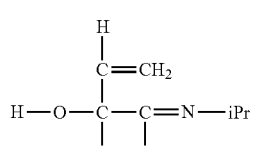
No. 564
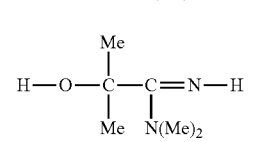
No. 565
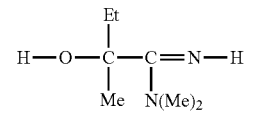
No. 566
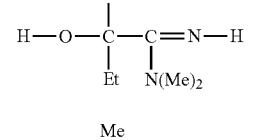
No. 567
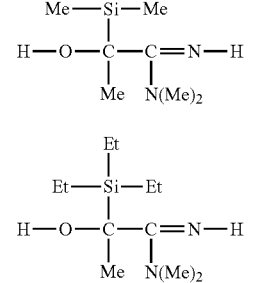
No. 568
No. 569

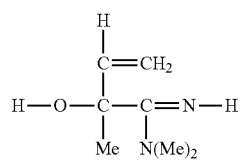
No. 570

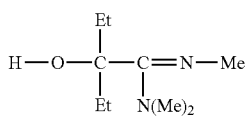
No. 571

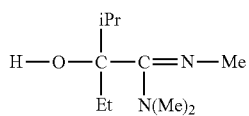
No. 572

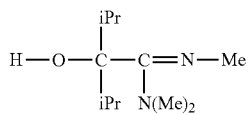
No. 573

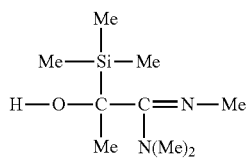
No. 574

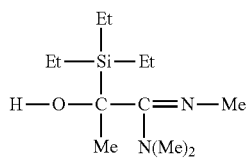
No. 575

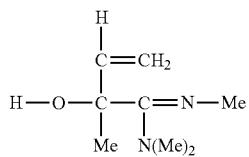
No. 576

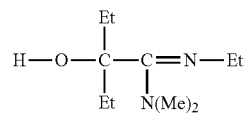
No. 577

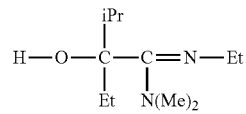
No. 578

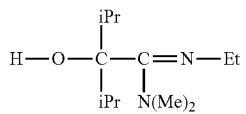
No. 579

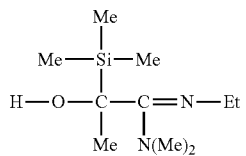
No. 580

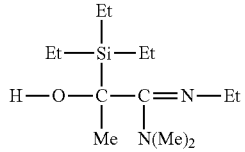
No. 581

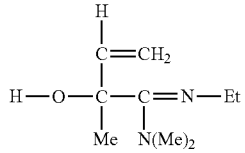
No. 582

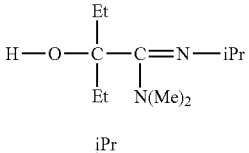
No. 583

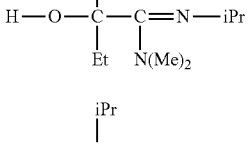
No. 584

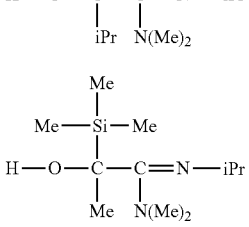
No. 585

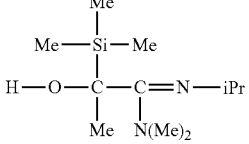
No. 586

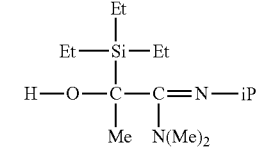
No. 587

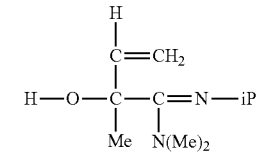
No. 588

The alcohol compound of the present invention is not restricted by the manufacturing method thereof and can be manufactured by using well-known reactions.

For example, the alcohol compound can be obtained by a method in which a Grignard reaction of an alkyl compound and an alkoxycarboxylic acid alkyl compound is conducted using magnesium as a catalyst, a reaction is then conducted with an alkylamine, and the product is extracted with an appropriate solvent and dehydrated, as represented by Reaction Formula (1); a method in which a Grignard reaction of an alkyl compound and an alkoxyketone alkyl compound is conducted using magnesium as a catalyst, a reaction is then conducted with an alkylamine, and the product is extracted with an appropriate solvent and dehydrated, as represented by Reaction Formula (2); and a method in which a Grignard reaction of an alkyl compound and a dialkyldiketone compound is conducted using magnesium as a catalyst, a reaction is then conducted with an alkylamine, and the product is extracted with an appropriate solvent and dehydrated, as represented by Reaction Formula (3).

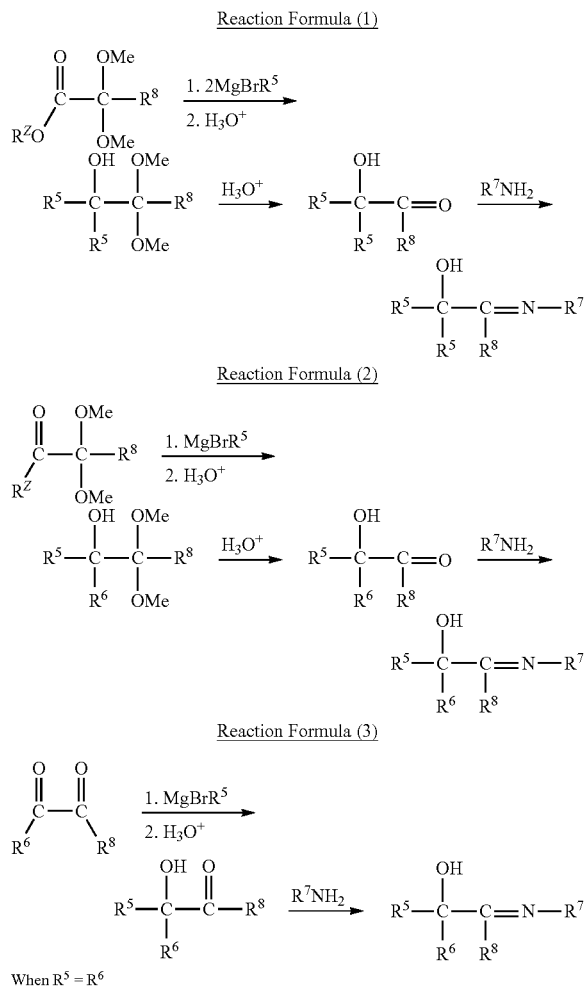

In Reaction Formula (1) and Reaction Formula (2), $R^z$ represents an alkyl group.

The alcohol compound of the present invention can be used as a ligand of a metal compound to be used in a raw material for forming a thin film, and the like. The alcohol compound of the present invention can be also used as, for example, a raw material for synthesis of solvents, perfumes, agricultural chemicals, medicines, various polymers and the like.

EXAMPLES

The present invention will be explained hereinbelow in greater detail with reference to Examples and Evaluation Examples. However, the present invention is not limited by the Examples, etc., below.

Example 1

Synthesis of Compound No. 343

A total of 8.69 g of magnesium and 253 g of tetrahydrofuran were placed in a reaction flask and stirred at a room temperature. A total of 40.45 g of bromoethane was added dropwise to the solution over 1 h and stirred for 2 h. The solution was then cooled with ice, 25.04 g of methyl 2,2-dimethoxypropionate was added dropwise over 30 min, and the Grignard reaction was performed. The temperature was then returned to room temperature and the reaction was conducted for 15 h. The reaction liquid was cooled with ice, 119 g of a 23% hydrochloric acid solution was added and stirring was performed for 3 h. Only the organic layer was fractionated and recovered, 68.73 g of a 40% aqueous methylamine solution was then added dropwise at room temperature, and the reaction was conducted for 24 h. The pH of the reaction liquid at this time was 10 to 11. A total of 119 g of toluene was then added, an organic layer was extracted and fractionated, magnesium sulfate was added, and dehydration and filtration were performed. The solvent was removed at 90° C. in an oil bath under a reduced pressure, and after the solvent was distilled off, distillation was performed to yield a colorless transparent liquid target product (3-ethyl-2-methylimino-3-pentanol). The yield amount was 17.32 g and the yield ratio was 65%.

(Analytical Data)
(1) GC-MS m/z: 143 (M+)
(2) $^1$NMR (solvent: heavy benzene) (chemical shift: multiplicity: H number) (5.65: s: 1) (2.78: s: 3) (1.63 to 1.72: m: 2) (1.35 to 1.44: m: 2) (1.21: s: 3) (0.79 to 0.83: t: 6)
(3) Elemental analysis C: 66.9 mass %, H: 12.3 mass %, O: 11.5 mass %, N: 9.9 mass %, (theoretical values; C: 67.1 mass %, H: 11.9 mass %, O: 11.1 mass %, N: 9.8 mass %)

Example 2

Synthesis of Compound No. 349

A total of 8.62 g of magnesium and 244 g of tetrahydrofuran were placed in a reaction flask and stirred at a room temperature. A total of 41.4 g of bromoethane was added dropwise to the solution over 1 h and stirred for 3 h. The solution was then cooled with ice, 25.03 g of methyl 2,2-dimethoxypropionate was added dropwise over 30 min, and the Grignard reaction was performed. The temperature was then returned to room temperature and the reaction was conducted for 20 h. The reaction liquid was cooled with ice, 103 g of a 22% hydrochloric acid solution was added and stirring was performed for 2 h. Only the organic layer was fractionated and recovered, 107.64 g of a 33% aqueous ethylamine solution was then added dropwise at room temperature, and the reaction was conducted for 48 h. The pH of the reaction liquid at this time was 10 to 11. A total of 104 g of toluene was then added, an organic layer was extracted and fractionated, magnesium sulfate was added, and dehydration and filtration were performed. The solvent was removed at 80° C. in an oil bath under a reduced pressure, and after the solvent was distilled off, distillation was performed to yield a colorless transparent liquid target product (2-ethylimino-3-ethyl-3-pentanol). The yield amount was 9.30 g and the yield ratio was 33%.

(Analytical Data)
(1) GC-MS m/z: 157 (M+)
(3) Elemental analysis C: 69.4 mass %, H: 12.5 mass %, O: 10.5 mass %, N: 8.2 mass %, (theoretical values; C: 68.8 mass %, H: 12.1 mass %, O: 10.2 mass %, N: 8.9 mass %)

Example 3

Synthesis of Compound No. 43

A total of 7.01 g of cobalt (II) chloride and 25.5 g of tetrahydrofuran were charged into a four-neck flask with a capacity of 200 ml and stirred at a room temperature. A total of 17.3 g of sodium alkoxide obtained by preparation from the alcohol (3-ethyl-2-methylimino-3-pentanol) synthesized in Example 1 was diluted with 20.7 g of tetrahydrofuran, and the solution was added dropwise to the flask under ice cooling. After the end of dropping, stirring was performed for 15 h at room temperature, followed by filtration. Tetrahydrofuran was removed from the obtained filtrate, and the residue was sublimated under the conditions of 46 Pa and 100° C. The target product was obtained in a yield amount of 8.22 g at a yield ratio of 37.8%.
(Analytical Data)
 (1) Normal-pressure TG-DTA
 temperature of 50% mass reduction: 214° C. (Ar flow rate: 100 mi/min; temperature increase rate 10° C./min)
 (2) Reduced-pressure TG-DTA
 temperature of 50% mass reduction: 135° C. (10 Torr, Ar flow rate: 50 mi/min; temperature increase rate 10° C./min)
 (3) Elemental analysis Co: 17.5: mass %, C: 55.7 mass %, H: 9.0 mass %, O: 8.9 mass %, N: 8.2 mass %, (theoretical values; Co: 17.2: mass %, C: 56.0 mass %, H: 9.3 mass %, O: 9.3 mass %, N: 8.1 mass %)

Example 4

Synthesis of Compound No. 49

A total of 3.65 g of cobalt (II) chloride and 13.7 g of tetrahydrofuran were charged into a three-neck flask with a capacity of 100 ml and stirred at a room temperature. A total of 9.86 g of sodium alkoxide obtained by preparation from the alcohol (2-ethylimino-3-ethyl-3-pentanol) synthesized in Example 2 was diluted with 19.4 g of tetrahydrofuran, and the solution was added dropwise to the flask under ice cooling. After the end of dropping, stirring was performed for 15 h at room temperature, followed by filtration. Tetrahydrofuran was removed from the obtained filtrate, and the residue was sublimated under the conditions of 58 Pa, bath temperature 150° C., column top temperature 108° C. The target product was obtained in a yield amount of 7.05 g at a yield ratio of 68.4%.
(Analytical Data)
 (1) Normal-pressure TG-DTA
 temperature of 50% mass reduction: 215° C. (Ar flow rate: 100 ml/min; temperature increase rate 10° C./min)
 (2) Reduced-pressure TG-DTA
 temperature of 50% mass reduction: 137° C. (10 Torr, Ar flow rate: 50 mi/min; temperature increase rate 10° C./min)
 (3) Elemental analysis Co: 16.1 mass %, C: 58.7 mass %, H: 9.2 mass %, O: 8.4 mass %, N: 7.1 mass %, (theoretical values; Co: 15.9 mass %, C: 58.2 mass %, H: 9.7 mass %, O: 8.6 mass %, N: 7.5 mass %)
(Evaluation of Spontaneous Combustion]
Spontaneous combustion was checked with respect to Compounds No. 43 and 49 and the below-described Comparative Compounds 1 to 3 by allowing the compounds to stay in the air. The results are shown in Table 1.

TABLE 1

| Compound | Spontaneous Combustion |
| --- | --- |
| Comparative Compound 1 | None |
| Comparative Compound 2 | None |
| Comparative Compound 3 | None |

TABLE 1-continued

| Compound | Spontaneous Combustion |
| --- | --- |
| Compound No. 43 | None |
| Compound No. 49 | None |

[Evaluation of Thermal Stability]
Thermal stability of Compounds No. 43 and 49 and Comparative Compounds 1 to 3 was checked by measuring the temperature at which an exothermic peak was observed as a thermal decomposition initiation temperature by using a DSC measurement device. The results are shown in Table 2. When thermal stability of a raw material for forming a thin film is high, the film can be formed at a higher temperature. The possibility of forming a film at a higher temperature means that the amount of impurities, such as carbon residue, contained in the obtained thin film can be reduced. Therefore, thermal stability of a raw material for forming a thin film affects the quality of the thin film which is to be obtained.

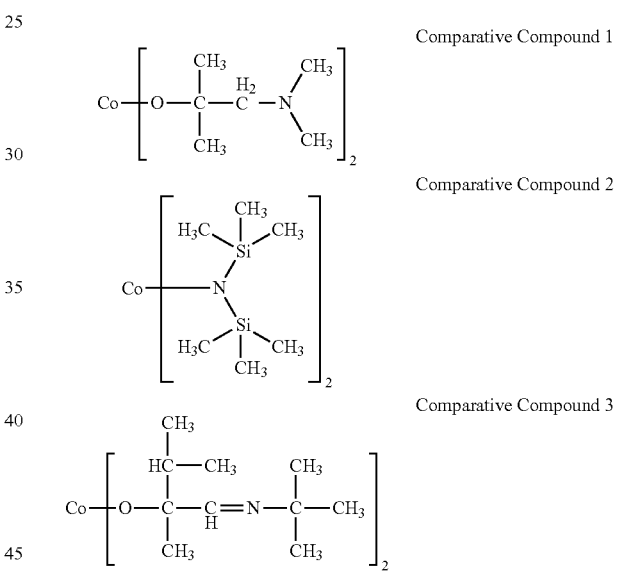

TABLE 2

| Compound | Thermal Decomposition Initiation Temperature |
| --- | --- |
| Comparative Compound 1 | 220° C. |
| Comparative Compound 2 | 210° C. |
| Comparative Compound 3 | 230° C. |
| Compound No. 43 | 320° C. |
| Compound No. 49 | 310° C. |

It follows from the results shown in Table 2 that where Compounds No. 43 and 49 and Comparative Compounds 1 to 3 are compared, the thermal stability of Compounds No. 43 and 49 is higher than that of Comparative Compounds 1 to 3. Further, the measurement results of normal-pressure TG-DTA indicate that the temperature of 50% mass reduction of Compounds No. 43 and 49 is 214° C. and 215° C., respectively. Therefore, these compounds can be said to demonstrate sufficient volatility as CVD sources.

Example 5

Manufacture of Thin Film of Metallic Cobalt by ALD Method

Compound No. 43 was taken as a raw material for chemical vapor deposition, and a thin film of metallic cobalt was manufactured on a silicon wafer by the ALD method under the below-described conditions by using the apparatus depicted in FIG. 2. The thickness of the obtained thin film was measured by an X-ray reflectance method, and the thin film structure and thin film composition were verified by an X-ray diffraction method and an X-ray photoelectron spectroscopy. The film thickness was 4 nm to 7 nm, the film composition was metallic cobalt (confirmed by Co 2p peak in XPS analysis), and the amount of carbon was less than the lower detection limit of 0.1 atom %. The film thickness obtained per one cycle was 0.08 nm to 0.14 nm.

(Conditions)

Reaction temperature (substrate temperature): 300° C. to 350° C., Reactive gas: hydrogen gas (Steps)

The series of the following steps (1) to (4) was taken as 1 cycle, and 50 cycles were performed.

(1) The vapor of a raw material for chemical vapor deposition that was vaporized under the conditions of a vaporization chamber temperature of 140° C. and a vaporization chamber pressure of 100 Pa is introduced, and deposition is performed for 30 s under a system pressure of 100 Pa.
(2) The unreacted raw material is removed by purging with argon for 5 seconds.
(3) A reactive gas is introduced and the reaction is conducted for 30 s under a system pressure of 100 Pa.
(4) The unreacted raw material is removed by purging with argon for 5 seconds.

Example 6

Manufacture of Thin Film of Metallic Cobalt by ALD Method

Compound No. 49 was taken as a raw material for chemical vapor deposition, and a thin film of metallic cobalt was manufactured on a silicon wafer by the ALD method under the below-described conditions by using the apparatus depicted in FIG. 1. The thickness of the obtained thin film was measured by an X-ray reflectance method, and the thin film structure and thin film composition were verified by an X-ray diffraction method and an X-ray photoelectron spectroscopy. The film thickness was 2 nm to 5 nm, the film composition was metallic cobalt (confirmed by Co 2p peak in XPS analysis), and the amount of carbon was less than the lower detection limit of 0.1 atom %. The film thickness obtained per one cycle was 0.04 nm to 0.1 nm.

(Conditions)

Reaction temperature (substrate temperature): 300° C. to 350° C., Reactive gas: hydrogen gas (Steps)

The series of the following steps (1) to (4) was taken as 1 cycle, and 50 cycles were performed.

(1) The vapor of a raw material for chemical vapor deposition that was vaporized under the conditions of a vaporization chamber temperature of 100° C. and a vaporization chamber pressure of 100 Pa is introduced, and deposition is performed for 30 s under a system pressure of 100 Pa.
(2) The unreacted raw material is removed by purging with argon for 5 seconds.
(3) A reactive gas is introduced and the reaction is conducted for 30 s under a system pressure of 100 Pa.
(4) The unreacted raw material is removed by purging with argon for 5 seconds.

The present international application claims priority from Japanese Patent Application No. 2014-087310 filed on Apr. 21, 2014, the full contents whereof are incorporated herein by reference.

The invention claimed is:

1. An alkoxide compound of the Formula No. 43 or the Formula No. 49 below:

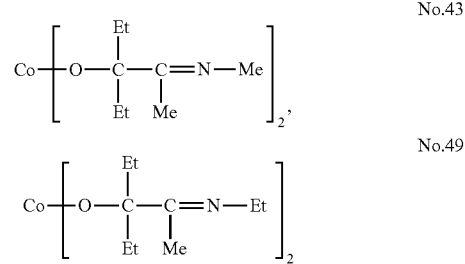

wherein in the Formula No. 43 and the Formula No. 49, Et represents ethyl and Me represents methyl.

2. A raw material for forming a thin film, comprising the alkoxide compound according to claim 1.

3. A method for manufacturing a thin film, comprising: introducing a vapor including an alkoxide compound obtained by vaporizing the raw material for forming a thin film according to claim 2 into a film formation chamber in which a substrate is disposed; and forming, on a surface of the substrate, a thin film including a metal atom by inducing decomposition and/or chemical reaction of the alkoxide compound.

* * * * *